(12) United States Patent
Wang et al.

(10) Patent No.: US 8,912,195 B2
(45) Date of Patent: Dec. 16, 2014

(54) ALKYL AMIDES AS HIV ATTACHMENT INHIBITORS

(75) Inventors: Tao Wang, Farmington, CT (US);
Zhongxing Zhang, Madison, CT (US);
Zhiwei Yin, Glastonbury, CT (US); John F. Kadow, Wallingford, CT (US);
Nicholas A. Meanwell, East Hampton, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/990,815

(22) PCT Filed: Dec. 1, 2011

(86) PCT No.: PCT/US2011/062804
§ 371 (c)(1),
(2), (4) Date: May 31, 2013

(87) PCT Pub. No.: WO2012/075235
PCT Pub. Date: Jun. 7, 2012

(65) Prior Publication Data
US 2013/0252968 A1     Sep. 26, 2013

Related U.S. Application Data

(60) Provisional application No. 61/418,994, filed on Dec. 2, 2010.

(51) Int. Cl.
*A61K 31/496*     (2006.01)
*C07D 471/04*     (2006.01)
*C07D 403/04*     (2006.01)

(52) U.S. Cl.
CPC .................................. *C07D 471/04* (2013.01)
USPC .................. 514/253.04; 514/254.05; 544/362; 544/373

(58) Field of Classification Search
None
See application file for complete search history.

(56) References Cited

U.S. PATENT DOCUMENTS

| | | |
|---|---|---|
| 6,573,262 B2 | 6/2003 | Wallace et al. |
| 7,348,337 B2 | 3/2008 | Wang et al. |
| 7,354,924 B2 | 4/2008 | Wang et al. |
| 7,396,830 B2 | 7/2008 | Wang et al. |
| 7,501,420 B2 | 3/2009 | Wang et al. |
| 7,504,399 B2 | 3/2009 | Wang et al. |
| 7,745,625 B2 | 6/2010 | Ueda et al. |
| 7,776,863 B2 | 8/2010 | Lin et al. |
| 7,851,476 B2 | 12/2010 | Chen et al. |
| 2005/0215543 A1 | 9/2005 | Lin et al. |
| 2005/0215544 A1 | 9/2005 | Lin et al. |
| 2006/0094717 A1 * | 5/2006 | Regueiro-Ren et al. ... 514/234.2 |

FOREIGN PATENT DOCUMENTS

| | | |
|---|---|---|
| WO | WO 03/103607 | 12/2003 |
| WO | WO 2004/011425 | 2/2004 |
| WO | WO 2005/016344 | 2/2005 |
| WO | WO 2005/121094 | 12/2005 |
| WO | WO 2007/103456 | 9/2007 |

OTHER PUBLICATIONS

Blair, W.S. et al., "HIV-1 entry—an expanding portal for drug discovery", Drug Discovery Today, vol. 5, No. 5, pp. 183-194 (2000).
Hotoda, H., "Small-molecule inhibitors of HIV-1 entry via chemokine receptors", Drugs of the Future, vol. 24, No. 12, pp. 1355-1362 (1999).

(Continued)

*Primary Examiner* — Emily Bernhardt
(74) *Attorney, Agent, or Firm* — John F. Levis

(57) ABSTRACT

Compounds of Formula (I), including pharmaceutically acceptable salts thereof, wherein A is selected from the group (II), are useful as HIV attachment inhibitors.

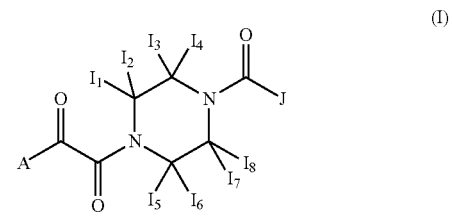

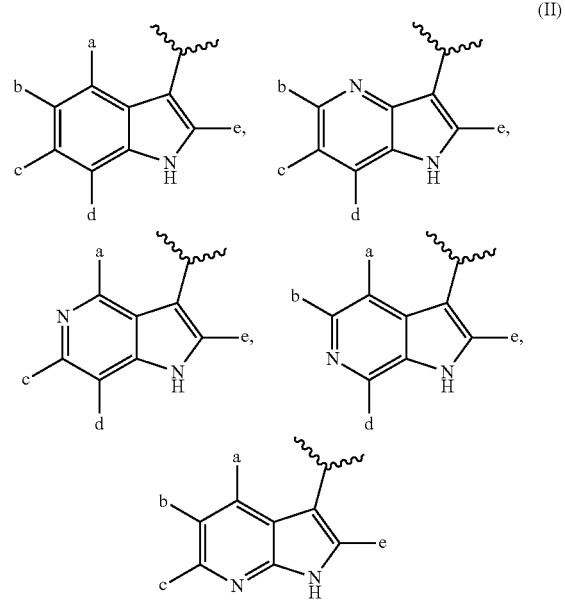

3 Claims, No Drawings

(56) References Cited

OTHER PUBLICATIONS

Lu, R.-J. et al., "Design and Synthesis of Human Immunodeficiency Virus Entry Inhibitors: Sulfonamide as an Isostere for the α-Ketoamide Group," J. Med. Chem., vol. 50, pp. 6535-6544 (2007).
Meanwell, N.A. et al., "Inhibitors of HIV-1 attachment. Part 3: A preliminary survey of the effect of structural variation of the benzamide moiety on antiviral activity," Bioorganic & Medicinal Chemistry Letters, vol. 19, pp. 5136-5139 (2009).

Meanwell, N.A. et al., "Inhibitors of the entry of HIV into host cells", Current Opinion in Drug Discovery & Development, vol. 6, No. 4, pp. 451-461 (2003).
Sodroski, J.G., "HIV-1 Entry Inhibitors in the Side Pocket: Minireview", Cell, vol. 99, pp. 243-246 (1999).
Wang, J. et al., "Modification and structure-activity relationship of a small molecule HIV-1 inhibitor targeting the viral envelope glycoprotein gp120", Org. Biomol. Chem., vol. 3, pp. 1781-1786 (2005).

* cited by examiner

ALKYL AMIDES AS HIV ATTACHMENT INHIBITORS

FIELD OF THE INVENTION

This invention provides compounds having drug and bio-affecting properties, their pharmaceutical compositions and methods of use. In particular, the invention herein is directed to piperazine alkyl amides as HIV attachment inhibitors that possess unique antiviral activity.

BACKGROUND OF THE INVENTION

HIV-1 (human immunodeficiency virus-1) infection remains a major medical problem, with an estimated 45 million people infected worldwide at the end of 2007. The number of cases of HIV and AIDS (acquired immunodeficiency syndrome) has risen rapidly. In 2005, approximately 5.0 million new infections were reported, and 3.1 million people died from AIDS. Currently available drugs for the treatment of HIV include nucleoside reverse transcriptase (RT) inhibitors or approved single pill combinations: zidovudine (or AZT or RETROVIR®), didanosine (or VIDEX®), stavudine (or ZERIT®), lamivudine (or 3TC or EPIVIR®), zalcitabine (or DDC or HIVID®), abacavir succinate (or ZIAGEN®), tenofovir disoproxil fumarate salt (or VIREAD®), emtricitabine (or FTC–EMTRIVA®), COMBIVIR® (contains –3TC plus AZT), TRIZIVIR® (contains abacavir, lamivudine, and zidovudine), Epzicom (contains abacavir and lamivudine), TRUVADA® (contains VIREAD® and EMTRIVA®); non-nucleoside reverse transcriptase inhibitors: nevirapine (or VIRAMUNE®), delavirdine (or RESCRIPTOR®) and efavirenz (or SUSTIVA®), Atripla (TRUVADA®+SUSTIVA®), and etravirine, and peptidomimetic protease inhibitors or approved formulations: saquinavir, indinavir, ritonavir, nelfinavir, amprenavir, lopinavir, KALETRA® (lopinavir and Ritonavir), darunavir, atazanavir (REYATAZ®) and tipranavir (APTIVUS®), and integrase inhibitors such as raltegravir (Isentress), and entry inhibitors such as enfuvirtide (T-20) (FUZEON®) and maraviroc (Selzentry).

Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients may ultimately fail combination drug therapies. Insufficient drug potency, non-compliance, restricted tissue penetration and drug-specific limitations within certain cell types (e.g., most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when suboptimal drug concentrations are present. Therefore, novel anti-HIV agents exhibiting distinct resistance patterns, and favorable pharmacokinetic as well as safety profiles are needed to provide more treatment options. Improved HIV fusion inhibitors and HIV entry coreceptor antagonists are two examples of new classes of anti-HIV agents further being studied by a number of investigators.

HIV attachment inhibitors are a novel subclass of antiviral compounds that bind to the HIV surface glycoprotein gp120, and interfere with the interaction between the surface protein gp120 and the host cell receptor CD4. Thus, they prevent HIV from attaching to the human CD4 T-cell, and block HIV replication in the first stage of the HIV life cycle. The properties of HIV attachment inhibitors have been improved in an effort to obtain compounds with maximized utility and efficacy as antiviral agents. A disclosure describing indoles of which the structure shown below for BMS-705 is representative, has been disclosed (Antiviral Indoleoxoacetyl piperazine Derivatives).

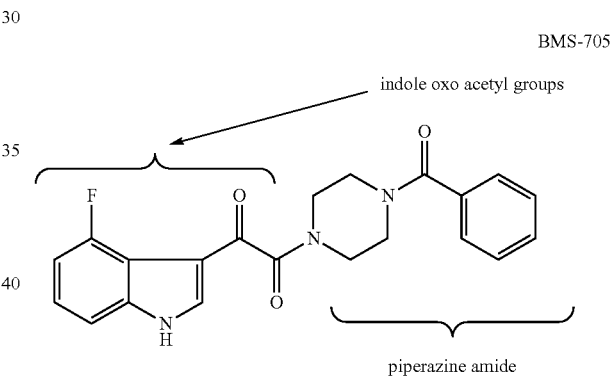

BMS-705

Two other compounds, referred to in the literature as BMS-806 and BMS-043 have been described in both the academic and patent art:

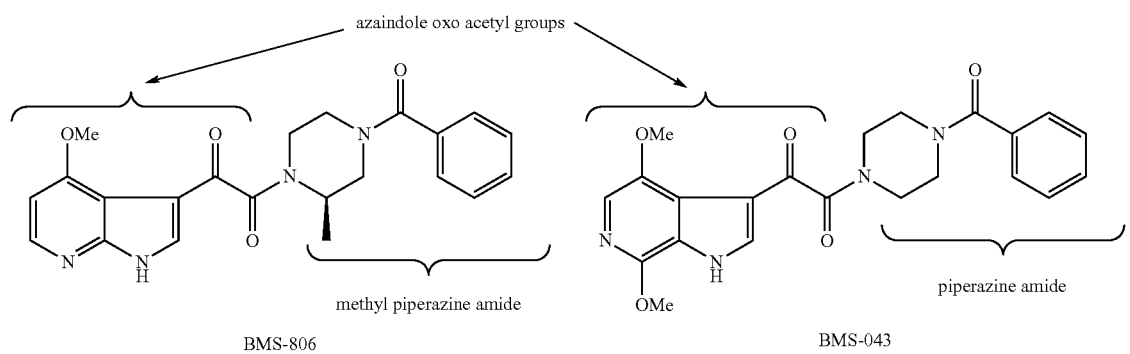 [SMILES: COc1ccnc2[nH]cc(C(=O)C(=O)N3CCN(C(=O)c4ccccc4)C[C@H]3C)c12 ; COc1ncc(OC)c2c(C(=O)C(=O)N3CCN(C(=O)c4ccccc4)CC3)c[nH]c12]

BMS-806

BMS-043

Some description of their properties in human clinical trials has been disclosed in the literature.

It should be noted that in all three of these structures, a piperazine amide (in these three structures a piperazine phenyl amide) is present and this group is directly attached to an oxoacetyl moiety. The oxoacetyl group is attached at the 3-position of 4-fluoro indole in BMS-705 and to the 3 position of substituted azaindoles in BMS-806 and BMS-043.

In an effort to obtain improved anti-HIV compounds, later publications described in part, modified substitution patterns on the indoles and azaindoles. Examples of such efforts include: (1) novel substituted indoleoxoacetic piperazine derivatives, (2) substituted piperazinyloxoacetylindole derivatives, and (3) substituted azaindoleoxoacetic piperazine derivatives.

Replacement of these groups with other heteroaromatics or substituted heteroaromatics or bicyclic hydrocarbons was also shown to be feasible. Examples include: (1) indole, azaindole and related heterocyclic amidopiperazine derivatives; (2) bicyclo 4.4.0 antiviral derivatives; and (3) diazaindole derivatives.

A select few replacements for the piperazine amide portion of the molecules have also been described in the art and among these examples are (1) some piperidine alkenes; (2) some pyrrolidine amides; (3) some N-aryl or heteroaryl piperazines; (4) some piperazinyl ureas; and (5) some carboline-containing compounds.

Method(s) for preparing prodrugs for this class of compounds are disclosed in Prodrugs of piperazine and Substituted Piperidine Antiviral Agents (Ueda et al., U.S. nonprovisional application Serial. No. 11/066,745, filed Feb. 25, 2005 or U.S. Publication No. 2005/0209246 or WO 2005/090367 A1).

A published PCT patent application WO 2003/103607 A1 (Jun. 11, 2003) disclosures an assay useful for assaying some HIV inhibitors.

Several published patent applications describe combination studies with piperazine benzamide inhibitors, for example, U.S. Publication No. 2005/0215543 (WO 2005/102328 A1), U.S. Publication No. 2005/0215544 (WO 2005/102391 A1), and U.S. Publication No. 2005/0215545 (WO 2005/102392 A2).

A publication on new compounds in this class of attachment inhibitors (Wang, J. et al., Org. Biol. Chem., 3:1781-1786 (2005)) and a patent application on some more remotely related compounds have appeared WO 2005/016344 published on Feb. 24, 2005.

Published patent applications WO 2005/016344 and WO 2005/121094 also describe piperazine derivatives which are HIV inhibitors. Other references in the HIV attachment area include U.S. Publication Nos. 2007/0155702, 2007/0078141 and 2007/0287712, WO 2007/103456, as well as U.S. Pat. Nos. 7,348,337 and 7,354,924. A literature reference is *J. Med. Chem.*, 50:6535 (2007).

What is therefore needed in the art are new HIV attachment inhibitor compounds, and compositions thereof, which are efficacious against HIV infection.

Of particular interest are new piperazine alkyl amides as HIV attachment inhibitor compounds, described herein. The compounds of the present invention are alkyl amide derivatives, which are structurally distinct from the aryl amide HIV attachment inhibitors set forth in literature.

SUMMARY OF THE INVENTION

The present invention provides compounds of Formula I below, the pharmaceutically acceptable salts and/or solvates (e.g., hydrates) thereof, their pharmaceutical formulations, and their use in patients suffering from or susceptible to a virus such as HIV. The compounds of Formula I, their pharmaceutically acceptable salts and/or solvates are effective antiviral agents, particularly as inhibitors of HIV. They are useful for the treatment of HIV and AIDS.

One embodiment of the present invention is directed to a compound of Formula I, including pharmaceutically acceptable salts thereof:

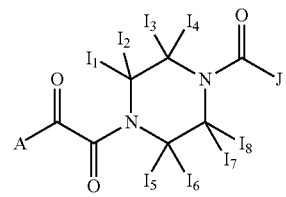

wherein A is selected from the group consisting of:

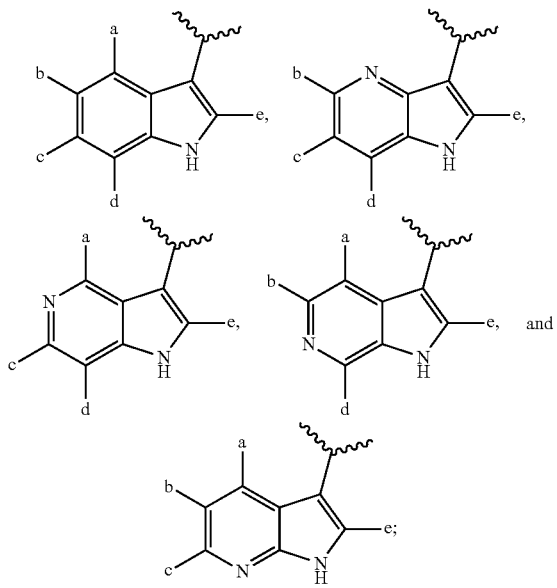

wherein
a, b, c, d and e are independently selected from the group consisting of hydrogen, halogen, cyano, nitro, COOR$^{56}$, XR$^{57}$, NA$^1$A$^2$, C(O)R$^7$, C(O)NR$^{55}$R$^{56}$, B, Q, and E;
B is selected from the group consisting of —C(=NR$^{46}$)(R$^{47}$), C(O)NR$^{40}$R$^{41}$, aryl, heteroaryl, heteroalicyclic, S(O)$_2$R$^8$, C(O)R$^7$, XR$^{8a}$, (C$_{1-6}$)alkylNR$^{40}$R$^{41}$, (C$_{1-6}$)alkylCOOR$^{8b}$;
wherein said aryl, heteroaryl, and heteroalicyclic are optionally substituted with one to three same or different halogens or from one to three same or different substituents selected from the group F; wherein aryl is napthyl or substituted phenyl; wherein heteroaryl is a mono or bicyclic system which contains from 3 to 7 ring atoms for a mono cyclic system and up to 12 atoms in a fused bicyclic system, including from 1 to 4 heteroatoms; wherein heteroalicyclic is a 3 to 7 membered mono cyclic ring which may contain from 1 to 2 heteroatoms in the ring skeleton and which may be fused to a benzene or pyridine ring;
Q is selected from the group consisting of (C$_{1-6}$)alkyl and (C$_{2-6}$)alkenyl; wherein said (C$_{1-6}$)alkyl and (C$_{2-6}$)alkenyl are optionally substituted with one to three same or different halogens or from one to three same or different substituents selected from the group consisting of $C(O)NR^{55}R^{56}$, hydroxy, cyano and $XR^{57}$;

E is selected from the group consisting of $(C_{1-6})$alkyl and $(C_{2-6})$alkenyl; wherein said $(C_{1-6})$alkyl and $(C_{2-6})$alkenyl are independently optionally substituted with a member selected from the group consisting of phenyl, heteroaryl, SMe, SPh, —$C(O)NR^{56}R^{57}$, $C(O)R^{57}$, $SO_2(C_{1-6})$alkyl and $SO_2$Ph; wherein heteroaryl is a monocyclic system which contains from 3 to 7 ring atoms, including from 1 to 4 heteroatoms;

$R^7$ is selected from the group consisting of aryl, heteroaryl, and heteroalicyclic; wherein said aryl, heteroaryl, and heteroalicyclic are optionally substituted with one to three same or different halogens or with from one to three same or different substituents selected from the group F;

wherein for $R^7$, $R^8$, $R^{8a}$, $R^{8b}$ aryl is phenyl; heteroaryl is a mono or bicyclic system which contains from 3 to 7 ring atoms for mono cyclic systems and up to 10 atoms in a bicyclic system, including from 1 to 4 heteroatoms; wherein heteroalicyclic is selected from the group consisting of aziridine, azetidine, pyrrolidine, piperazine, piperidine, tetrahydrofuran, tetrahydropyran, azepine, and morpholine;

F is selected from the group consisting of $(C_{1-6})$alkyl, $(C_{3-7})$cycloalkyl, aryl, heteroaryl, heteroalicyclic, hydroxy, $(C_{1-6})$alkoxy, aryloxy, $(C_{1-6})$thioalkoxy, cyano, halogen, nitro, —$C(O)R^{57}$, benzyl, —$NR^{42}C(O)$—$(C_{1-6})$alkyl, —$NR^{42}C(O)$—$(C_{3-6})$cycloalkyl, —$NR^{42}C(O)$-aryl, —$NR^{42}C(O)$-heteroaryl, —$NR^{42}C(O)$-heteroalicyclic, a 4, 5, or 6 membered ring cyclic N-lactam, —$NR^{42}S(O)_2$—$(C_{1-6})$alkyl, —$NR^{42}S(O)_2$—$(C_{3-6})$cycloalkyl, —$NR^{42}S(O)2$-aryl, —$NR^{42}S(O)_2$-heteroaryl, —$NR^{42}S(O)2$-heteroalicyclic, $S(O)_2(C_{1-6})$alkyl, $S(O)_2$aryl, —$S(O)2$ $NR^{42}R^{43}$, $NR^{42}R^{43}$, $(C_{1-6})$alkylC(O)$NR^{42}R^{43}$, $C(O)NR^{42}R^{43}$, $NHC(O)NR^{42}R^{43}$, $OC(O)NR^{42}R^{43}$, $NHC(O)OR^{54}$, $(C_{1-6})$alkyl$NR^{42}R^{43}$, $COOR^{54}$, and $(C_{1-6})$alkyl$COOR^{54}$; wherein said $(C_{1-6})$alkyl, $(C_{3-7})$cycloalkyl, aryl, heteroaryl, heteroalicyclic, $(C_{1-6})$alkoxy, and aryloxy, are optionally substituted with one to nine same or different halogens or from one to five same or different substituents selected from the group G; wherein aryl is phenyl; heteroaryl is a monocyclic system which contains from 3 to 7 ring atoms, including from 1 to 4 heteroatoms; heteroalicyclic is selected from the group consisting of aziridine, azetidine, pyrrolidine, piperazine, piperidine, tetrahydrofuran, tetrahydropyran, azepine, and morpholine;

$R^8$ is selected from the group consisting of hydrogen, $(C_{1-6})$alkyl, $(C_{3-7})$cycloalkyl, $(C_{2-6})$alkenyl, $(C_{3-7})$cycloalkenyl, $(C_{2-6})$alkynyl, aryl, heteroaryl, and heteroalicyclic; wherein said $(C_{1-6})$alkyl, $(C_{3-7})$cycloalkyl, $(C_{2-6})$alkenyl, $(C_{3-7})$cycloalkenyl, $(C_{2-6})$alkynyl, aryl, heteroaryl, and heteroalicyclic are optionally substituted with one to six same or different halogens or from one to five same or different substituents selected from the group F or $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, acyl sulfamide, sulfate, sulfuric acid, sulfamic acid, phosphate, phosphoric acid, boronic ester, boronic acid, squarate, squaric acid, oxime, hydrazine, peroxide, among which ether, peroxide, thioether, secondary amine, tertiary amine, ammonium, ester, ketone, amide, amidine, oxime, hydrazine can be either acyclic or cyclic; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl;

$R^{8a}$ is a member selected from the group consisting of aryl, heteroaryl, and heteroalicyclic; wherein each member is independently optionally substituted with one to six same or different halogens or from one to five same or different substituents selected from the group F;

$R^{8b}$ is selected from the group consisting of hydrogen, $(C_{1-6})$ alkyl and phenyl;

X is selected from the group consisting of NH or $NCH_3$, O, and S;

$R^{40}$ and $R^{41}$ are independently selected from the group consisting of (a) hydrogen; (b) $(C_{1-6})$alkyl or $(C_{3-7})$cycloalkyl substituted with one to three same or different halogens or from one to two same or different substituents selected from the group F or different functional groups: $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, acyl sulfamide, sulfate, sulfuric acid, sulfamic acid, phosphate, phosphoric acid, boronic ester, boronic acid, squarate, squaric acid, oxime, hydrazine, peroxide, among which ether, peroxide, thioether, secondary amine, tertiary amine, ammonium, ester, ketone, amide, amidine, oxime, hydrazine can be either acyclic or cyclic; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl; and (c) $(C_{1-6})$alkoxy, aryl, heteroaryl or heteroalicyclic; or $R^{40}$ and $R^{41}$ taken together with the nitrogen to which they are attached form a member selected from the group consisting of aziridine, azetidine, pyrrolidine, piperazine, 4-NMe piperazine, piperidine, azepine, and morpholine; and wherein said aryl, heteroaryl, and heteroalicyclic are optionally substituted with one to three same or different halogens or from one to two same or different substituents selected from the group F; wherein for $R^{40}$ and $R^{41}$ aryl is phenyl; heteroaryl is a monocyclic system which contains from 3 to 6 ring atoms, including from 1 to 4 heteroatoms; heteroalicyclic is selected from the group consisting of aziridine, azetidine, pyrrolidine, piperidine, tetrahydrofuran, tetrahydropyran, azepine, and morpholine; provided when B is $C(O)NR^{40}R^{41}$, at least one of $R^{40}$ and $R^{41}$ is not selected from groups (a) or (b);

$R^{42}$ and $R^{43}$ are independently selected from the group consisting of hydrogen, $(C_{1-6})$alkyl, allyl, $(C_{1-6})$alkoxy, $(C_{3-7})$cycloalkyl, aryl, heteroaryl and heteroalicyclic; or $R^{42}$ and $R^{43}$ taken together with the nitrogen to which they are attached form a member selected from the group consisting of aziridine, azetidine, pyrrolidine, piperazine, 4-NMe piperazine, piperidine, azepine, and morpholine; and wherein said $(C_{1-6})$alkyl, $(C_{1-6})$alkoxy, $(C_{3-7})$cycloalkyl, aryl, heteroaryl, and heteroalicyclic are optionally substituted with one to three same or different halogens or from one to two same or different substituents selected from the group G or different functional groups: $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, acyl sulfamide, sulfate, sulfuric acid, sulfamic acid, phosphate, phosphoric acid, boronic ester, boronic acid, squarate, squaric acid, oxime, hydrazine, peroxide, among which ether, peroxide, thioether, secondary amine, tertiary amine, ammonium, ester, ketone, amide, amidine, oxime, hydrazine can be either acyclic or cyclic; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl; wherein for $R^{42}$ and $R^{43}$ aryl is phenyl; heteroaryl is a monocyclic system which contains from 3 to 6 ring atoms, including from 1 to 4 heteroatoms; heteroalicyclic is a member selected from the group consisting of aziridine, azetidine, pyrrolidine, piperazine, piperidine, tetrahydrofuran, tetrahydropyran, azepine, and morpholine;

G is selected from the group consisting of $(C_{1-6})$alkyl, $(C_{3-7})$cycloalkyl, aryl, heteroaryl, heteroalicyclic, hydroxy, $(C_{1-6})$alkoxy, aryloxy, cyano, halogen, nitro, —C(O)$R^{57}$, benzyl, —$NR^{48}$C(O)—$(C_{1-6})$alkyl, —$NR^{48}$C(O)—$(C_{3-6})$cycloalkyl, —$NR^{48}$C(O)-aryl, —$NR^{48}$C(O)-heteroaryl, —$NR^{48}$C(O)-heteroalicyclic, a 4, 5, or 6 membered ring cyclic N-lactam, —$NR^{48}$S(O)$_2$—$(C_{1-6})$alkyl, —$NR^{48}$S(O)$_2$—$(C_{3-6})$cycloalkyl, —$NR^{48}$S(O)2-aryl, —$NR^{48}$S(O)$_2$-heteroaryl, —$NR^{48}$S(O)2-heteroalicyclic, sulfinyl, sulfonyl, sulfonamide, $NR^{48}R^{49}$, $(C_{1-6})$alkyl C(O)$NR^{48}R^{49}$, C(O)$NR^{48}R^{49}$, NHC(O)$NR^{48}R^{49}$, OC(O)$NR^{48}R^{49}$, NHC(O)$OR^{54'}$, $(C_{1-6})$alkyl$NR^{48}R^{49}$, $COOR^{54}$, and $(C_{1-6})$alkyl$COOR^{54}$; wherein aryl is phenyl; heteroaryl is a monocyclic system which contains from 3 to 7 ring atoms, including from 1 to 4 heteroatoms; heteroalicyclic is selected from the group consisting of aziridine, azetidine, pyrrolidine, piperazine, piperidine, tetrahydrofuran, tetrahydropyran, azepine, and morpholine;

$R^{46}$ is selected from the group consisting of H, $OR^{57}$, and $NR^{55}R^{56}$;

$R^{47}$ is selected from the group consisting of H, amino, halogen, phenyl, aryl, heteroaryl and $(C_{1-6})$alkyl;

$R^{48}$ and $R^{49}$ are independently selected from the group consisting of hydrogen, $(C_{1-6})$alkyl, phenyl, aryl and heteroaryl;

$R^{50}$ is selected from the group consisting of H, $(C_{1-6})$alkyl, $(C_{3-6})$cycloalkyl, and benzyl; wherein each of said $(C_{1-6})$alkyl, $(C_{3-7})$cycloalkyl and benzyl are optionally substituted with one to three same or different $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, acyl sulfamide, sulfate, sulfuric acid, sulfamic acid, phosphate, phosphoric acid, boronic ester, boronic acid, squarate, squaric acid, oxime, hydrazine, peroxide, among which ether, peroxide, thioether, secondary amine, tertiary amine, ammonium, ester, ketone, amide, amidine, oxime, hydrazine can be either acyclic or cyclic; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl $R^{54}$ is selected from the group consisting of hydrogen and $(C_{1-6})$alkyl;

$R^{54'}$ is $(C_{1-6})$alkyl;

$R^{55}$ and $R^{56}$ are independently selected from the group consisting of hydrogen and $(C_{1-6})$alkyl; and $R^{57}$ is selected from the group consisting of hydrogen, $(C_{1-6})$alkyl, aryl, heteroaryl; and $A^1$ and $A^2$ are independently selected from hydrogen, $(C_{1-6})$alkyl, aryl, heteroaryl, $SO2D^1$, $SO2ND^2D^3$, $COD^4$, $COCOD^4$, $COOD^4$, $COND^5D^6$, $COCOND^5D^6$, $COCOOD^4$, C(=$ND^7$)$D^8$, C(=$ND^9$)$ND^{10}D^{11}$;

$A^1$ and $A^2$ can either never connect with each other, or conjoin to form a ring structure;

$D^1$, $D^2$, $D^3$, $D^4$, $D^5$, $D^6$, $D^7$, $D^8$, $D^9$, $D^{10}$, and $D^{11}$ are each independently selected from the group consisting of H, $C_1$-$C_{50}$ alkyl, $C_3$-$C_{50}$ cycloalkyl, $C_3$-$C_{50}$ alkenyl, $C_4$-$C_{50}$ cycloalkenyl, phenyl, heteroaryl, $C_3$-$C_{50}$ amide and $C_3$-$C_{50}$ ether; heteroaryl is selected from the group consisting of pyridinyl, pyrazinyl, pyridazinyl, pyrimidinyl, furanyl, thienyl, benzothienyl, thiazolyl, isothiazolyl, oxazolyl, benzooxazolyl, isoxazolyl, imidazolyl, benzoimidazolyl, 1H-imidazo[4,5-b]pyridin-2-yl, 1H-imidazo[4,5-c]pyridin-2-yl, oxadiazolyl, thiadiazolyl, pyrazolyl, tetrazolyl, tetrazinyl, triazinyl and triazolyl; provided the carbon atoms which comprise the carbon-carbon double bond of said $C_3$-$C_{20}$ alkenyl or the carbon-carbon triple bond of said $C_3$-$C_{20}$ alkynyl are not the point of attachment to the nitrogen to which $D^2$, $D^3$, $D^5$, $D^6$, $D^7$, $D^9$, $D^{10}$, and $D^{11}$ is attached; wherein said $C_1$-$C_{50}$ alkyl, $C_3$-$C_{50}$ cycloalkyl, $C_3$-$C_{50}$ alkenyl, $C_4$-$C_{50}$ cycloalkenyl, aryl, phenyl, heteroaryl, $C_3$-$C_{50}$ amide and $C_3$-$C_{50}$ ether is optionally substituted with one to three same or different of the following functionalities: $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, acyl sulfamide, sulfate, sulfuric acid, sulfamic acid, phosphate, phosphoric acid, boronic ester, boronic acid, squarate, squaric acid, oxime, hydrazine, peroxide, among which ether, peroxide, thioether, secondary amine, tertiary amine, ammonium, ester, ketone, amide, amidine, oxime, hydrazine can be either acyclic or cyclic;

$I_1$, $I_2$, $I_3$, $I_4$, $I_5$, $I_6$, $I_7$ and $I_8$ are each independently selected from the group consisting of H, $(C_{1-6})$alkyl, $(C_{3-6})$cycloalkyl, $(C_{2-6})$alkenyl, $(C_{4-6})$cycloalkenyl, $(C_{2-6})$alkynyl, $CR_{81}R_{82}OR_{83}$, $COR_{84}$, $COOR_{85}$, or $CONR_{86}R_{87}$; wherein each of said alkyl and cycloalkyl being optionally substituted with one to three same or different cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, acyl sulfamide, sulfate, sulfuric acid, sulfamic acid, phosphate, phosphoric acid, boronic ester, boronic acid, squarate, squaric acid, oxime, hydrazine, peroxide, among which ether, peroxide, thioether, secondary amine, tertiary amine, ammonium, ester, ketone, amide, amidine, oxime, hydrazine can be either acyclic or cyclic; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl;

J is selected from the group consisting of H, $C_1$-$C_{30}$ alkyl, $C_3$-$C_{15}$ cycloalkyl, $C_4$-$C_{30}$ bicycloalkyl, $C_5$-$C_{30}$ tricycloalkyl, $C_6$-$C_{30}$ tetracycloalkyl, $C_3$-$C_{30}$ alkenyl, $C_4$-$C_{30}$ cycloalkenyl, $C_5$-$C_{30}$ bicycloalkenyl, $C_7$-$C_{30}$ tricycloalkenyl, $C_9$-$C_{30}$ tetracycloalkyl, $C_1$-$C_{30}$ amide, $C_3$-$C_{30}$ cyclic amide, $C_1$-$C_{30}$ amine, $C_3$-$C_{30}$ cyclic amine, $C_2$-$C_{30}$ ester, $C_3$-$C_{30}$ cyclic ester, $C_2$-$C_{30}$ ether, $C_3$-$C_{30}$ cyclic ether, $C_1$-$C_{30}$ sulfonamide, $C_3$-$C_{30}$ cyclic sulfonamide, $C_2$-$C_{30}$ sulfone, $C_3$-$C_{30}$ cyclic sulfone, $C_2$-$C_{30}$ urea, and $C_3$-$C_{30}$ cyclic urea; wherein said $C_1$-$C_{30}$ alkyl, $C_3$-$C_{30}$ cycloalkyl, $C_4$-$C_{30}$ bicycloalkyl, $C_5$-$C_{30}$ tricycloalkyl, $C_6$-$C_{30}$ tetracycloalkyl, $C_3$-$C_{30}$ alkenyl, $C_4$-$C_{30}$ cycloalkenyl, $C_5$-$C_{30}$ bicycloalkenyl, $C_7$-$C_{30}$ tricycloalkenyl, $C_9$-$C_{30}$ tetracycloalkyl, $C_1$-$C_{30}$ amide, $C_3$-$C_{30}$ cyclic amide, $C_1$-$C_{30}$ amine, $C_3$-$C_{30}$ cyclic amine, $C_2$-$C_{30}$ ester, $C_3$-$C_{30}$ cyclic ester, $C_2$-$C_{30}$ ether, $C_3$-$C_{30}$ cyclic ether, $C_1$-$C_{30}$ sulfonamide, $C_3$-$C_{30}$ cyclic sulfonamide, $C_2$-$C_{30}$ sulfone, $C_3$-$C_{30}$ cyclic sulfone, $C_2$-$C_{30}$ urea, and $C_3$-$C_{30}$ cyclic urea is optionally substituted with one to three same or different of the following functionalities: $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, acyl sulfamide, sulfate, sulfuric acid, sulfamic acid, phosphate, phosphoric acid, boronic ester, boronic acid, squarate, squaric acid, oxime, hydrazine, peroxide, among which ether, peroxide, thioether, secondary amine, tertiary amine, ammonium, ester, ketone, amide, amidine, oxime, hydrazine can be either acyclic or cyclic; and $R_{81}$, $R_{82}$, $R_{83}$, $R_{84}$, $R_{85}$, $R_{86}$, and $R_{87}$ are each independently selected from the group consisting of H, $(C_{1-6})$alkyl, $(C_{3-6})$cycloalkyl, $(C_{2-6})$alkenyl, $(C_{4-6})$cycloalkenyl, and $(C_{2-6})$alkynyl.

Another embodiment of the present invention is directed to a method for treating mammals infected with a virus, especially wherein the virus is HIV, comprising administering to said mammal an antiviral effective amount of a compound of Formula I above, and one or more pharmaceutically acceptable carriers, excipients or diluents. Optionally, the compound of Formula I can be administered in combination with an antiviral effective amount of an AIDS treatment agent selected from the group consisting of: (a) an AIDS antiviral agent; (b) an anti-infective agent; (c) an immunomodulator; and (d) other HIV entry inhibitors.

Another embodiment of the present invention is a pharmaceutical composition comprising an antiviral effective amount of a compound of Formula I and one or more pharmaceutically acceptable carriers, excipients, diluents and optionally in combination with an antiviral effective amount of an AIDS treatment agent selected from the group consisting of: (a) an AIDS antiviral agent; (b) an anti-infective agent; (c) an immunomodulator; and (d) other HIV entry inhibitors.

In another embodiment of the invention there is provided one or more methods for making the compounds of Formula I.

The present invention is directed to these, as well as other important ends, hereinafter described.

DETAILED DESCRIPTION OF THE EMBODIMENTS

Since the compounds of the present invention may possess asymmetric centers and therefore occur as mixtures of diastereomers and enantiomers, the present disclosure includes the individual diastereoisomeric and enantiomeric forms of the compounds of Formula I in addition to the mixtures thereof.

Definitions

Unless otherwise specifically set forth elsewhere in the application, one or more of the following terms may be used herein, and shall have the following meanings:

The term "H" refers to hydrogen, including its isotopes such as deuterium.

The term "$C_{1-6}$ alkyl" as used herein and in the claims (unless specified otherwise) mean straight or branched chain alkyl groups such as methyl, ethyl, propyl, isopropyl, butyl, isobutyl, t-butyl, amyl, hexyl and the like.

"$C_1$-$C_4$ fluoroalkyl" refers to F-substituted $C_1$-$C_4$ alkyl wherein at least one H atom is substituted with F atom, and each H atom can be independently substituted by F atom.

"Halogen" refers to chlorine, bromine, iodine or fluorine.

An "aryl" or "Ar" group refers to an all carbon monocyclic or fused-ring polycyclic (i.e., rings which share adjacent pairs of carbon atoms) groups having a completely conjugated pi-electron system. Examples, without limitation, of aryl groups are phenyl, napthalenyl and anthracenyl. The aryl group may be substituted or unsubstituted. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino and —$NR^xR^y$, wherein $R^x$ and $R^y$ are independently selected from the group consisting of hydrogen, alkyl, cycloalkyl, aryl, carbonyl, C-carboxy, sulfonyl, trihalomethyl, and, combined, a five- or six-member heteroalicyclic ring.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Unless otherwise indicated, the heteroaryl group may be attached at either a carbon or nitrogen atom within the heteroaryl group. It should be noted that the term heteroaryl is intended to encompass an N-oxide of the parent heteroaryl if such an N-oxide is chemically feasible as is known in the art. Examples, without limitation, of heteroaryl groups are furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, pyrazinyl, diazinyl, pyrazine, triazinyl, tetrazinyl, and tetrazolyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thioalkoxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino, and —$NR^xR^y$, wherein $R^x$ and $R^y$ are as defined above.

As used herein, a "heteroalicyclic" group refers to a monocyclic or fused ring group having in the ring(s) one or more atoms selected from the group consisting of nitrogen, oxygen and sulfur. Rings are selected from those which provide stable arrangements of bonds and are not intended to encompass systems which would not exist. The rings may also have one or more double bonds. However, the rings do not have a completely conjugated pi-electron system. Examples, without limitation, of heteroalicyclic groups are azetidinyl, piperidyl, piperazinyl, imidazolinyl, thiazolidinyl, 3-pyrrolidin-1-yl, morpholinyl, thiomorpholinyl and tetrahydropyranyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —$NR^xR^y$, wherein $R^x$ and $R^y$ are as defined above.

An "alkyl" group refers to a saturated aliphatic hydrocarbon including straight chain and branched chain groups. Preferably, the alkyl group has 1 to 20 carbon atoms (whenever a numerical range; e.g., "1-20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from trihaloalkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, and combined, a five- or six-member heteroalicyclic ring.

A "cycloalkyl" group refers to an all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclopentene, cyclohexane, cyclohexene, cycloheptane, cycloheptene and adamantane. A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —$NR^xR^y$ with $R^x$ and $R^y$ as defined above.

An "alkenyl" group refers to an alkyl group, as defined herein, having at least two carbon atoms and at least one carbon-carbon double bond.

An "alkynyl" group refers to an alkyl group, as defined herein, having at least two carbon atoms and at least one carbon-carbon triple bond.

A "hydroxy" group refers to an —OH group.

An "alkoxy" group refers to both an —O-alkyl and an —O-cycloalkyl group as defined herein.

An "aryloxy" group refers to both an —O-aryl and an —O-heteroaryl group, as defined herein.

A "heteroaryloxy" group refers to a heteroaryl-O— group with heteroaryl as defined herein.

A "heteroalicycloxy" group refers to a heteroalicyclic-O— group with heteroalicyclic as defined herein.

A "thiohydroxy" group refers to an —SH group.

A "thioalkoxy" group refers to both an S-alkyl and an —S-cycloalkyl group, as defined herein.

A "thioaryloxy" group refers to both an —S-aryl and an —S-heteroaryl group, as defined herein.

A "thioheteroaryloxy" group refers to a heteroaryl-S— group with heteroaryl as defined herein.

A "thioheteroalicycloxy" group refers to a heteroalicyclic-S— group with heteroalicyclic as defined herein.

A "carbonyl" group refers to a —C(=O)—R" group, where R" is selected from the group consisting of hydrogen, alkyl, alkenyl, alkynyl, cycloalkyl, aryl, heteroaryl (bonded through a ring carbon) and heteroalicyclic (bonded through a ring carbon), as each is defined herein.

An "aldehyde" group refers to a carbonyl group where R" is hydrogen.

A "thiocarbonyl" group refers to a —C(=S)—R" group, with R" as defined herein.

A "Keto" group refers to a —CC(=O)C— group wherein the carbon on either or both sides of the C=O may be alkyl, cycloalkyl, aryl or a carbon of a heteroaryl or heteroalicyclic group.

A "trihalomethanecarbonyl" group refers to a $Z_3$CC(=O)— group with said Z being a halogen.

A "C-carboxy" group refers to a —C(=O)O—R" groups, with R" as defined herein.

An "O-carboxy" group refers to a R"C(=O)O-group, with R" as defined herein.

A "carboxylic acid" group refers to a C-carboxy group in which R" is hydrogen.

A "trihalomethyl" group refers to a —$CZ_3$, group wherein Z is a halogen group as defined herein.

A "trihalomethanesulfonyl" group refers to an $Z_3$CS(=O)$_2$— groups with Z as defined above.

A "trihalomethanesulfonamido" group refers to a $Z_3$CS(=O)$_2$NR$^x$— group with Z as defined above and $R^x$ being H or ($C_{1-6}$)alkyl.

A "sulfinyl" group refers to a —S(=O)—R" group, with R" being ($C_{1-6}$)alkyl.

A "sulfonyl" group refers to a —S(=O)$_2$R" group with R" being ($C_{1-6}$)alkyl.

A "S-sulfonamido" group refers to a —S(=O)$_2$NR$^X$R$^Y$, with $R^X$ and $R^Y$ independently being H or ($C_{1-6}$)alkyl.

A "N-Sulfonamido" group refers to a R"S(=O)$_2$NR$_X$— group, with $R_x$ being H or ($C_{1-6}$)alkyl.

A "O-carbamyl" group refers to a —OC(=O)NR$^x$R$^y$ group, with $R^X$ and $R^Y$ independently being H or ($C_{1-6}$)alkyl.

A "N-carbamyl" group refers to a R$^x$OC(=O)NR$^y$ group, with $R^x$ and $R^y$ independently being H or ($C_{1-6}$)alkyl.

A "O-thiocarbamyl" group refers to a —OC(=S)NR$^x$R$^y$ group, with $R^x$ and $R^y$ independently being H or ($C_{1-6}$)alkyl.

A "N-thiocarbamyl" group refers to a R$^x$OC(=S)NR$^y$— group, with $R^x$ and $R^y$ independently being H or ($C_{1-6}$)alkyl.

An "amino" group refers to an —$NH_2$ group.

A "C-amido" group refers to a —C(=O)NR$^x$R$^y$ group, with $R^x$ and $R^y$ independently being H or ($C_{1-6}$)alkyl.

A "C-thioamido" group refers to a —C(=S)NR$^x$R$^y$ group, with $R^x$ and $R^y$ independently being H or ($C_{1-6}$)alkyl.

A "N-amido" group refers to a R$^x$C(=O)NR$^y$— group, with $R^x$ and $R^y$ independently being H or ($C_{1-6}$)alkyl.

An "ureido" group refers to a —NR$^x$C(=O)NR$^y$R$^{y2}$ group, with $R^x$, $R^y$, and $R^{y2}$ independently being H or ($C_{1-6}$)alkyl.

A "guanidino" group refers to a —R$^x$NC(=N)NR$^y$R$^{y2}$ group, with $R^x$, $R^y$, and $R^{y2}$ independently being H or ($C_{1-6}$)alkyl.

A "guanyl" group refers to a R$^x$R$^y$NC(=N)— group, with $R^x$ and $R^y$ independently being H or ($C_{1-6}$)alkyl.

A "cyano" group refers to a —CN group.

A "silyl" group refers to a —Si(R")$_3$, with R" being ($C_{1-6}$) alkyl or phenyl.

A "phosphonyl" group refers to a P(=O)(OR$^x$)$_2$ with $R^x$ being ($C_{1-6}$)alkyl.

A "hydrazino" group refers to a —NR$^x$NR$^y$R$^{y2}$ group, with $R^x$, $R^y$, and $R^{y2}$ independently being H or ($C_{1-6}$)alkyl.

A "4, 5, or 6 membered ring cyclic N-lactam" group refers to

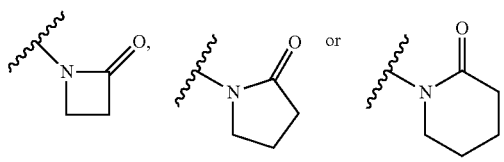

Any two adjacent R groups may combine to form an additional aryl, cycloalkyl, heteroaryl or heterocyclic ring fused to the ring initially bearing those R groups.

It is known in the art that nitrogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present disclosure are based on the known general principles of chemical bonding. It is understood that the claims do not encompass structures known to be unstable or not able to exist based on the literature.

Pharmaceutically acceptable salts and prodrugs of compounds disclosed herein are within the scope of this disclosure. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfuric acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g., hydroxyl-substituted alkylamines such as diethanolamine, triethanolamine or tris(hydroxymethyl)-aminomethane), or with bases such as piperidine or morpholine.

As stated above, the compounds of the invention also include "prodrugs". The term "prodrug" as used herein encompasses both the term "prodrug esters" and the term "prodrug ethers". The term "prodrug esters" as employed herein includes esters and carbonates formed by reacting one or more hydroxyls of compounds of Formula I with either alkyl, alkoxy, or aryl substituted acylating agents or phosphorylating agent employing procedures known to those skilled in the art to generate acetates, pivalates, methylcarbonates, benzoates, amino acid esters, phosphates, half acid esters such as malonates, succinates or glutarates, and the like. In certain embodiments, amino acid esters may be especially preferred.

Examples of such prodrug esters include

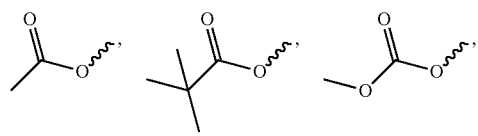

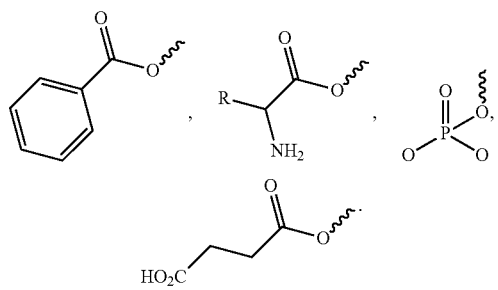

The term "prodrug ethers" include both phosphate acetals and O-glucosides. Representative examples of such prodrug ethers include

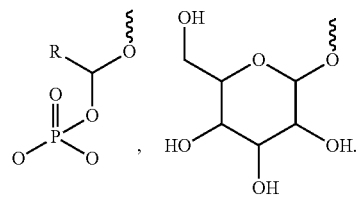

Prodrug derivatives in which the prodrug moiety is attached to the indole N atom are also considered part of this invention. These prodrugs can be prepared by substitution of the indole N with a moiety that modifies the physical properties of the compound and can be unmasked either by chemical or enzymatic degradation. Examples of $R_3$ include acyl derivatives similar to those described above. A preferred prodrug is the phosphonoxymethyl moiety which can be introduced using methods previously described and converted to pharmaceutically acceptable salt forms that confer chemical stability and advantageous physical properties:

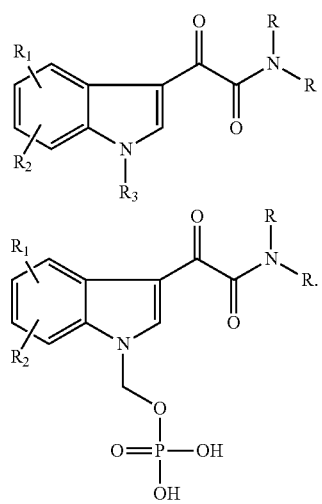

As set forth above, the invention is directed to compounds of Formula I, including pharmaceutically acceptable salts thereof:

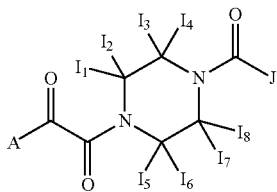

I wherein A is selected from the group consisting of:

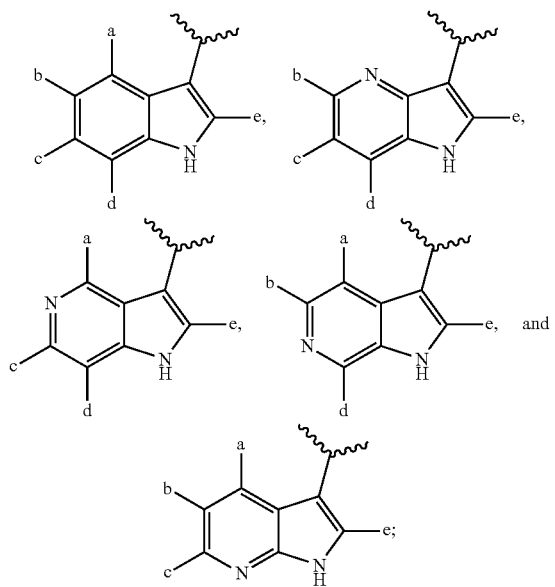

wherein
a, b, c, d and e are independently selected from the group consisting of hydrogen, halogen, cyano, nitro, $COOR^{56}$, $XR^{57}$, $NA^1A^2$, $C(O)R^7$, $C(O)NR^{55}R^{56}$, B, Q, and E;
B is selected from the group consisting of —C(=$NR^{46}$)($R^{47}$), $C(O)NR^{40}R^{41}$, aryl, heteroaryl, heteroalicyclic, $S(O)_2R^8$, $C(O)R^7$, $XR^{8a}$, $(C_{1-6})$alkyl$NR^{40}R^{41}$, $(C_{1-6})$alkyl$COOR^{8b}$; wherein said aryl, heteroaryl, and heteroalicyclic are optionally substituted with one to three same or different halogens or from one to three same or different substituents selected from the group F; wherein aryl is napthyl or substituted phenyl; wherein heteroaryl is a mono or bicyclic system which contains from 3 to 7 ring atoms for a mono cyclic system and up to 12 atoms in a fused bicyclic system, including from 1 to 4 heteroatoms; wherein heteroalicyclic is a 3 to 7 membered mono cyclic ring which may contain from 1 to 2 heteroatoms in the ring skeleton and which may be fused to a benzene or pyridine ring;
Q is selected from the group consisting of $(C_{1-6})$alkyl and $(C_{2-6})$alkenyl; wherein said $(C_{1-6})$alkyl and $(C_{2-6})$alkenyl are optionally substituted with one to three same or different halogens or from one to three same or different substituents selected from the group consisting of $C(O)NR^{55}R^{56}$, hydroxy, cyano and $XR^{57}$;
E is selected from the group consisting of $(C_{1-6})$alkyl and $(C_{2-6})$alkenyl; wherein said $(C_{1-6})$alkyl and $(C_{2-6})$alkenyl are independently optionally substituted with a member selected from the group consisting of phenyl, heteroaryl, SMe, SPh, —$C(O)NR_{56}R_{57}$, $C(O)R_{57}$, $SO_2(C_{1-6})$alkyl and $SO_2Ph$; wherein heteroaryl is a monocyclic system which contains from 3 to 7 ring atoms, including from 1 to 4 heteroatoms;

$R^7$ is selected from the group consisting of aryl, heteroaryl, and heteroalicyclic; wherein said aryl, heteroaryl, and heteroalicyclic are optionally substituted with one to three same or different halogens or with from one to three same or different substituents selected from the group F;
wherein for $R^7$, $R^8$, $R^{8a}$, $R^{8b}$ aryl is phenyl; heteroaryl is a mono or bicyclic system which contains from 3 to 7 ring atoms for mono cyclic systems and up to 10 atoms in a bicyclic system, including from 1 to 4 heteroatoms; wherein heteroalicyclic is selected from the group consisting of aziridine, azetidine, pyrrolidine, piperazine, piperidine, tetrahydrofuran, tetrahydropyran, azepine, and morpholine;
F is selected from the group consisting of $(C_{1-6})$alkyl, $(C_{3-7})$cycloalkyl, aryl, heteroaryl, heteroalicyclic, hydroxy, $(C_{1-6})$alkoxy, aryloxy, $(C_{1-6})$thioalkoxy, cyano, halogen, nitro, —$C(O)R^{57}$, benzyl, —$NR^{42}C(O)$—$(C_{1-6})$alkyl, —$NR^{42}C(O)$—$(C_{3-6})$cycloalkyl, —$NR^{42}C(O)$-aryl, —$NR^{42}C(O)$-heteroaryl, —$NR^{42}C(O)$-heteroalicyclic, a 4, 5, or 6 membered ring cyclic N-lactam, —$NR^{42}S(O)_2$—$(C_{1-6})$alkyl, —$NR^{42}S(O)_2$—$(C_{3-6})$cycloalkyl, —$NR^{42}S(O)2$-aryl, —$NR^{42}S(O)_2$-heteroaryl, —$NR^{42}S(O)2$-heteroalicyclic, $S(O)_2(C_{1-6})$alkyl, $S(O)_2$aryl, —$S(O)2$ $NR^{42}R^{43}$, $NR^{42}R^{43}$, $(C_{1-6})$alkylC(O)$NR^{42}R^{43}$, $C(O)NR^{42}R^{43}$, $NHC(O)NR^{42}R^{43}$, $OC(O)NR^{42}R^{43}$, $NHC(O)OR^{54}$, $(C_{1-6})$alkyl$NR^{42}R^{43}$, $COOR^{54}$, and $(C_{1-6})$alkyl$COOR^{54}$; wherein said $(C_{1-6})$alkyl, $(C_{3-7})$cycloalkyl, aryl, heteroaryl, heteroalicyclic, $(C_{1-6})$alkoxy, and aryloxy, are optionally substituted with one to nine same or different halogens or from one to five same or different substituents selected from the group G; wherein aryl is phenyl; heteroaryl is a monocyclic system which contains from 3 to 7 ring atoms, including from 1 to 4 heteroatoms; heteroalicyclic is selected from the group consisting of aziridine, azetidine, pyrrolidine, piperazine, piperidine, tetrahydrofuran, tetrahydropyran, azepine, and morpholine;
$R^8$ is selected from the group consisting of hydrogen, $(C_{1-6})$alkyl, $(C_{3-7})$cycloalkyl, $(C_{2-6})$alkenyl, $(C_{3-7})$cycloalkenyl, $(C_{2-6})$alkynyl, aryl, heteroaryl, and heteroalicyclic; wherein said $(C_{1-6})$alkyl, $(C_{3-7})$cycloalkyl, $(C_{2-6})$alkenyl, $(C_{3-7})$cycloalkenyl, $(C_{2-6})$alkynyl, aryl, heteroaryl, and heteroalicyclic are optionally substituted with one to six same or different halogens or from one to five same or different substituents selected from the group F or $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, acyl sulfamide, sulfate, sulfuric acid, sulfamic acid, phosphate, phosphoric acid, boronic ester, boronic acid, squarate, squaric acid, oxime, hydrazine, peroxide, among which ether, peroxide, thioether, secondary amine, tertiary amine, ammonium, ester, ketone, amide, amidine, oxime, hydrazine can be either acyclic or cyclic; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl;
$R^{8a}$ is a member selected from the group consisting of aryl, heteroaryl, and heteroalicyclic; wherein each member is independently optionally substituted with one to six same or different halogens or from one to five same or different substituents selected from the group F;
$R^{8b}$ is selected from the group consisting of hydrogen, $(C_{1-6})$ alkyl and phenyl;
X is selected from the group consisting of NH or $NCH_3$, O, and S;
$R^{40}$ and $R^{41}$ are independently selected from the group consisting of (a) hydrogen; (b) $(C_{1-6})$alkyl or $(C_{3-7})$cycloalkyl substituted with one to three same or different halogens or from one to two same or different substituents selected from the group F or different functional groups: $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, acyl sulfamide, sulfate, sulfuric acid, sulfamic acid, phosphate, phosphoric acid, boronic ester, boronic acid, squarate, squaric acid, oxime, hydrazine, peroxide, among which ether, peroxide, thioether, secondary amine, tertiary amine, ammonium, ester, ketone, amide, amidine, oxime, hydrazine can be either acyclic or cyclic; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl; and (c) $(C_{1-6})$alkoxy, aryl, heteroaryl or heteroalicyclic; or $R^{40}$ and $R^{41}$ taken together with the nitrogen to which they are attached form a member selected from the group consisting of aziridine, azetidine, pyrrolidine, piperazine, 4-NMe piperazine, piperidine, azepine, and morpholine; and wherein said aryl, heteroaryl, and heteroalicyclic are optionally substituted with one to three same or different halogens or from one to two same or different substituents selected from the group F; wherein for $R^{40}$ and $R^{41}$ aryl is phenyl; heteroaryl is a monocyclic system which contains from 3 to 6 ring atoms, including from 1 to 4 heteroatoms; heteroalicyclic is selected from the group consisting of aziridine, azetidine, pyrrolidine, piperazine, piperidine, tetrahydrofuran, tetrahydropyran, azepine, and morpholine; provided when B is $C(O)NR^{40}R^{41}$, at least one of $R^{40}$ and $R^{41}$ is not selected from groups (a) or (b);

$R^{42}$ and $R^{43}$ are independently selected from the group consisting of hydrogen, $(C_{1-6})$alkyl, allyl, $(C_{1-6})$alkoxy, $(C_{3-7})$cycloalkyl, aryl, heteroaryl and heteroalicyclic; or $R^{42}$ and $R^{43}$ taken together with the nitrogen to which they are attached form a member selected from the group consisting of aziridine, azetidine, pyrrolidine, piperazine, 4-NMe piperazine, piperidine, azepine, and morpholine; and wherein said $(C_{1-6})$alkyl, $(C_{1-6})$alkoxy, $(C_{3-7})$cycloalkyl, aryl, heteroaryl, and heteroalicyclic are optionally substituted with one to three same or different halogens or from one to two same or different substituents selected from the group G or different functional groups: $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, acyl sulfamide, sulfate, sulfuric acid, phosphate, phosphoric acid, boronic ester, boronic acid, squarate, squaric acid, oxime, hydrazine, peroxide, among which ether, peroxide, thioether, secondary amine, tertiary amine, ammonium, ester, ketone, amide, amidine, oxime, hydrazine can be either acyclic or cyclic; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl; wherein for $R^{42}$ and $R^{43}$ aryl is phenyl; heteroaryl is a monocyclic system which contains from 3 to 6 ring atoms, including from 1 to 4 heteroatoms; heteroalicyclic is a member selected from the group consisting of aziridine, azetidine, pyrrolidine, piperazine, piperidine, tetrahydrofuran, tetrahydropyran, azepine, and morpholine;

G is selected from the group consisting of $(C_{1-6})$alkyl, $(C_{3-7})$cycloalkyl, aryl, heteroaryl, heteroalicyclic, hydroxy, $(C_{1-6})$alkoxy, aryloxy, cyano, halogen, nitro, —$C(O)R^{57}$, benzyl, —$NR^{48}C(O)$—$(C_{1-6})$alkyl, —$NR^{48}C(O)$—$(C_{3-6})$cycloalkyl, —$NR^{48}C(O)$-aryl, —$NR^{48}C(O)$-heteroaryl, —$NR^{48}C(O)$-heteroalicyclic, a 4, 5, or 6 membered ring cyclic N-lactam, —$NR^{48}S(O)_2$—$(C_{1-6})$alkyl, —$NR^{48}S(O)_2$—$(C_{3-6})$cycloalkyl, —$NR^{48}S(O)2$-aryl, —$NR^{48}S(O)_2$-heteroaryl, —$NR^{48}S(O)2$-heteroalicyclic, sulfinyl, sulfonyl, sulfonamide, $NR^{48}R^{49}$, $(C_{1-6})$alkyl $C(O)NR^{48}R^{49}$, $C(O)NR^{48}R^{49}$, $NHC(O)NR^{48}R^{49}$, $OC(O)NR^{48}R^{49}$, $NHC(O)OR^{54}$, $(C_{1-6})$alkyl$NR^{48}R^{49}$, $COOR^{54}$, and $(C_{1-6})$alkyl$COOR^{54}$; wherein aryl is phenyl; heteroaryl is a monocyclic system which contains from 3 to 7 ring atoms, including from 1 to 4 heteroatoms; heteroalicyclic is selected from the group consisting of aziridine, azetidine, pyrrolidine, piperazine, piperidine, tetrahydrofuran, tetrahydropyran, azepine, and morpholine;

$R^{46}$ is selected from the group consisting of H, $OR^{57}$, and $NR^{55}R^{56}$;

$R^{47}$ is selected from the group consisting of H, amino, halogen, phenyl, aryl, heteroaryl and $(C_{1-6})$alkyl;

$R^{48}$ and $R^{49}$ are independently selected from the group consisting of hydrogen, $(C_{1-6})$alkyl, phenyl, aryl and heteroaryl;

$R^{50}$ is selected from the group consisting of H, $(C_{1-6})$alkyl, $(C_{3-6})$cycloalkyl, and benzyl; wherein each of said $(C_{1-6})$alkyl, $(C_{3-7})$cycloalkyl and benzyl are optionally substituted with one to three same or different $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, acyl sulfamide, sulfate, sulfuric acid, sulfamic acid, phosphate, phosphoric acid, boronic ester, boronic acid, squarate, squaric acid, oxime, hydrazine, peroxide, among which ether, peroxide, thioether, secondary amine, tertiary amine, ammonium, ester, ketone, amide, amidine, oxime, hydrazine can be either acyclic or cyclic; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl $R^{54}$ is selected from the group consisting of hydrogen and $(C_{1-6})$alkyl;

$R^{54'}$ is $(C_{1-6})$alkyl;

$R^{55}$ and $R^{56}$ are independently selected from the group consisting of hydrogen and $(C_{1-6})$alkyl; and $R^{57}$ is selected from the group consisting of hydrogen, $(C_{1-6})$alkyl, aryl, heteroaryl; and $A^1$ and $A^2$ are independently selected from hydrogen, $(C_{1-6})$alkyl, aryl, heteroaryl, $SO2D^1$, $SO2ND^2D^3$, $COD^4$, $COCOD^4$, $COOD^4$, $COND^5D^6$, $COCOND^5D^6$, $COCOOD^4$, $C(=ND^7)D^8$, $C(=ND^9)ND^{10}D^{11}$;

$A^1$ and $A^2$ can either never connect with each other, or conjoin to form a ring structure;

$D^1$, $D^2$, $D^3$, $D^4$, $D^5$, $D^6$, $D^7$, $D^8$, $D^9$, $D^{10}$, and $D^{11}$ are each independently selected from the group consisting of H, $C_1$-$C_{50}$ alkyl, $C_3$-$C_{50}$ cycloalkyl, $C_3$-$C_{50}$ alkenyl, $C_4$-$C_{50}$ cycloalkenyl, phenyl, heteroaryl, $C_3$-$C_{50}$ amide and $C_3$-$C_{50}$ ether; heteroaryl is selected from the group consisting of pyridinyl, pyrazinyl, pyridazinyl, pyrimidinyl, furanyl, thienyl, benzothienyl, thiazolyl, isothiazolyl, oxazolyl, benzooxazolyl, isoxazolyl, imidazolyl, benzoimidazolyl, 1H-imidazo[4,5-b]pyridin-2-yl, 1H-imidazo[4,5-c]pyridin-2-yl, oxadiazolyl, thiadiazolyl, pyrazolyl, tetrazolyl, tetrazinyl, triazinyl and triazolyl; provided the carbon atoms which comprise the carbon-carbon double bond of said $C_3$-$C_{20}$ alkenyl or the carbon-carbon triple bond of said $C_3$-$C_{20}$ alkynyl are not the point of attachment to the nitrogen to which $D^2$, $D^3$, $D^5$, $D^6$, $D^7$, $D^9$, $D^{10}$, and $D^{11}$ is attached; wherein said $C_1$-$C_{50}$ alkyl, $C_3$-$C_{50}$ cycloalkyl, $C_3$-$C_{50}$ alkenyl, $C_4$-$C_{50}$ cycloalkenyl, aryl, phenyl, heteroaryl, $C_3$-$C_{50}$ amide and $C_3$-$C_{50}$ ether is optionally substituted with one to three same or different of the following functionalities: $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, acyl sulfamide, sulfate, sulfuric acid, sulfamic acid, phosphate, phosphoric acid, boronic ester, boronic acid, squarate, squaric acid, oxime, hydrazine, peroxide, among which ether, peroxide, thioether, secondary amine, tertiary amine, ammonium, ester, ketone, amide, amidine, oxime, hydrazine can be either acyclic or cyclic;

$I_1$, $I_2$, $I_3$, $I_4$, $I_5$, $I_6$, $I_7$ and $I_8$ are each independently selected from the group consisting of H, $(C_{1-6})$alkyl, $(C_{3-6})$cycloalkyl, $(C_{2-6})$alkenyl, $(C_{4-6})$cycloalkenyl, $(C_{2-6})$alkynyl, $CR_{81}R_{82}OR_{83}$, $COR_{84}$, $COOR_{85}$, or $CONR_{86}R_{87}$; wherein each of said alkyl and cycloalkyl being optionally substituted with one to three same or different cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, acyl sulfamide, sulfate, sulfuric acid, sulfamic acid, phosphate, phosphoric acid, boronic ester, boronic acid, squarate, squaric acid, oxime, hydrazine, peroxide, among which ether, peroxide, thioether, secondary amine, tertiary amine, ammonium, ester, ketone, amide, amidine, oxime, hydrazine can be either acyclic or cyclic; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl;

J is selected from the group consisting of H, $C_1$-$C_{30}$ alkyl, $C_3$-$C_{15}$ cycloalkyl, $C_4$-$C_{30}$ bicycloalkyl, $C_5$-$C_{30}$ tricycloalkyl, $C_6$-$C_{30}$ tetracycloalkyl, $C_3$-$C_{30}$ alkenyl, $C_4$-$C_{30}$ cycloalkenyl, $C_5$-$C_{30}$ bicycloalkenyl, $C_2$-$C_{30}$ tricycloalkenyl, $C_9$-$C_{30}$ tetracycloalkyl, $C_1$-$C_{30}$ amide, $C_3$-$C_{30}$ cyclic amide, $C_1$-$C_{30}$ amine, $C_3$-$C_{30}$ cyclic amine, $C_2$-$C_{30}$ ester, $C_3$-$C_{30}$ cyclic ester, $C_2$-$C_{30}$ ether, $C_3$-$C_{30}$ cyclic ether, $C_1$-$C_{30}$ sulfonamide, $C_3$-$C_{30}$ cyclic sulfonamide, $C_2$-$C_{30}$ sulfone, $C_3$-$C_{30}$ cyclic sulfone, $C_2$-$C_{30}$ urea, and $C_3$-$C_{30}$ cyclic urea; wherein said $C_1$-$C_{30}$ alkyl, $C_3$-$C_{30}$ cycloalkyl, $C_4$-$C_{30}$ bicycloalkyl, $C_5$-$C_{30}$ tricycloalkyl, $C_6$-$C_{30}$ tetracycloalkyl, $C_3$-$C_{30}$ alkenyl, $C_4$-$C_{30}$ cycloalkenyl, $C_5$-$C_{30}$ bicycloalkenyl, $C_7$-$C_{30}$ tricycloalkenyl, $C_9$-$C_{30}$ tetracycloalkyl, $C_1$-$C_{30}$ amide, $C_3$-$C_{30}$ cyclic amide, $C_1$-$C_{30}$ amine, $C_3$-$C_{30}$ cyclic amine, $C_2$-$C_{30}$ ester, $C_3$-$C_{30}$ cyclic ester, $C_2$-$C_{30}$ ether, $C_3$-$C_{30}$ cyclic ether, $C_1$-$C_{30}$ sulfonamide, $C_3$-$C_{30}$ cyclic sulfonamide, $C_2$-$C_{30}$ sulfone, $C_3$-$C_{30}$ cyclic sulfone, $C_2$-$C_{30}$ urea, and $C_3$-$C_{30}$ cyclic urea is optionally substituted with one to three same or different of the following functionalities: $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, acyl sulfamide, sulfate, sulfuric acid, sulfamic acid, phosphate, phosphoric acid, boronic ester, boronic acid, squarate, squaric acid, oxime, hydrazine, peroxide, among which ether, peroxide, thioether, secondary amine, tertiary amine, ammonium, ester, ketone, amide, amidine, oxime, hydrazine can be either acyclic or cyclic; and $R_{81}$, $R_{82}$, $R_{83}$, $R_{84}$, $R_{85}$, $R_{86}$, and $R_{87}$ are each independently selected from the group consisting of H, $(C_{1-6})$alkyl, $(C_{3-6})$cycloalkyl, $(C_{2-6})$alkenyl, $(C_{4-6})$cycloalkenyl, and $(C_{2-6})$alkynyl.

In a further embodiment of the compounds of Formula I above, there is the proviso that at least one of a-e is selected from group B or group E.

In a further embodiment, it is preferred that A be selected from the group consisting of:

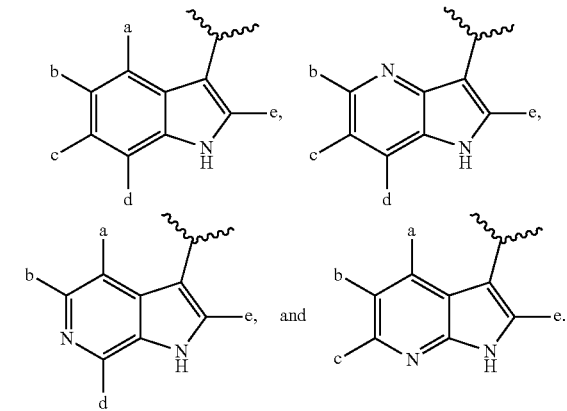

In another embodiment, it is preferred that B is selected from the group consisting of $C(O)NR^{40}R^{41}$, aryl, heteroaryl, and $XR^{8a}$.

In another embodiment, it is preferred that Q is $(C_{1-6})$alkyl.

In a further embodiment, it is preferred that E is $(C_{2-6})$alkenyl; optionally substituted with a member selected from the group consisting of phenyl, heteroaryl, —$C(O)NR^{56}R^{57}$, and —$C(O)R^{57}$.

In another embodiment, it is preferred that $R^7$ is selected from the group of phenyl, pyridinyl, pyrazinyl, pyridazinyl, pyrimidinyl, thiazolyl, isothiazolyl, oxazolyl, isoxazolyl, imidazolyl, oxadiazolyl, thiadiazolyl, pyrazolyl, tetrazolyl, triazinyl and triazolyl; wherein said phenyl, pyridinyl, pyrazinyl, pyridazinyl, pyrimidinyl, thiazolyl, isothiazolyl, oxazolyl, isoxazolyl, imidazolyl, oxadiazolyl, thiadiazolyl, pyrazolyl, tetrazolyl, triazinyl and triazolyl are optionally substituted with one to three same or different halogens or with from one to three same or different substituents selected from the group F.

In another embodiment, it is preferred that F is selected from the group consisting of $(C_{1-6})$alkyl, $(C_{3-7})$cycloalkyl, hydroxy, $(C_{1-6})$alkoxy, cyano, halogen, —$NR^{42}C(O)$—$(C_{1-6})$alkyl, —$NR^{42}C(O)$—$(C_{3-6})$cycloalkyl, a 4, 5, or 6 membered ring cyclic N-lactam, —$NR^{42}S(O)_2$—$(C_{1-6})$alkyl, —$NR^{42}S(O)_2$—$(C_{3-6})$cycloalkyl, $S(O)_2(C_{1-6})$alkyl, —$S(O)2NR^{42}R^{43}$, $NR^{42}R^{43}$, $(C_{1-6})$alkyl$C(O)NR^{42}R^{43}$, $C(O)NR^{42}R^{43}$, $NHC(O)NR^{42}R^{43}$, $OC(O)NR^{42}R^{43}$, $NHC(O)OR^{54}$, $(C_{1-6})$alkyl$NR^{42}R^{43}$, $COOR^{54}$, and $(C_{1-6})$alkyl-$COOR^{54}$.

In another embodiment, it is preferred that X be NH, $NCH_3$, or O.

In another embodiment, it is preferred that $R^{40}$ and $R^{41}$ be selected from the group of (a) hydrogen; (b) $(C_{1-6})$alkyl or $(C_{3-7})$cycloalkyl substituted with one to three same or different halogens or from one to two same or different substituents selected from the group F or different functional groups: $(C_{1-6})$alkyl, $(C_{3-6})$cycloalkyl, phenyl, aryl, heteroaryl, heteroalicyclic, hydroxy, $(C_{1-6})$alkoxy, halogen, primary amine, secondary amine, tertiary amine, ammonium, alcohol, ether, acid, ketone, amide, amidine, guanidine, sulfone, sulfonamide, sulfamide, acyl sulfamide, sulfate, sulfuric acid, sulfamic acid, phosphate, phosphoric acid, boronic ester, boronic acid, squarate, squaric acid, oxime, hydrazine, among which ether, secondary amine, tertiary amine, ammonium, ester, ketone, amide, amidine, oxime, hydrazine can be either acyclic or cyclic; heteroaryl is selected from the group consisting of thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl; and (c) $(C_{1-6})$alkoxy, aryl, heteroaryl or heteroalicyclic; or $R^{40}$ and $R^{41}$ taken together with the nitrogen to which they are attached form a member selected from the group consisting of azetidine, pyrrolidine, piperazine, 4-NMe piperazine, piperidine, azepine, and morpholine; and wherein said aryl, heteroaryl, and heteroalicyclic are optionally substituted with one to three same or different halogens or from one to two same or different substituents selected from the group F; wherein for $R^{40}$ and $R^{41}$ aryl is phenyl; heteroaryl is a monocyclic system which contains from 3 to 6 ring atoms, including from 1 to 4 heteroatoms; heteroalicyclic is selected from the group consisting of azetidine, pyrrolidine, piperazine, piperidine, tetrahydrofuran, tetrahydropyran, azepine, and morpholine; provided when B is $C(O)NR^{40}R^{41}$, at least one of $R^{40}$ and $R^{41}$ is not selected from groups (a) or (b).

In a further embodiment, it is preferred that $R^{42}$ and $R^{43}$ be selected from the group of hydrogen, $(C_{1-6})$alkyl, a $(C_{1-6})$alkoxy, $(C_{3-7})$cycloalkyl, aryl, heteroaryl and heteroalicyclic; or $R^{42}$ and $R^{43}$ taken together with the nitrogen to which they are attached form a member selected from the group consisting of azetidine, pyrrolidine, piperazine, 4-NMe piperazine, piperidine, azepine, and morpholine; and wherein said $(C_{1-6})$alkyl, $(C_{1-6})$alkoxy, $(C_{3-7})$cycloalkyl, aryl, heteroaryl, and heteroalicyclic are optionally substituted with one to three same or different halogens or from one to two same or different substituents selected from the group G or different functional groups: $(C_{1-6})$alkyl, $(C_{3-6})$cycloalkyl, phenyl, aryl, heteroaryl, heteroalicyclic, hydroxy, $(C_{1-6})$alkoxy, halogen, benzyl, primary amine, secondary amine, tertiary amine, ammonium, alcohol, ether, acid, ketone, amide, amidine, guanidine, sulfone, sulfonamide, sulfamide, acyl sulfamide, sulfate, sulfuric acid, sulfamic acid, phosphate, phosphoric acid, boronic ester, boronic acid, squarate, squaric acid, oxime, hydrazine, among which ether, secondary amine, tertiary amine, ammonium, ester, ketone, amide, amidine, oxime, hydrazine can be either acyclic or cyclic; heteroaryl is selected from the group consisting of thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl; wherein for $R^{42}$ and $R^{43}$ aryl is phenyl; heteroaryl is a monocyclic system which contains from 3 to 6 ring atoms, including from 1 to 4 heteroatoms; heteroalicyclic is a member selected from the group consisting of azetidine, pyrrolidine, piperazine, piperidine, tetrahydrofuran, tetrahydropyran, azepine, and morpholine.

In another embodiment, it is preferred that G is selected from the group consisting of $(C_{1-6})$alkyl, $(C_{3-7})$cycloalkyl, hydroxy, $(C_{1-6})$alkoxy, cyano, halogen, $-NR^{42}C(O)-$ $(C_{1-6})$alkyl, $-NR^{42}C(O)-(C_{3-6})$cycloalkyl, a 4, 5, or 6 membered ring cyclic N-lactam, $-NR^{42}S(O)_2-(C_{1-6})$alkyl, $-NR^{42}S(O)_2-(C_{3-6})$cycloalkyl, $S(O)_2(C_{1-6})$alkyl, $-S(O)2NR^{42}R^{43}$, $NR^{42}R^{43}$, $(C_{1-6})$alkylC(O)NR$^{42}$R$^{43}$, $C(O)$NR$^{42}$R$^{43}$, NHC(O)NR$^{42}$R$^{43}$, OC(O)NR$^{42}$R$^{43}$, NHC(O)OR$^{54}$, $(C_{1-6})$alkylNR$^{42}$R$^{43}$, COOR$^{54}$, and $(C_{1-6})$alkylCOOR$^{54}$.

In a further embodiment, it is preferred that $A^1$ and $A^2$ be selected from the group consisting of hydrogen, $(C_{1-6})$alkyl, aryl, heteroaryl, $COD^4$, $COCOD^4$, $COOD^4$, $COND^5D^6$, $COCOND^5D^6$, and $COCOOD^4$.

In another embodiment, it is preferred that $D^4$, $D^5$, and $D^6$ be selected from the group consisting of H, $C_1$-$C_{10}$ alkyl, $C_3$-$C_{10}$ cycloalkyl, $C_3$-$C_{10}$ alkenyl, $C_4$-$C_{10}$ cycloalkenyl, phenyl, heteroaryl, $C_3$-$C_{10}$ amide and $C_3$-$C_{10}$ ether; heteroaryl is selected from the group consisting of pyridinyl, pyrazinyl, pyridazinyl, pyrimidinyl, thiazolyl, isothiazolyl, oxazolyl, isoxazolyl, imidazolyl, oxadiazolyl, thiadiazolyl, pyrazolyl, tetrazolyl, triazinyl and triazolyl; provided the carbon atoms which comprise the carbon-carbon double bond of said $C_3$-$C_{10}$ alkenyl or the carbon-carbon triple bond of said $C_3$-$C_{10}$ alkynyl are not the point of attachment to the nitrogen to which $D^5$ and $D^6$ is attached; wherein said $C_1$-$C_{10}$ alkyl, $C_3$-$C_{10}$ cycloalkyl, $C_3$-$C_{10}$ alkenyl, $C_4$-$C_{10}$ cycloalkenyl, aryl, phenyl, heteroaryl, $C_3$-$C_{10}$ amide and $C_3$-$C_{10}$ ether is optionally substituted with one to three same or different of the following functionalities: $(C_{1-6})$alkyl, $(C_{3-6})$cycloalkyl, cyano, phenyl, aryl, heteroaryl, heteroalicyclic, hydroxy, $(C_{1-6})$alkoxy, halogen, primary amine, secondary amine, tertiary amine, ammonium, alcohol, ether, acid, ketone, amide, amidine, guanidine, sulfone, sulfonamide, sulfamide, acyl sulfamide, sulfate, sulfuric acid, sulfamic acid, phosphate, phosphoric acid, boronic ester, boronic acid, squarate, squaric acid, oxime, hydrazine, peroxide, among which ether, thioether, secondary amine, tertiary amine, ammonium, ester, ketone, amide, amidine, oxime, hydrazine can be either acyclic or cyclic.

In another embodiment, it is preferred that $I_1$, $I_2$, $I_3$, $I_4$, $I_5$, $I_6$, $I_7$ and $I_8$ are selected from the group of H, $(C_{1-6})$alkyl, $(C_{3-6})$cycloalkyl, $(C_{2-6})$alkenyl, $CR_{81}R_{82}OR_{83}$, $COR_{84}$, $COOR_{85}$, and $CONR_{86}R_{87}$.

In a further embodiment, it is preferred that J be selected from the group consisting of H, $C_1$-$C_{10}$ alkyl, $C_3$-$C_{10}$ cycloalkyl, $C_4$-$C_{15}$ bicycloalkyl, $C_5$-$C_{20}$ tricycloalkyl, $C_6$-$C_{25}$ tetracycloalkyl, $C_3$-$C_{10}$ alkenyl, $C_4$-$C_{10}$ cycloalkenyl, $C_5$-$C_{15}$ bicycloalkenyl, $C_7$-$C_{20}$ tricycloalkenyl, $C_9$-$C_{25}$ tetracycloalkyl, $C_1$-$C_{10}$ amide, $C_3$-$C_{10}$ cyclic amide, $C_1$-$C_{10}$ amine, $C_3$-$C_{10}$ cyclic amine, $C_2$-$C_{10}$ ester, $C_3$-$C_{10}$ cyclic ester, $C_2$-$C_{10}$ ether, $C_3$-$C_{10}$ cyclic ether, $C_1$-$C_{10}$ sulfonamide, $C_3$-$C_{10}$ cyclic sulfonamide, $C_2$-$C_{10}$ sulfone, $C_3$-$C_{10}$ cyclic sulfone, $C_2$-$C_{10}$ urea, and $C_3$-$C_{10}$ cyclic urea; wherein said H, $C_1$-$C_{10}$ alkyl, $C_3$-$C_{10}$ cycloalkyl, $C_4$-$C_{15}$ bicycloalkyl, $C_5$-$C_{20}$ tricycloalkyl, $C_6$-$C_{25}$ tetracycloalkyl, $C_3$-$C_{10}$ alkenyl, $C_4$-$C_{10}$ cycloalkenyl, $C_5$-$C_{15}$ bicycloalkenyl, $C_7$-$C_{20}$ tricycloalkenyl, $C_9$-$C_{25}$ tetracycloalkyl, $C_1$-$C_{10}$ amide, $C_3$-$C_{10}$ cyclic amide, $C_1$-$C_{10}$ amine, $C_3$-$C_{10}$ cyclic amine, $C_2$-$C_{10}$ ester, $C_3$-$C_{10}$ cyclic ester, $C_2$-$C_{10}$ ether, $C_3$-$C_{10}$ cyclic ether, $C_1$-$C_{10}$ sulfonamide, $C_3$-$C_{10}$ cyclic sulfonamide, $C_2$-$C_{10}$ sulfone, $C_3$-$C_{10}$ cyclic sulfone, $C_2$-$C_{10}$ urea, and $C_3$-$C_{10}$ cyclic urea is optionally substituted with one to three same or different of the following functionalities: $(C_{1-6})$alkyl, $(C_{3-6})$cycloalkyl, cyano, phenyl, aryl, heteroaryl, heteroalicyclic, hydroxy, $(C_{1-6})$alkoxy, halogen, primary amine, secondary amine, tertiary amine, ammonium, alcohol, ether, acid, ketone, amide, amidine, guanidine, sulfone, sulfonamide, sulfamide, acyl sulfamide, sulfate, phosphate, squarate, oxime, among which ether, secondary amine, tertiary amine, ammonium, ester, ketone, amide, amidine, oxime, can be either acyclic or cyclic.

In addition, it is preferred that $R_{81}$, $R_{82}$, $R_{83}$, $R_{84}$, $R_{85}$, $R_{86}$, and $R_{87}$ be selected from the group consisting of H, $(C_{1-6})$alkyl and $(C_{3-6})$cycloalkyl.

More preferred compounds of Formula I include those which are selected from the group consisting of:

23
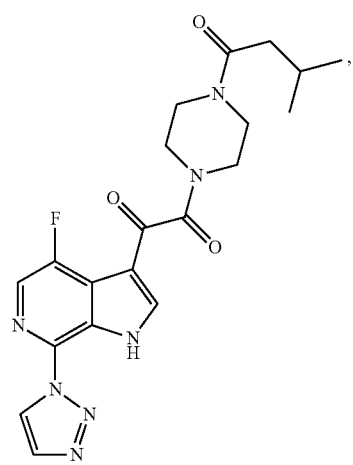
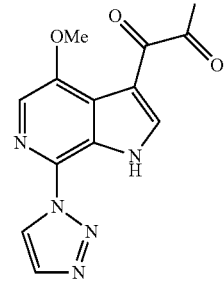
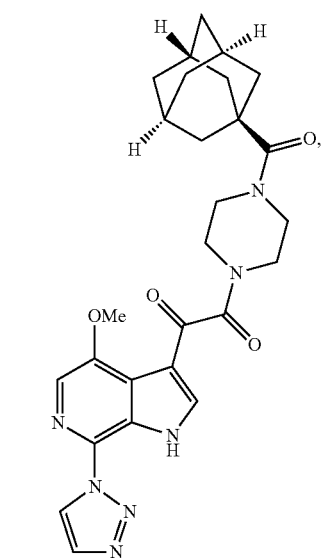
24
-continued
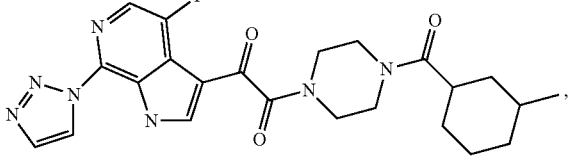
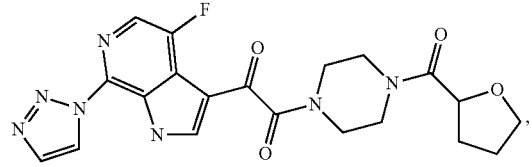
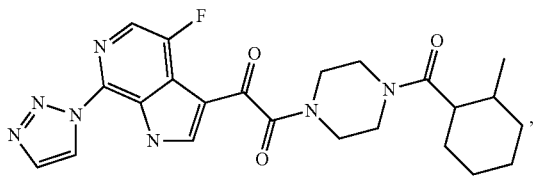
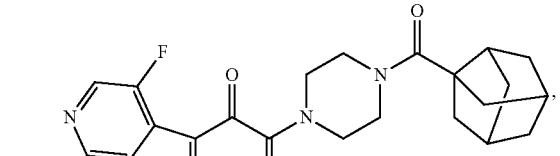
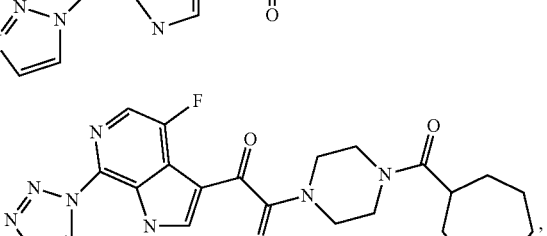
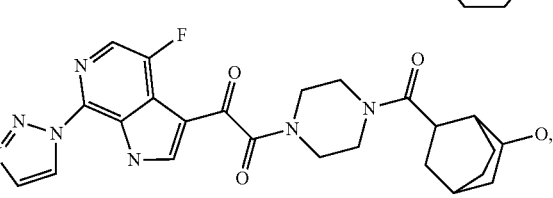

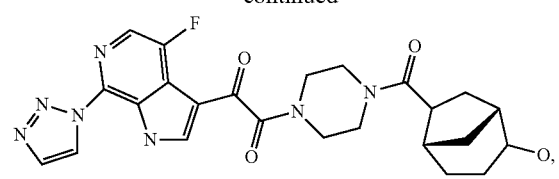
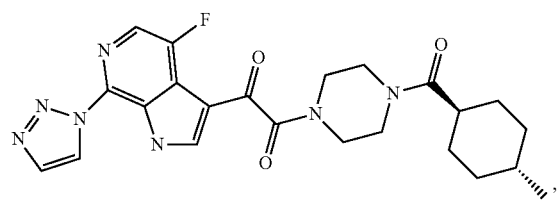
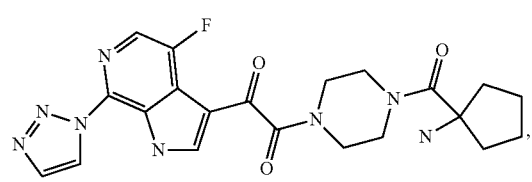
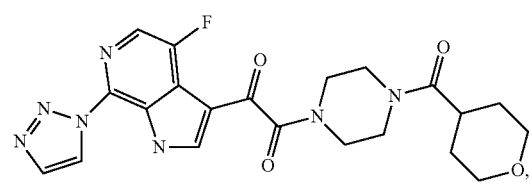
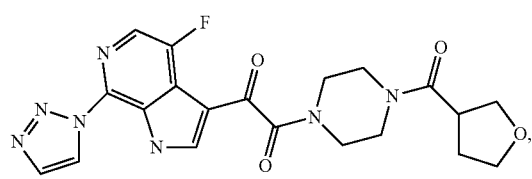
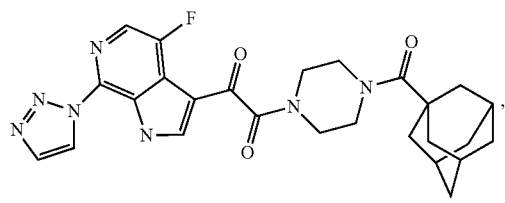
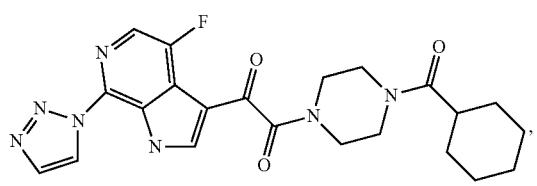
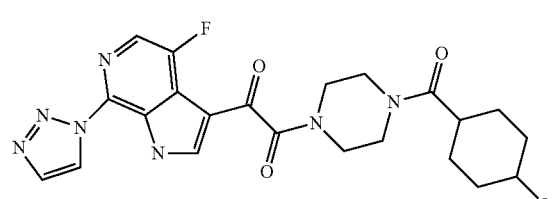
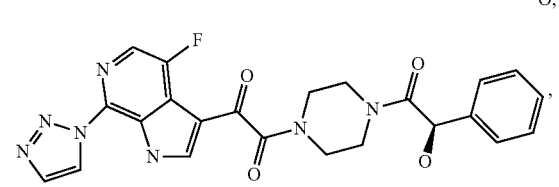
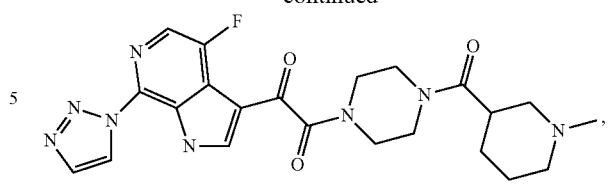
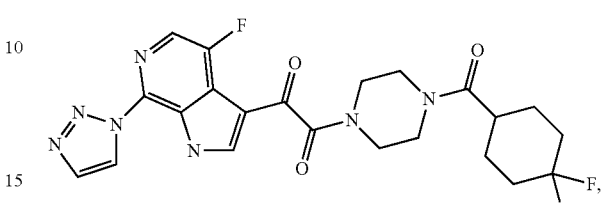
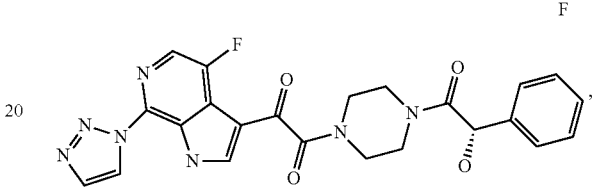
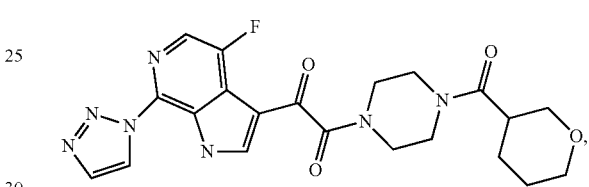
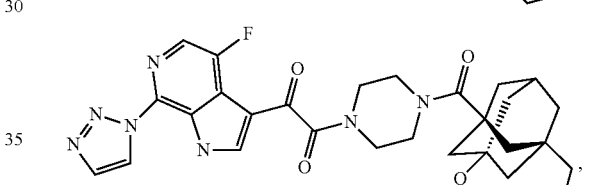
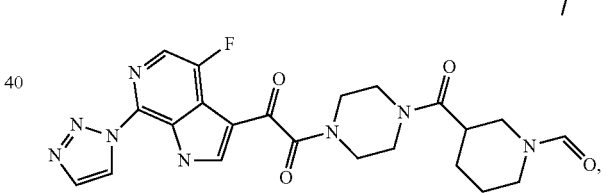
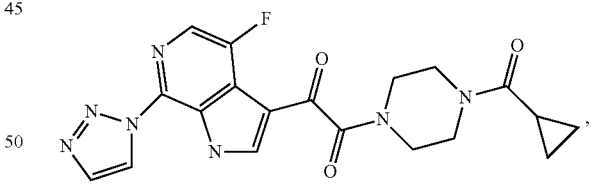
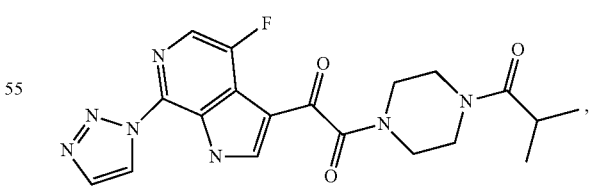
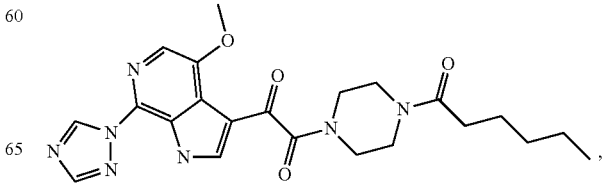

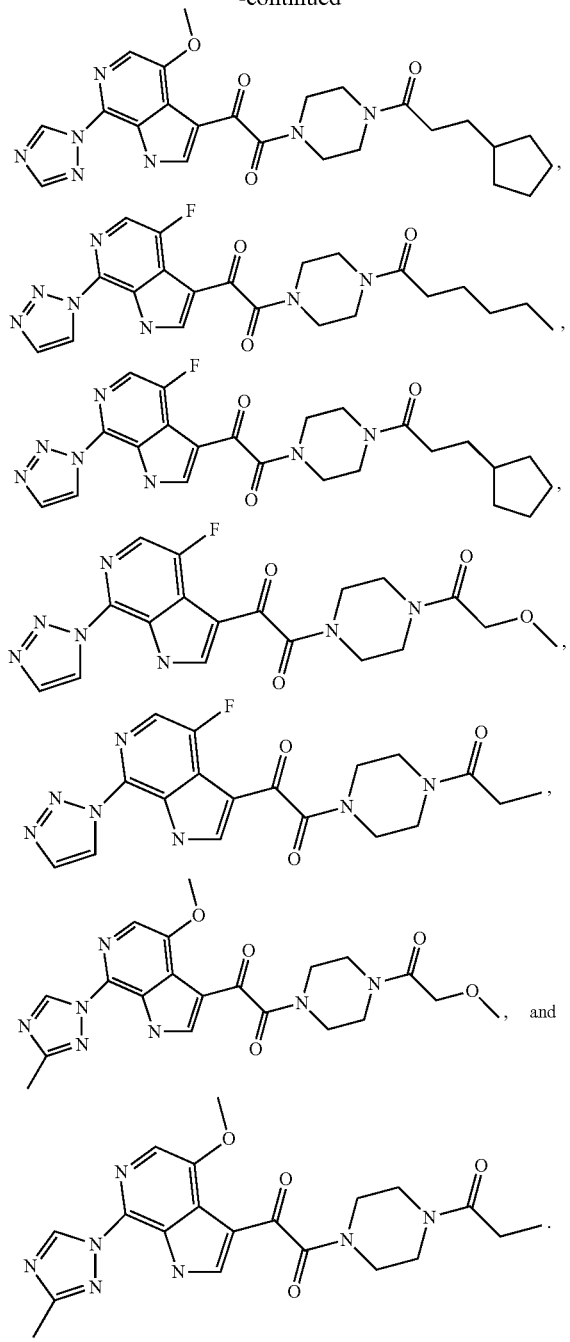

The compounds of the present invention, according to all the various embodiments described above, may be administered orally, parenterally (including subcutaneous injections, intravenous, intramuscular, intrasternal injection or infusion techniques), by inhalation spray, or rectally, and by other means, in dosage unit formulations containing non-toxic pharmaceutically acceptable carriers, excipients and diluents available to the skilled artisan. One or more adjuvants may also be included.

Thus, in accordance with the present disclosure, there is further provided a method of treatment, and a pharmaceutical composition, for treating viral infections such as HIV infection and AIDS. The treatment involves administering to a patient in need of such treatment a pharmaceutical composition which contains an antiviral effective amount of one or more of the compounds of Formula I, together with one or more pharmaceutically acceptable carriers, excipients or diluents. As used herein, the term "antiviral effective amount" means the total amount of each active component of the composition and method that is sufficient to show a meaningful patient benefit, i.e., inhibiting, ameliorating, or healing of acute conditions characterized by inhibition of the HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing, ameliorating or healing diseases associated with HIV infection.

The pharmaceutical compositions of the invention may be in the form of orally administrable suspensions or tablets; as well as nasal sprays, sterile injectable preparations, for example, as sterile injectable aqueous or oleaginous suspensions or suppositories. Pharmaceutically acceptable carriers, excipients or diluents may be utilized in the pharmaceutical compositions, and are those utilized in the art of pharmaceutical preparations.

When administered orally as a suspension, these compositions are prepared according to techniques typically known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents, and lubricants known in the art.

The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds of this disclosure can be administered orally to humans in a dosage range of 1 to 100 mg/kg body weight in divided doses, usually over an extended period, such as days, weeks, months, or even years. One preferred dosage range is 1 to 10 mg/kg body weight orally in divided doses. Another preferred dosage range is 1 to 20 mg/kg body weight in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Also contemplated herein are combinations of the compounds of Formula I herein set forth, together with one or more agents useful in the treatment of AIDS. For example, the compounds of this disclosure may be effectively administered, whether at periods of pre-exposure and/or post-exposure, in combination with effective amounts of the AIDS antivirals, immunomodulators, anti-infectives, or vaccines, such as those in the following non-limiting table:

| Drug Name | Manufacturer | Indication |
|---|---|---|
| ANTIVIRALS | | |
| 097 | Hoechst/Bayer | HIV infection, AIDS, ARC (non-nucleoside reverse transcriptase (RT) inhibitor) |
| Amprenavir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Darunavir | Tibotec-J & J | HIV infection, AIDS, ARC (protease inhibitor) |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266, Sustiva ®) (−)6-Chloro-4-(S)-cyclopropylethynyl-4(S)-trifluoro-methyl-1,4-dihydro-2H-3,1-benzoxazin-2-one, STOCRINE | Bristol Myers Squibb | HIV infection, AIDS, ARC (non-nucleoside RT inhibitor) |
| EL10 | Elan Corp, PLC (Gainesville, GA) | HIV infection |

| Drug Name | Manufacturer | Indication |
| --- | --- | --- |
| Etravirine | Tibotec/J & J | HIV infection, AIDS, ARC (non-nucleoside reverse transcriptase inhibitor) |
| Famciclovir | Smith Kline | herpes zoster, herpes simplex |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-Thymidine | Bristol-Myers Squibb | HIV infection, AIDS, ARC |
| Tipranavir | Boehringer Ingelheim | HIV infection, AIDS, ARC (protease inhibitor) |
| Valaciclovir | Glaxo Wellcome | Genital HSV & CMV Infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |

-continued

| Drug Name | Manufacturer | Indication |
|---|---|---|
| Tenofovir disoproxil, fumarate salt (Viread ®) | Gilead | HIV infection, AIDS, (reverse transcriptase inhibitor) |
| Emtriva ® (Emtricitabine) (FTC) | Gilead | HIV infection, AIDS, (reverse transcriptase inhibitor) |
| Combivir ® | GSK | HIV infection, AIDS, (reverse transcriptase inhibitor) |
| Abacavir succinate (or Ziagen ®) | GSK | HIV infection, AIDS, (reverse transcriptase inhibitor) |
| Reyataz ® (or atazanavir) | Bristol-Myers Squibb | HIV infection AIDs, protease inhibitor |
| Fuzeon ® (Enfuvirtide or T-20) | Roche/Trimeris | HIV infection AIDs, viral Fusion inhibitor |
| Lexiva ® (or Fosamprenavir calcium) | GSK/Vertex | HIV infection AIDs, viral protease inhibitor |
| Selzentry Maraviroc; (UK 427857) | Pfizer | HIV infection AIDs, (CCR5 antagonist, in development) |
| Trizivir ® | GSK | HIV infection AIDs, (three drug combination) |
| Sch-417690 (vicriviroc) | Schering-Plough | HIV infection AIDs, (CCR5 antagonist, in development) |
| TAK-652 | Takeda | HIV infection AIDs, (CCR5 antagonist, in development) |
| GSK 873140 (ONO-4128) | GSK/ONO | HIV infection AIDs, (CCR5 antagonist, in development) |
| Integrase Inhibitor MK-0518 Raltegravir | Merck | HIV infection AIDs |
| Truvada ® | Gilead | Combination of Tenofovir disoproxil fumarate salt (Viread ®) and Emtriva ® (Emtricitabine) |
| Integrase Inhibitor GS917/JTK-303 Elvitegravir | Gilead/Japan Tobacco | HIV Infection AIDs in development |
| Triple drug combination Atripla ® | Gilead/Bristol-Myers Squibb | Combination of Tenofovir disoproxil fumarate salt (Viread ®), Emtriva ® (Emtricitabine), and Sustiva ® (Efavirenz) |
| Festinavir ® | Oncolys BioPharma | HIV infection AIDs in development |
| CMX-157 Lipid conjugate of nucleotide tenofovir | Chimerix | HIV infection AIDs |
| GSK1349572 Integrase inhibitor | GSK | HIV infection AIDs |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | Wyeth Lederle Labs | AIDS, Kaposi's sarcoma |
| FP-21399 | Fuki ImmunoPharm | Blocks HIV fusion with CD4+ cells |
| Gamma Interferon | Genentech | ARC, in combination w/TNF (tumor necrosis factor) |

-continued

| Drug Name | Manufacturer | Indication |
| --- | --- | --- |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |

| Drug Name | Manufacturer | Indication |
| --- | --- | --- |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Additionally, the compounds of the disclosure herein set forth may be used in combination with other HIV entry inhibitors. Examples of such HIV entry inhibitors are discussed in *Drugs of the Future,* 24(12):1355-1362 (1999); *Cell,* 9:243-246 (Oct. 29, 1999); and *Drug Discovery Today,* 5(5):183-194 (May 2000) and Meanwell, N. A. et al., "Inhibitors of the entry of HIV into host cells", *Curr. Op. Drug Disc. Dev,* 6(4):451-461 (2003). Specifically the compounds can be utilized in combination with other attachment inhibitors, fusion inhibitors, and chemokine receptor antagonists aimed at either the CCR5 or CXCR4 coreceptor.

It will be understood that the scope of combinations of the compounds of this disclosure with AIDS antivirals, immunomodulators, anti-infectives, HIV entry inhibitors or vaccines is not limited to the list in the above Table but includes, in principle, any combination with any pharmaceutical composition useful for the treatment of AIDS.

Preferred combinations are simultaneous or alternating treatments with a compound of the present disclosure and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is REYATAZ® (active ingredient Atazanavir). Typically a dose of 300 to 600 mg is administered once a day. This may be co-administered with a low dose of Ritonavir (50 to 500 mgs). Another preferred inhibitor of HIV protease is KALETRA®. Another useful inhibitor of HIV protease is indinavir, which is the sulfate salt of N-(2 (R)-hydroxy-1-(S)-indanyl)-2(R)-phenylmethyl-4-(S)-hydroxy-5-(1-(4-(3-pyridyl-methyl)-2(S)—N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and 141W94 and 1592U89; (5) zidovudine and lamivudine. (The preparation of ddC, ddI and AZT are also described in EP 0 484 071.)

In such combinations the compound of the present disclosure and other active agents may be administered separately or in conjunction. In addition, the administration of one element may be prior to, concurrent to, or subsequent to the administration of other agent(s).

GENERAL CHEMISTRY (METHODS OF SYNTHESIS)

The present invention comprises compounds of Formula I, their pharmaceutical formulations, and their use in patients suffering from or susceptible to HIV infection. The compounds of Formula I include pharmaceutically acceptable salts thereof. General procedures to construct compounds of Formula I and intermediates useful for their synthesis are described in the following Schemes (after the Abbreviations).

Abbreviations

One or more of the following abbreviations, most of which are conventional abbreviations well known to those skilled in the art, may be used throughout the description of the disclosure and the examples:
h=hour(s)
rt=room temperature
mol=mole(s)
mmol=millimole(s)
g=gram(s)
mg=milligram(s)
mL=milliliter(s)
TFA=trifluoroacetic Acid
DCE=1,2-Dichloroethane
$CH_2Cl_2$=dichloromethane
TPAP=tetrapropylammonium perruthenate
THF=tetrahydrofuran
DEPBT=3-(diethoxyphosphoryloxy)-1,2,3-benzotriazin-4(3H)-one
DMAP=4-dimethylaminopyridine
P-EDC=polymer supported 1-(3-dimethylaminopropyl)-3-ethylcarbodiimide
EDC=1-(3-dimethylaminopropyl)-3-ethylcarbodiimide
DMF=N,N-dimethylformamide
Hunig's Base=N,N-diisopropylethylamine
MCPBA=meta-chloroperbenzoic acid
azaindole=1H-pyrrolo-pyridine 4-azaindole=1H-pyrrolo[3,2-b]pyridine
5-azaindole=1H-pyrrolo[3,2-c]pyridine
6-azaindole=1H-pyrrolo[2,3-c]pyridine
7-azaindole=1H-pyrrolo[2,3-b]pyridine
PMB=4-methoxybenzyl
DDQ=2,3-dichloro-5,6-dicyano-1,4-benzoquinone
OTf=trifluoromethanesulfonoxy
NMM=4-methylmorpholine
PIP-COPh=1-benzoylpiperazine
NaHMDS=sodium hexamethyldisilazide
EDAC=1-(3-dimethylaminopropyl)-3-ethylcarbodiimide
TMS=trimethylsilyl
DCM=dichloromethane
DCE=dichloroethane
MeOH=methanol
THF=tetrahydrofuran
EtOAc=ethyl acetate
LDA=lithium diisopropylamide
TMP-Li=2,2,6,6-tetramethylpiperidinyl lithium
DME=dimethoxyethane
DIBALH=diisobutylaluminum hydride
HOBT=1-hydroxybenzotriazole
CBZ=benzyloxycarbonyl
PCC=pyridinium chlorochromate
TBTU=O-(benzotriazol-1-yl)-N,N,N',N'-tetramethyluronium tetrafluoroborate
DEBPT=3-(diethoxyphosphoryloxy)-1,2,3-benzotriazin-4(3H)-one
BOP=benzotriazole-1-yl-oxy-tris-(dimethylamino)-phosphoniumhexafluorophosphate Chemistry Intermediate ACOCOOH The preparation of template A-CO—CO—OH has been described in detail in WO-2001062255 (T. Wang, et al.), WO-200204440 (O. Wallace, et al.) and WO-2002062423 (T. Wang, et al.).

Syntheses of the Compounds of Formula I

Detailed procedures of coupling ACOCOOH and piperazine derivative were described in application (T. Wang, et al. WO-2001062255, T. Wang, et al. WO-2002062423, T. Wang, et al. US-2007249579 and T. Wang, et al. US-2004063744). ACOCOOH 1 (1 eq.), piperazine derivative 2 (1-5 eq.), 3-(diethoxyphosphoryloxy)-1,2,3-benzotriazin-4(3H)-one (DEPBT) or O-(1H-benzotriazol-1-yl)-N,N,N',N'-tetramethyluronium tetrafluoroborate (TBTU) (1-5 eq.) or (2-(7-Aza-1H-benzotriazole-1-yl)-1,1,3,3-tetramethyluronium hexafluorophosphate) (HATU) (1-5 eq.) and Hunig's Base or N-methyl morpholine or triethyl amine (1-100 eq.) were combined in THF or DMF. The reactions were carried out at either room temperature or increased temperature to generate the Compounds of Formula I (Scheme 1).

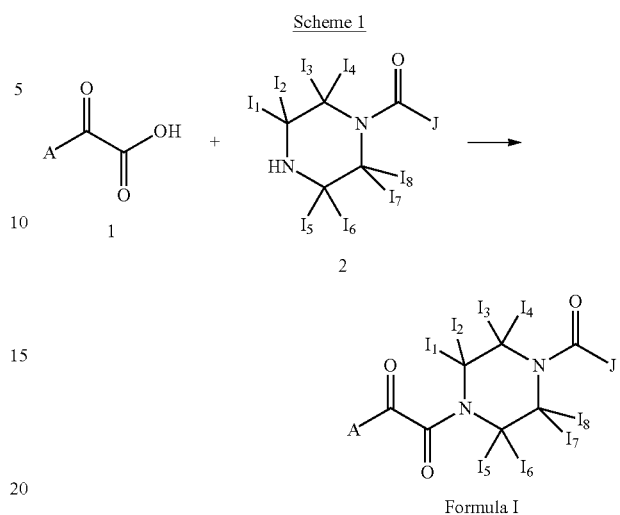

Scheme 1

Alternatively, as shown in Scheme 2, ACOCOOH 1 (1 eq.), N-Boc-piperazine 3 (1-5 eq.), 3-(diethoxyphosphoryloxy)-1,2,3-benzotriazin-4(3H)-one (DEPBT) or O-(1H-benzotriazol-1-yl)-N,N,N',N'-tetramethyluronium tetrafluoroborate (TBTU) (1-5 eq.) or (2-(7-Aza-1H-benzotriazole-1-yl)-1,1,3,3-tetramethyluronium hexafluorophosphate) (HATU) (1-5 eq.) and Hunig's Base or N-methyl morpholine or triethyl amine (1-100 eq.) were combined in THF or DMF. The reactions were carried out at either room temperature or increased temperature to offer N-Boc N'-2-ketoamide 4. The Boc protecting group of compound 4 was removed in a solution of TFA in dichloromethane (1% to 100%) or HCl in ether (2N) at room temperature or increased temperature for 30 minutes to 18 hours to give free amine 5. The free amine 5 coupled with acid 6 using DEPBT or TBTU or HATU as coupling agent (1-5 eq.) and Hunig's Base or N-methyl morpholine or triethyl amine as base in THF or DMF at either room temperature or increased temperature to produce the Compounds of Formula I. Or, the free amine 5 reacted with acyl chloride 7 using Hunig's Base or N-methyl morpholine or triethyl amine as base in THF or DMF or $CH_2Cl_2$ at either room temperature or increased temperature to produce the Compounds of Formula I.

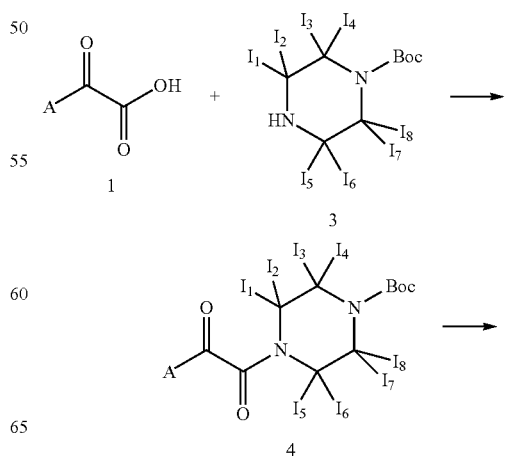

-continued

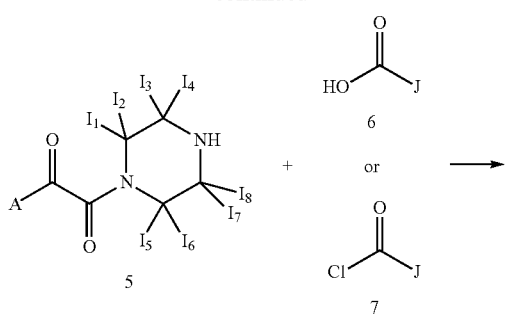

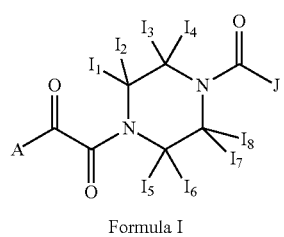

Formula I

Chemistry Experimental

LC/MS Method (i.e., Compound Identification)

All Liquid Chromatography (LC) data were recorded on a Shimadzu LC-10AS or LC-20AS liquid chromotograph using a SPD-10AV or SPD-20A UV-Vis detector and Mass Spectrometry (MS) data were determined with a Micromass Platform for LC in electrospray mode.

HPLC Method (i.e., Compound Isolation)

Compounds purified by preparative HPLC were diluted in methanol (1.2 mL) and purified using a Shimadzu LC-8A or LC-10A automated preparative HPLC system.

Intermediate ACOCOOH

The preparation of template A-CO—CO—OH has been described in detail in WO-2001062255 (T. Wang, et al.), WO-200204440 (O. Wallace, et al.) and WO-2002062423 (T. Wang, et al.). Some examples of ACOCOOH are listed in below.

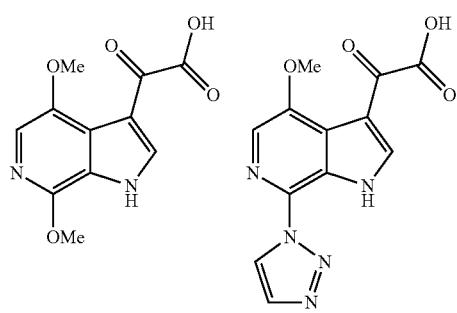

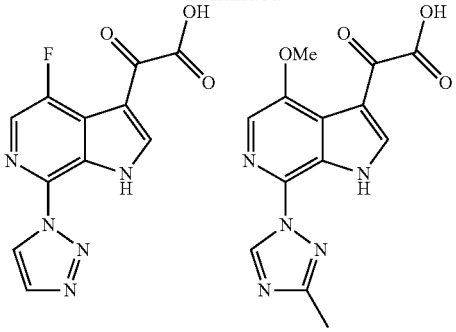

Intermediate 2-keto piperazine amide

Typical procedure to prepare 2-keto piperazine amide intermediates, synthesis of 1-(4-methoxy-7-(3-methyl-1H-1,2,4-triazol-1-yl)-1H-pyrrolo[2,3-c]pyridin-3-yl)-2-(piperazin-1-yl)ethane-1,2-dione:

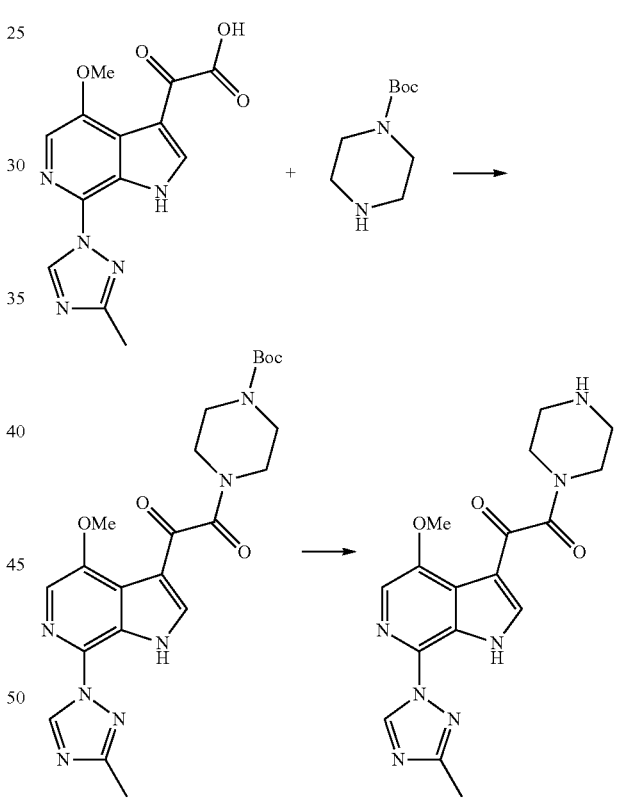

Step 1: iPr$_2$NEt (5 mL) was added into a solution of 2-(4-methoxy-7-(3-methyl-1H-1,2,4-triazol-1-yl)-1H-pyrrolo[2,3-c]pyridin-3-yl)-2-oxoacetic acid (2 g), tert-butyl piperazine-1-carboxylate (1.24 g) and DEPBT (1.99 g) in DMF (50 mL) at room temperature. The reaction was stirred for 72 hours, then heated to 115° C. for 24 hours, before quenched with sodium bicarbonate (50 mL). The aqueous layer was extracted with EtOAc (3×50 ml). The combined organic phase was dried over Mg$_2$SO$_4$ and concentrated under vacuum to give a crude product, which was partially purified by HPLC, while the rest was used in the further step without purification.

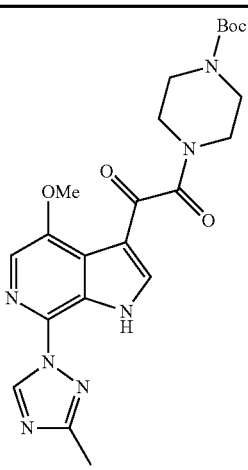

tert-butyl 4-(2-(4-methoxy-7-(3-methyl-1H-1,2,4-triazol-1-yl)-1H-pyrrolo[2,3-c]pyridin-3-yl)-2-oxoacetyl)piperazine-1-carboxylate

| | |
|---|---|
| MS (M − H)⁺ Calcd. | 468.2 |
| MS (M − H)⁺ Observ. | 468.3 |
| Retention Time | 1.40 min |
| | LC Condition |
| Solvent A | 5% ACN: 95% Water: 10 mM Ammonium Actetate |
| Solvent B | 95% ACN: 5% Water: 10 mM Ammonium Actetate |
| Start % B | 0 |
| Final % B | 100 |
| Gradient Time | 2 min |
| Flow Rate | 4 mL/min |
| Wavelength | 220 |
| Solvent Pair | ACN: Water: Ammonium Actetate |
| Column | PHENOMENEX-LUNA, 4.6 × 50 mm, S5 |

Step 2: TFA (4 mL) was added into a solution of tert-butyl 4-(2-(4-methoxy-7-(3-methyl-1H-1,2,4-triazol-1-yl)-1H-pyrrolo[2,3-c]pyridin-3-yl)-2-oxoacetyl)piperazine-1-carboxylate (500 mg) in CH$_2$Cl$_2$ (20 mL) at room temperature. The reaction was stirred overnight and quenched with sodium bicarbonate (20 mL). The aqueous layer was extracted with EtOAc (3×20 mL). The combined organic phase was dried over Mg$_2$SO$_4$ and concentrated under vacuum to give a crude product, which was purified by silica gel chromatography.

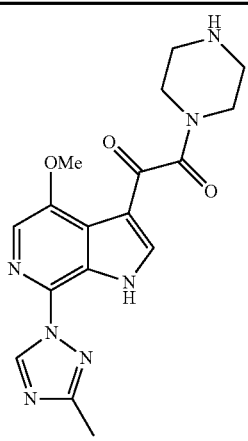

1-(4-methoxy-7-(3-methyl-1H-1,2,4-triazol-1-yl)-1H-pyrrolo[2,3-c]pyridin-3-yl)-2-(piperazin-1-yl)ethane-1,2-dione

| | |
|---|---|
| MS (M + H)⁺ Calcd. | 370.2 |
| MS (M + H)⁺ Observ. | 370.2 |
| Retention Time | 0.90 min |
| | LC Condition |
| Solvent A | 5% ACN: 95% Water: 10 mM Ammonium Actetate |
| Solvent B | 95% ACN: 5% Water: 10 mM Ammonium Actetate |
| Start % B | 0 |
| Final % B | 100 |
| Gradient Time | 2 min |
| Flow Rate | 4 mL/min |
| Wavelength | 220 |
| Solvent Pair | ACN: Water: Ammonium Actetate |
| Column | PHENOMENEX-LUNA, 4.6 × 50 mm, S5 |

1-(4-Fluoro-7-(1H-1,2,3-triazol-1-yl)-1H-pyrrolo[2,3-c]pyridin-3-yl)-2-(piperazin-1-yl)ethane-1,2-dione was synthesis via the same process to prepare 1-(4-methoxy-7-(3-methyl-1H-1,2,4-triazol-1-yl)-1H-pyrrolo[2,3-c]pyridin-3-yl)-2-(piperazin-1-yl)ethane-1,2-dione, using 2-(4-fluoro-7-(1H-1,2,3-triazol-1-yl)-1H-pyrrolo[2,3-c]pyridin-3-yl)-2-oxoacetic acid as a starting material.

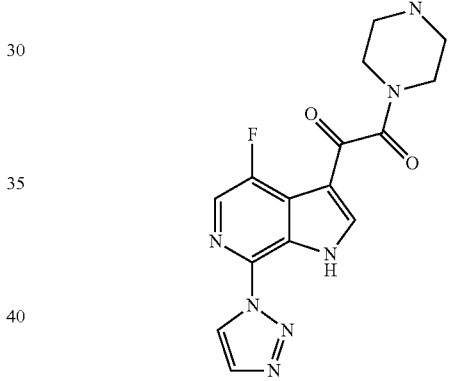

1-(4-fluoro-7-(1H-1,2,3-triazol-1-yl)-1H-pyrrolo[2,3-c]pyridin-3-yl)-2-(piperazin-1-yl)ethane-1,2-dione

| | |
|---|---|
| MS (M + H)⁺ Calcd. | 344.1 |
| MS (M + H)⁺ Observ. | 344.2 |
| Retention Time | 0.95 min |
| | LC Condition |
| Solvent A | 5% ACN: 95% Water: 10 mM Ammonium Actetate |
| Solvent B | 95% ACN: 5% Water: 10 mM Ammonium Actetate |
| Start % B | 0 |
| Final % B | 100 |
| Gradient Time | 2 min |
| Flow Rate | 4 mL/min |
| Wavelength | 220 |
| Solvent Pair | ACN: Water: Ammonium Actetate |
| Column | PHENOMENEX-LUNA, 4.6 × 50 mm, S5 |

1-(4-Methoxy-7-(1H-1,2,3-triazol-1-yl)-1H-pyrrolo[2,3-c]pyridin-3-yl)-2-(piperazin-1-yl)ethane-1,2-dione was synthesis via the same process to prepare 1-(4-methoxy-7-(3-methyl-1H-1,2,4-triazol-1-yl)-1H-pyrrolo[2,3-c]pyridin-3-yl)-2-(piperazin-1-yl)ethane-1,2-dione, using 2-(4-methoxy-7-(1H-1,2,3-triazol-1-yl)-1H-pyrrolo[2,3-c]pyridin-3-yl)-2-oxoacetic acid as a starting material.

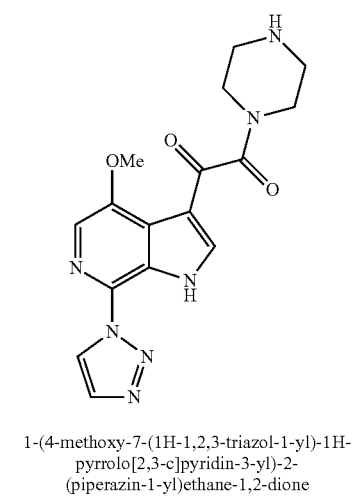

1-(4-methoxy-7-(1H-1,2,3-triazol-1-yl)-1H-pyrrolo[2,3-c]pyridin-3-yl)-2-(piperazin-1-yl)ethane-1,2-dione

| | |
|---|---|
| MS (M + H)+ Calcd. | 356.1 |
| MS (M + H)+ Observ. | 356.0 |
| Retention Time | 0.98 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 5 mL/min |
| Wavelength | 220 |
| Solvent Pair | Water-Methanol-TFA |
| Column | Xterra 4.6 × 50 mm C18 5 um |

Syntheses of the Compounds of Formula I

Preparation of Compound 1001, 1-(4-fluoro-7-(1H-1,2,3-triazol-1-yl)-1H-pyrrolo[2,3-c]pyridin-3-yl)-2-(4-(3-methylbutanoyl)piperazin-1-yl)ethane-1,2-dione

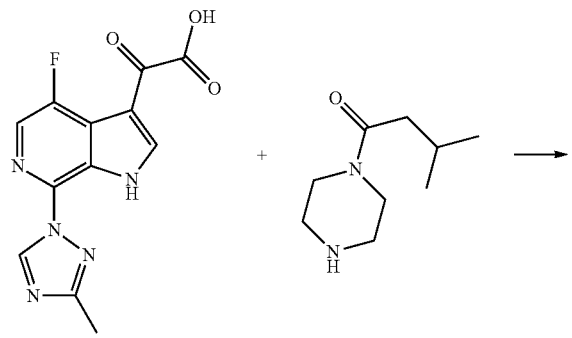

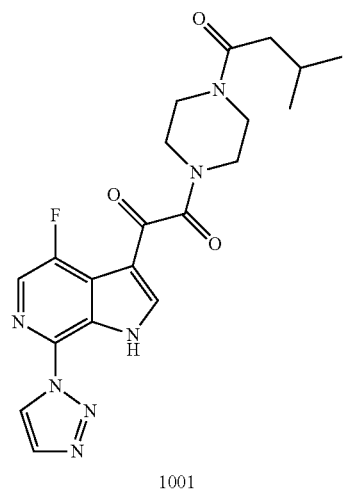

1001

2-(4-Fluoro-7-(1H-1,2,3-triazol-1-yl)-1H-pyrrolo[2,3-c]pyridin-3-yl)-2-oxoacetic acid (100 mg), 3-methyl-1-(piperazin-1-yl)butan-1-one (74 mg), TBTU (128 mg) and Hunig's Base (0.2 mL) were combined in DMF (1.5 mL). The mixture was stirred at room temperature for 17 hours. DMF was removed via evaporation at reduced pressure and the residue was recrystallized in MeOH to give Compound 1001 (54 mg).

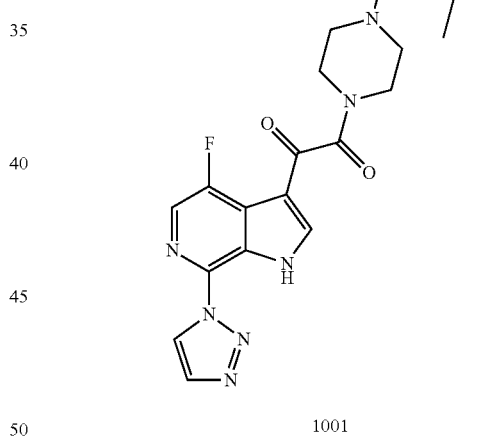

1001

| | |
|---|---|
| MS (M + H)+ Calcd. | 428.2 |
| MS (M + H)+ Observ. | 427.9 |
| Retention Time | 1.73 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 4 mL/min |
| Wavelength | 220 |
| Solvent Pair | Water-Methanol-TFA |
| Column | PHENOMENEX-LUNA 4.6 × 50 mm S10 |

Preparation of Compound 1002, 1-(4-(cyclohexanecarbonyl)piperazin-1-yl)-2-(4-methoxy-7-(1H-1,2,3-triazol-1-yl)-1H-pyrrolo[2,3-c]pyridin-3-yl)ethane-1,2-dione and Compound 1003

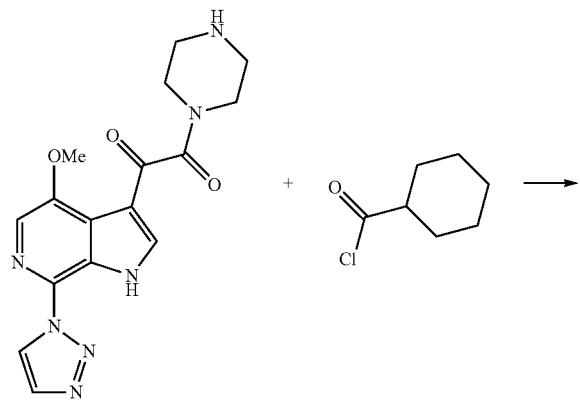

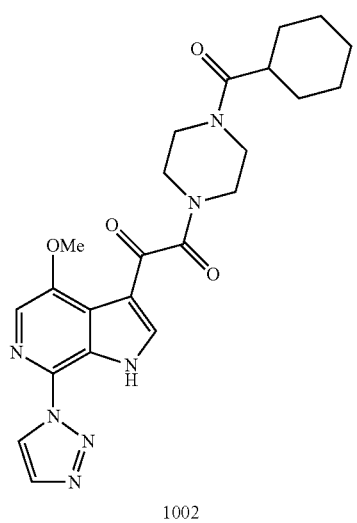

1002

1-(4-Methoxy-7-(1H-1,2,3-triazol-1-yl)-1H-pyrrolo[2,3-c]pyridin-3-yl)-2-(piperazin-1-yl)ethane-1,2-dione (100 mg) and cyclohexanecarbonyl chloride (41 mg) were combined in 10% Et₃N in THF (5 mL). The mixture was stirred at room temperature for 3 hour, before was quenched by 5 mL of saturated NaHCO₃ aqueous solution. The aqueous phase was extracted with EtOAc (2×10 mL). The combined organic layer was combined, washed with brine (30 mL), dried over MgSO₄ and concentrated under vacuum to give a residue which was purified by preparative HPLC to afford Compound 1002 (30 mg).

1002

| | |
|---|---|
| MS (M + H)⁺ Calcd. | 466.2 |
| MS (M + H)⁺ Observ. | 466.1 |
| Retention Time | 2.20 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 5 mL/min |
| Wavelength | 220 |
| Solvent Pair | Water-Methanol-TFA |
| Column | XTERRA 4.6 × 30 mm S5 |

Compound 1003 was synthesis via the same process to prepare Compound 1002, using 1-adamantanecabonyl chloride as a starting material.

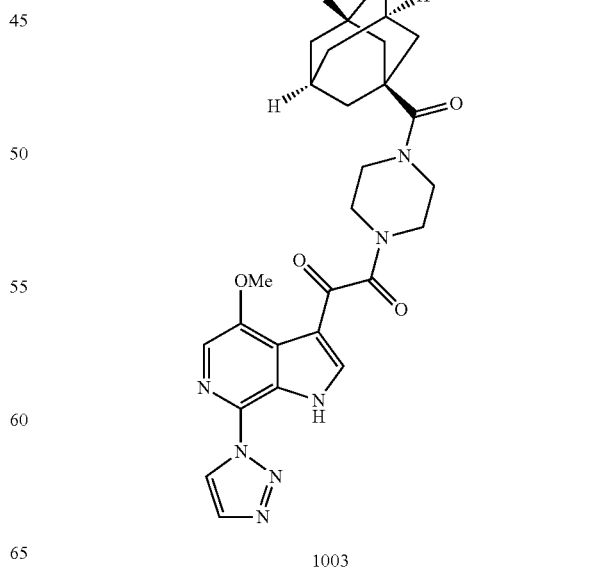

1003

| | |
|---|---|
| MS (M + H)⁺ Calcd. | 518.2 |
| MS (M + H)⁺ Observ. | 518.2 |
| Retention Time | 2.43 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 5 mL/min |
| Wavelength | 220 |
| Solvent Pair | Water-Methanol-TFA |
| Column | XTERRA 4.6 × 30 mm S5 |

Preparation of Compound 1004, 1-(4-(cycloheptanecarbonyl)piperazin-1-yl)-2-(4-methoxy-7-(1H-1,2,3-triazol-1-yl)-1H-pyrrolo[2,3-c]pyridin-3-yl)ethane-1,2-dione

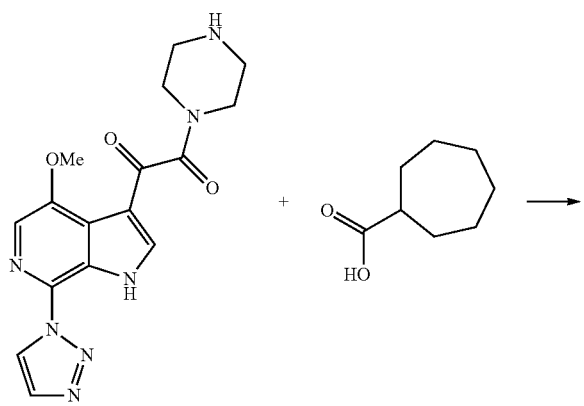

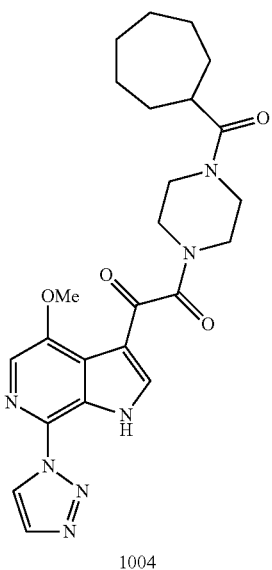

1004

1-(4-Methoxy-7-(1H-1,2,3-triazol-1-yl)-1H-pyrrolo[2,3-c]pyridin-3-yl)-2-(piperazin-1-yl)ethane-1,2-dione (50 mg), cycloheptanecarboxylic acid (26 mg), TBTU (64 mg) and Hunig's Base (0.1 mL) were combined in DMF (1 mL). The mixture was stirred at room temperature for 24 hours, before was quenched by 5 mL of saturated NaHCO₃ aqueous solution. The aqueous phase was extracted with EtOAc (2×10 mL). The combined organic layer was combined, washed with brine (30 mL), dried over MgSO₄ and concentrated under vacuum to give a residue which was purified by preparative HPLC to afford Compound 1004 (10 mg).

| | |
|---|---|
| MS (M + H)⁺ Calcd. | 480.2 |
| MS (M + H)⁺ Observ. | 480.2 |
| Retention Time | 1.73 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 4 mL/min |
| Wavelength | 220 |
| Solvent Pair | Water-Methanol-TFA |
| Column | PHENOMENEX-LUNA 4.6 × 50 mm S10 |

The following methods were used to prepare Compounds 2001-2051.

Analytical HPLC method 1: Waters Xbridge 2.1×50 mm 5 um C18, A=5:95 ACN:Water; B=95:5 ACN:Water; Modifier=10 mM NH₄OAc. 0.00 min=0% B, 2.0 min=100% B, 3.0 min=100% B, 3.05 min=0% B, 3.5 min=0% B, Flow rate=1 mL/min Analytical HPLC method 2: Phenomenex, Gemini 100× 4.6 mm, 5u C18, A=Water, B=ACN; Modifier=10 mM NH₄OAc. 0.00 min=10% B, 6.0 min=95% B, 6.5 min=95% B, 7.0 min=10% B, 8.0 min=10% B, Flow rate=1.2 mL/min Analytical HPLC method 3: Onyx Monolithic C18 50×4.6 mm, 5u C18, A=Water, B=ACN; Modifier=10 mM NH₄OAc. 0.00 min=10% B, 3.0 min=95% B, 4.0 min=95% B, 4.2 min=10% B, 5.0 min=10% B, Flow rate=1.2 mL/min The general procedures below pertain to the experimental procedure for library compounds.

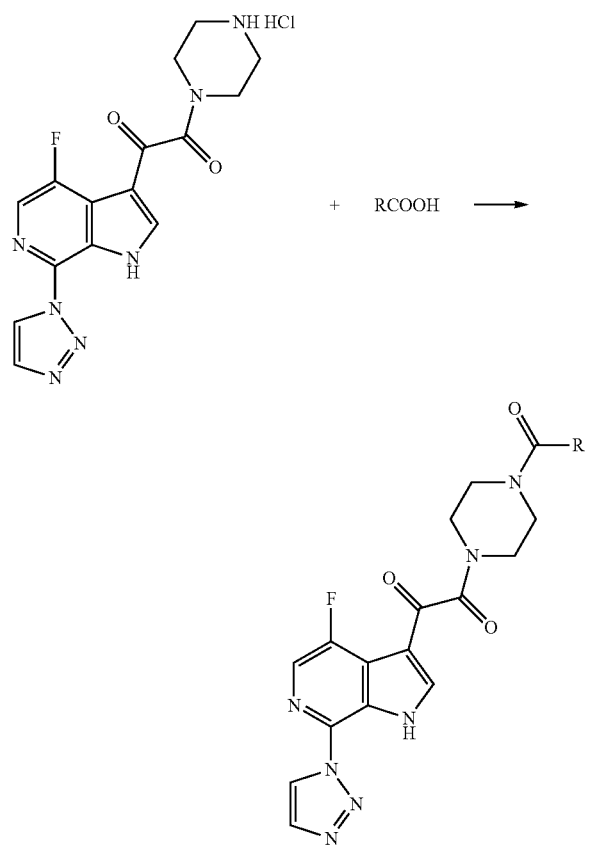

+ RCOOH ⟶

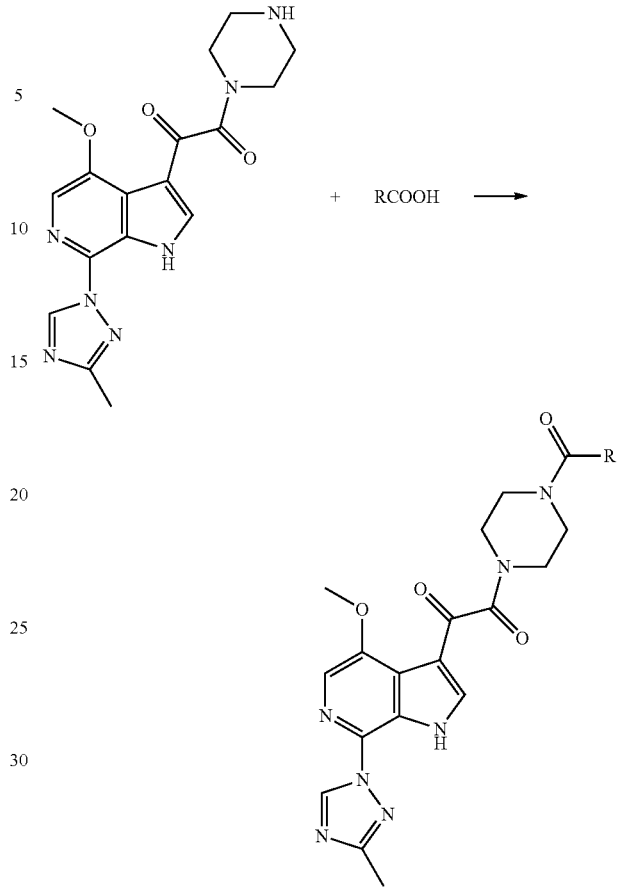

+ RCOOH ⟶

1-(4-Fluoro-7-(1H-1,2,3-triazol-1-yl)-1H-pyrrolo[2,3-c]pyridin-3-yl)-2-(piperazin-1-yl)ethane-1,2-dione hydrochloride (1 eq.) in DMF was added into a Wheaton tube (16×100 mm) which contained pre-weighed acid (3 eq.) and followed by adding DIPEA (5 eq.) and DMF. The mixture was shaken at room temperature overnight. All samples were transferred into a plate and purified by HPLC.

1-(4-Methoxy-7-(3-methyl-1H-1,2,4-triazol-1-yl)-1H-pyrrolo[2,3-c]pyridin-3-yl)-2-(piperazin-1-yl)ethane-1,2-dione (1 eq.) in DMF was added into a Wheaton tube (16×100 mm) which contained pre-weighed acid (3 eq.) and followed by adding DIPEA (5 eq.) and DMF. The mixture was shaken at room temperature overnight. All samples were transferred into a plate and purified by HPLC.

| Cmpd # | Structure | MS (M + H)+ Calcd. | MS (M + H)+ Observ. | RT (min) | Method |
|---|---|---|---|---|---|
| 2001 | 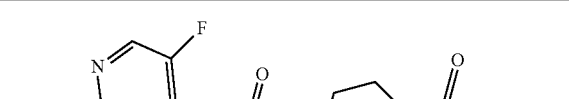 | 468.2 | 468.2 | 7.09 | 1 |
| 2002 | 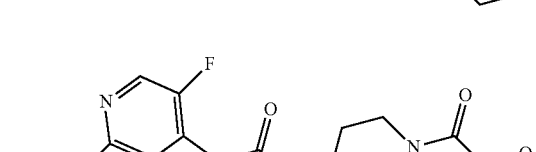 | 442.2 | 442.2 | 4.12 | 1 |

-continued

| Cmpd # | Structure | MS (M + H)+ Calcd. | MS (M + H)+ Observ. | RT (min) | Method |
|---|---|---|---|---|---|
| 2003 | 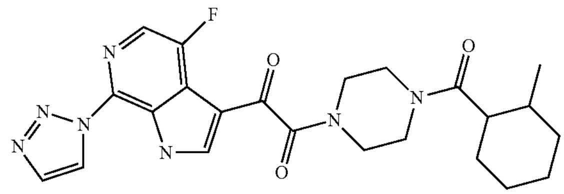 | 468.2 | 468.3 | 6.92 | 1 |
| 2004 | 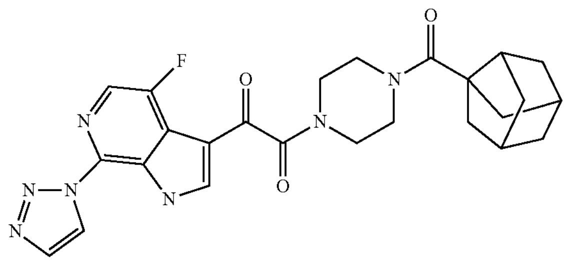 [SMILES: O=C(C(=O)N1CCN(C(=O)C23CC4CC(CC2C4)C3)CC1)c1c[nH]c2c(-n3ccnn3)ncc(F)c12] | 492.2 | 492.2 | 7.36 | 1 |
| 2005 | 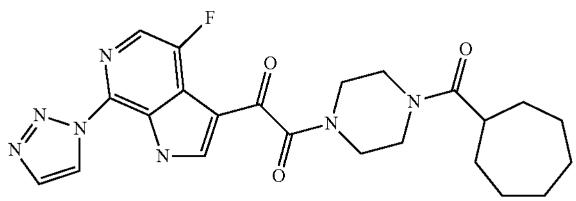 [SMILES: O=C(C(=O)N1CCN(C(=O)C2CCCCCC2)CC1)c1c[nH]c2c(-n3ccnn3)ncc(F)c12] | 468.2 | 468.3 | 6.93 | 1 |
| 2006 | 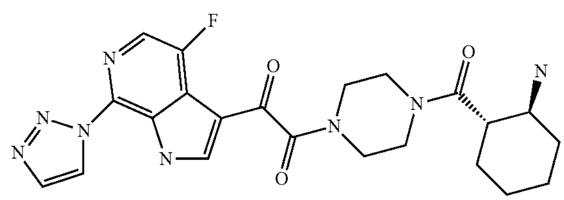 [SMILES: N[C@H]1CCCC[C@@H]1C(=O)N1CCN(C(=O)C(=O)c2c[nH]c3c(-n4ccnn4)ncc(F)c23)CC1] | 469.2 | 469.2 | 3.36 | 1 |
| 2007 | 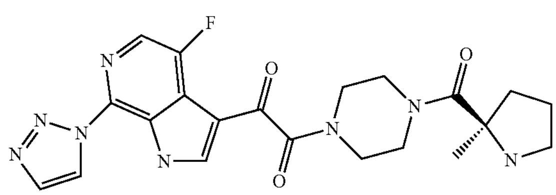 [SMILES: C[C@]1(C(=O)N2CCN(C(=O)C(=O)c3c[nH]c4c(-n5ccnn5)ncc(F)c34)CC2)CCCN1] | 455.2 | 455.2 | 3.05 | 1 |
| 2008 | 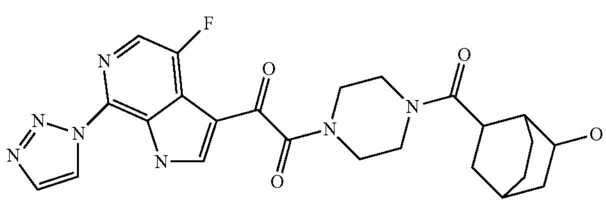 [SMILES: O=C(C(=O)N1CCN(C(=O)C2CC3CCC2C(O)C3)CC1)c1c[nH]c2c(-n3ccnn3)ncc(F)c12] | 496.2 | 496.2 | 4.89 | 1 |
| 2009 | 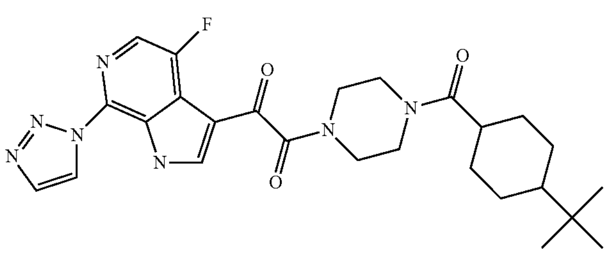 [SMILES: CC(C)(C)C1CCC(C(=O)N2CCN(C(=O)C(=O)c3c[nH]c4c(-n5ccnn5)ncc(F)c34)CC2)CC1] | 510.3 | 510.3 | 8.86 | 1 |

-continued

| Cmpd # | Structure | MS (M + H)+ Calcd. | MS (M + H)+ Observ. | RT (min) | Method |
|---|---|---|---|---|---|
| 2010 | 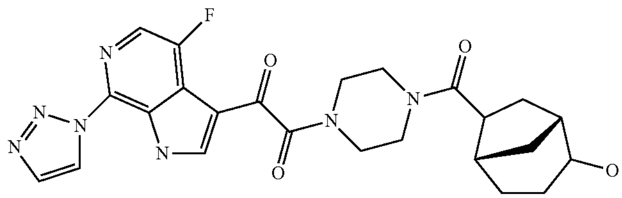 [SMILES: O=C(C(=O)N1CCN(C(=O)C2C[C@H]3C[C@@H]2CCC3O)CC1)c1c[nH]c2c(-n3ccnn3)ncc(F)c12] | 496.2 | 496.2 | 4.22 | 1 |
| 2011 | 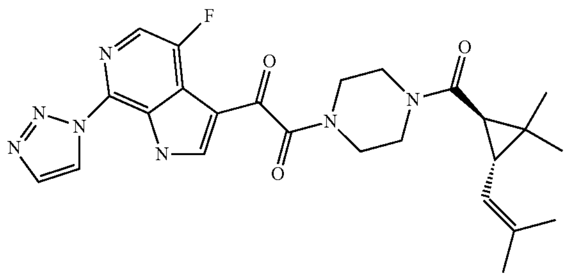 [SMILES: CC(C)=C[C@@H]1[C@@H](C(=O)N2CCN(C(=O)C(=O)c3c[nH]c4c(-n5ccnn5)ncc(F)c34)CC2)C1(C)C] | 494.2 | 494.2 | 7.99 | 1 |
| 2012 | 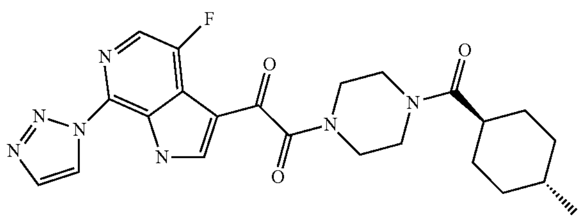 [SMILES: C[C@H]1CC[C@H](C(=O)N2CCN(C(=O)C(=O)c3c[nH]c4c(-n5ccnn5)ncc(F)c34)CC2)CC1] | 468.2 | 468.3 | 7.08 | 1 |
| 2013 | 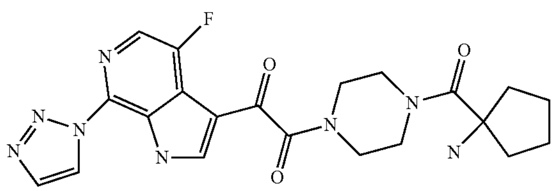 [SMILES: NC1(C(=O)N2CCN(C(=O)C(=O)c3c[nH]c4c(-n5ccnn5)ncc(F)c34)CC2)CCCC1] | 455.2 | 455.2 | 3.94 | 1 |
| 2014 | 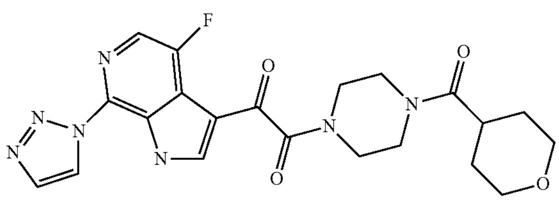 [SMILES: O=C(C(=O)N1CCN(C(=O)C2CCOCC2)CC1)c1c[nH]c2c(-n3ccnn3)ncc(F)c12] | 456.2 | 456.2 | 4.06 | 1 |
| 2015 | 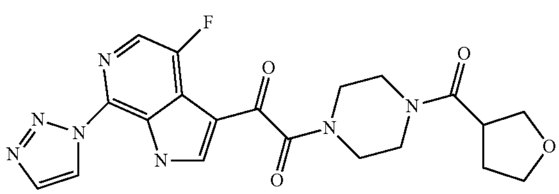 [SMILES: O=C(C(=O)N1CCN(C(=O)C2CCOC2)CC1)c1c[nH]c2c(-n3ccnn3)ncc(F)c12] | 442.2 | 442.2 | 3.95 | 1 |
| 2016 | 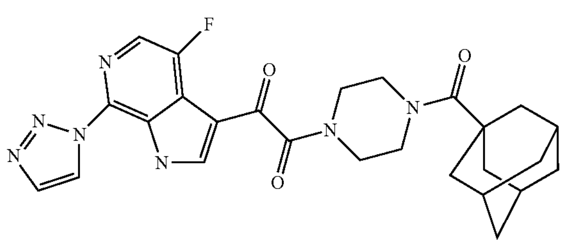 [SMILES: O=C(C(=O)N1CCN(C(=O)C23CC4CC(CC(C4)C2)C3)CC1)c1c[nH]c2c(-n3ccnn3)ncc(F)c12] | 506.2 | 506.3 | 8.12 | 1 |

-continued

| Cmpd # | Structure | MS (M + H)+ Calcd. | MS (M + H)+ Observ. | RT (min) | Method |
|---|---|---|---|---|---|
| 2017 | 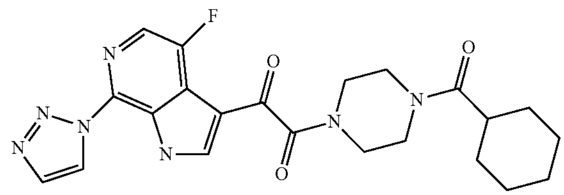 [SMILES: O=C(C(=O)N1CCN(C(=O)C2CCCCC2)CC1)c1c[nH]c2c(-n3ccnn3)ncc(F)c12] | 454.2 | 454.2 | 6.32 | 1 |
| 2018 | 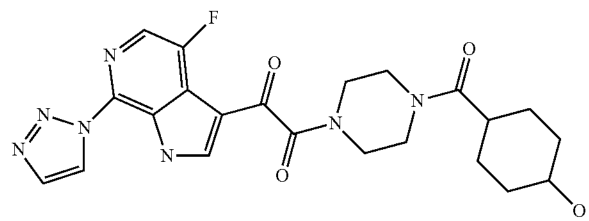 [SMILES: O=C(C(=O)N1CCN(C(=O)C2CCC(O)CC2)CC1)c1c[nH]c2c(-n3ccnn3)ncc(F)c12] | 470.2 | 470.2 | 3.97 | 1 |
| 2019 | 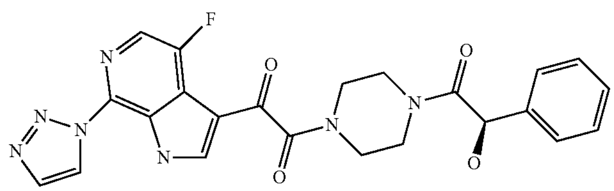 [SMILES: O=C(C(=O)N1CCN(C(=O)[C@H](O)c2ccccc2)CC1)c1c[nH]c2c(-n3ccnn3)ncc(F)c12] | 478.2 | 478.0 | 3.455 | 2 |
| 2020 | 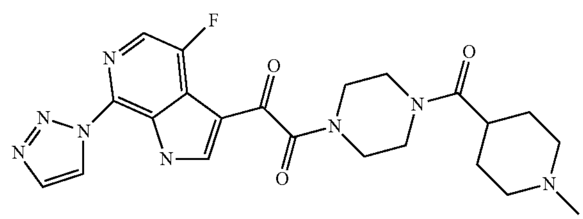 [SMILES: CN1CCC(C(=O)N2CCN(C(=O)C(=O)c3c[nH]c4c(-n5ccnn5)ncc(F)c34)CC2)CC1] | 469.2 | 469.1 | 2.351 | 2 |
| 2021 | 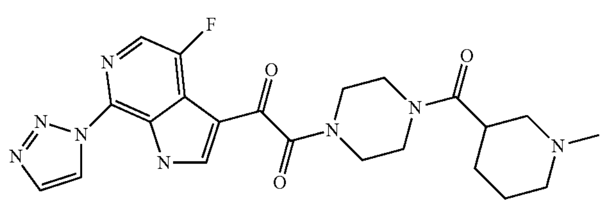 [SMILES: CN1CCCC(C(=O)N2CCN(C(=O)C(=O)c3c[nH]c4c(-n5ccnn5)ncc(F)c34)CC2)C1] | 469.2 | 469.0 | 2.397 | 2 |
| 2022 | 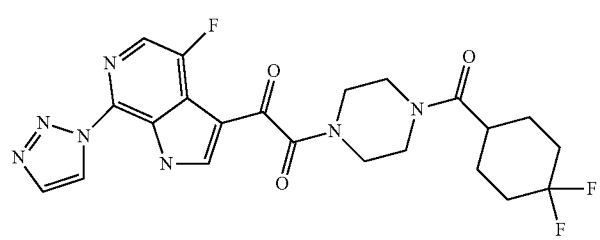 [SMILES: O=C(C(=O)N1CCN(C(=O)C2CCC(F)(F)CC2)CC1)c1c[nH]c2c(-n3ccnn3)ncc(F)c12] | 490.2 | 490.0 | 3.888 | 2 |
| 2023 | 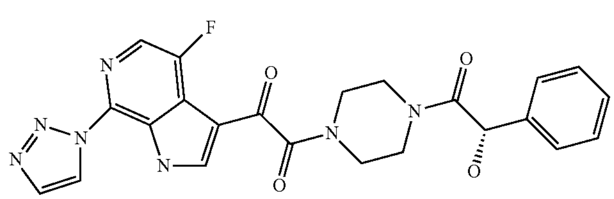 [SMILES: O=C(C(=O)N1CCN(C(=O)[C@@H](O)c2ccccc2)CC1)c1c[nH]c2c(-n3ccnn3)ncc(F)c12] | 478.2 | 478.0 | 3.451 | 2 |

-continued

| Cmpd # | Structure | MS (M+H)+ Calcd. | MS (M+H)+ Observ. | RT (min) | Method |
|---|---|---|---|---|---|
| 2024 | 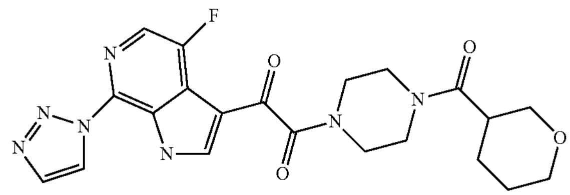 [SMILES: O=C(C(=O)N1CCN(C(=O)C2CCCOC2)CC1)c1c[nH]c2c(-n3ccnn3)ncc(F)c12] | 456.2 | 456.0 | 3.088 | 2 |
| 2025 | 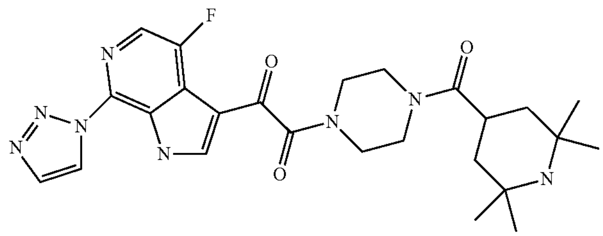 [SMILES: CC1(C)CC(C(=O)N2CCN(C(=O)C(=O)c3c[nH]c4c(-n5ccnn5)ncc(F)c34)CC2)CC(C)(C)N1] | 511.3 | 511.2 | 2.547 | 2 |
| 2026 | 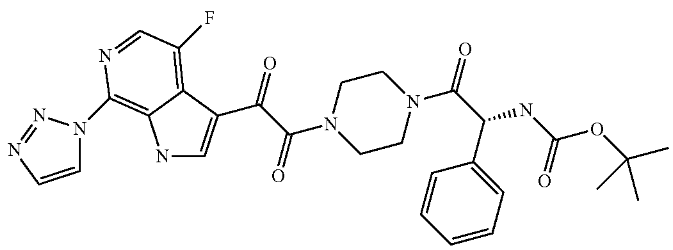 [SMILES: CC(C)(C)OC(=O)N[C@@H](C(=O)N1CCN(C(=O)C(=O)c2c[nH]c3c(-n4ccnn4)ncc(F)c23)CC1)c1ccccc1] | 577.2 | 577.2 | 4.58 | 2 |
| 2027 | 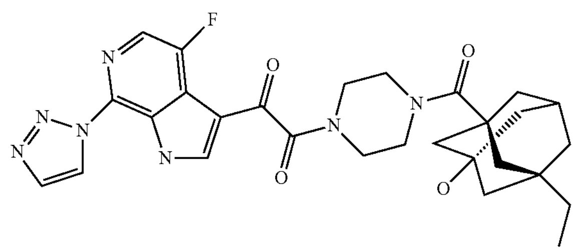 [SMILES: CC[C@@]12CC3C[C@@](O)(C1)C[C@](C(=O)N1CCN(C(=O)C(=O)c4c[nH]c5c(-n6ccnn6)ncc(F)c45)CC1)(C3)C2] | 550.3 | 550.2 | 3.792 | 2 |
| 2028 | 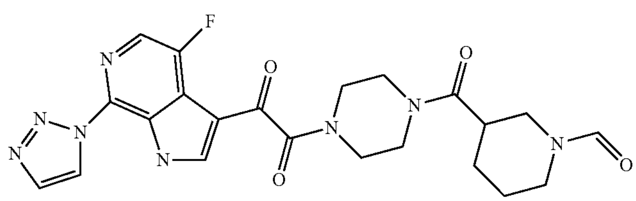 [SMILES: O=CN1CCCC(C(=O)N2CCN(C(=O)C(=O)c3c[nH]c4c(-n5ccnn5)ncc(F)c34)CC2)C1] | 483.2 | 483.1 | 2.805 | 2 |
| 2029 | 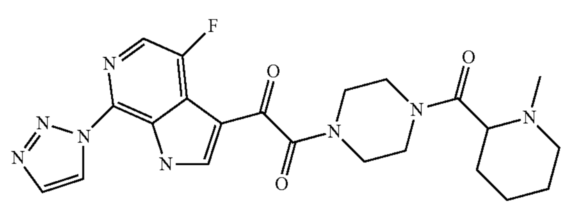 [SMILES: CN1CCCCC1C(=O)N1CCN(C(=O)C(=O)c2c[nH]c3c(-n4ccnn4)ncc(F)c23)CC1] | 469.2 | 469.1 | 2.547 | 2 |
| 2030 | 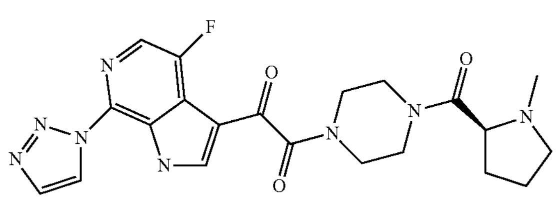 [SMILES: CN1CCC[C@H]1C(=O)N1CCN(C(=O)C(=O)c2c[nH]c3c(-n4ccnn4)ncc(F)c23)CC1] | 455.2 | 455.0 | 2.38 | 2 |

| Cmpd # | Structure | MS (M+H)+ Calcd. | MS (M+H)+ Observ. | RT (min) | Method |
|---|---|---|---|---|---|
| 2031 | 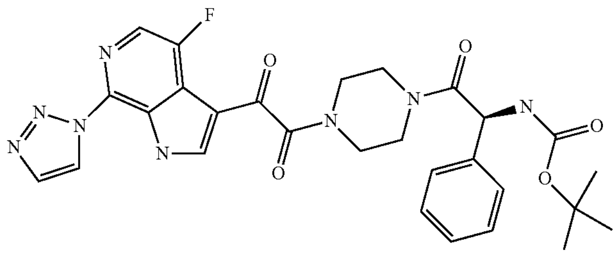 [SMILES: CC(C)(C)OC(=O)N[C@H](C(=O)N1CCN(C(=O)C(=O)c2c[nH]c3c(-n4ccnn4)ncc(F)c23)CC1)c1ccccc1] | 577.2 | 577.2 | 4.572 | 2 |
| 2032 | 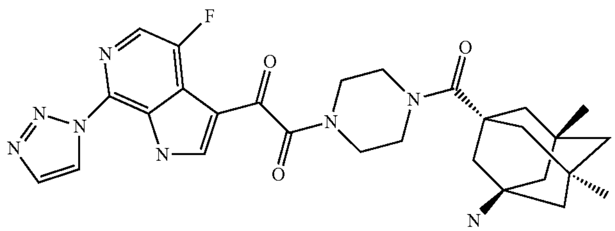 [SMILES: C[C@]12C[C@]3(C)C[C@](N)(C1)C[C@](C(=O)N1CCN(C(=O)C(=O)c4c[nH]c5c(-n6ccnn6)ncc(F)c45)CC1)(C2)C3] | 549.3 | 549.2 | 2.98 | 2 |
| 2033 | 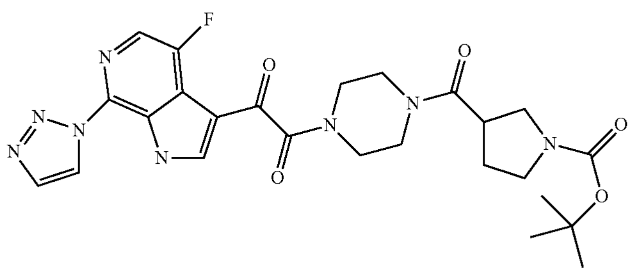 [SMILES: CC(C)(C)OC(=O)N1CCC(C(=O)N2CCN(C(=O)C(=O)c3c[nH]c4c(-n5ccnn5)ncc(F)c34)CC2)C1] | 541.2 | 541.2 | 3.93 | 2 |
| 2034 | 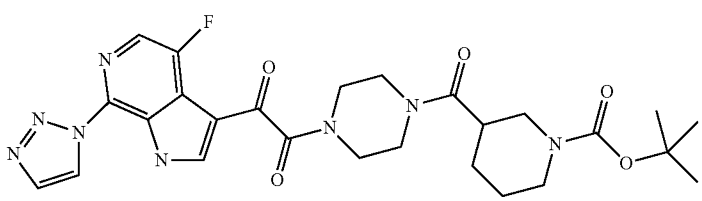 [SMILES: CC(C)(C)OC(=O)N1CCCC(C(=O)N2CCN(C(=O)C(=O)c3c[nH]c4c(-n5ccnn5)ncc(F)c34)CC2)C1] | 555.3 | 555.2 | 4.126 | 2 |
| 2035 | 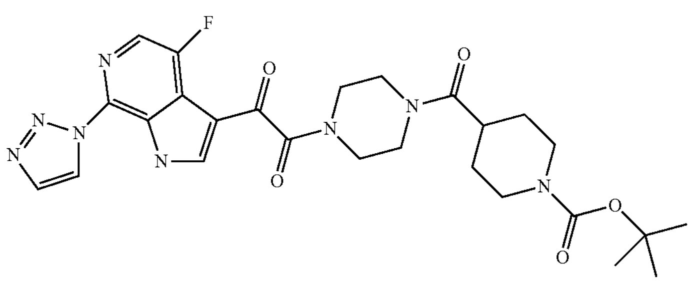 [SMILES: CC(C)(C)OC(=O)N1CCC(C(=O)N2CCN(C(=O)C(=O)c3c[nH]c4c(-n5ccnn5)ncc(F)c34)CC2)CC1] | 555.3 | 555.2 | 4.022 | 2 |
| 2036 | 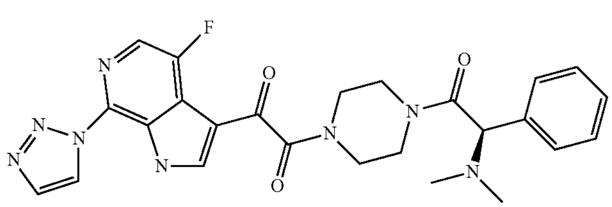 [SMILES: CN(C)[C@@H](C(=O)N1CCN(C(=O)C(=O)c2c[nH]c3c(-n4ccnn4)ncc(F)c23)CC1)c1ccccc1] | 505.2 | 505.1 | 3.163 | 2 |

-continued

| Cmpd # | Structure | MS (M + H)+ Calcd. | MS (M + H)+ Observ. | RT (min) | Method |
|---|---|---|---|---|---|
| 2037 | 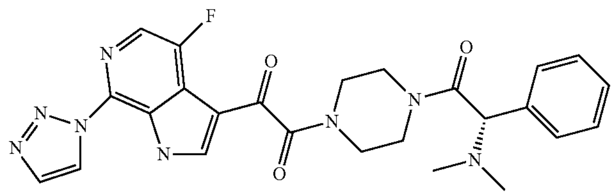 [SMILES: CN(C)[C@H](C(=O)N1CCN(C(=O)C(=O)c2c[nH]c3c(-n4ccnn4)ncc(F)c23)CC1)c1ccccc1] | 505.2 | 505.1 | 3.159 | 2 |
| 2038 | 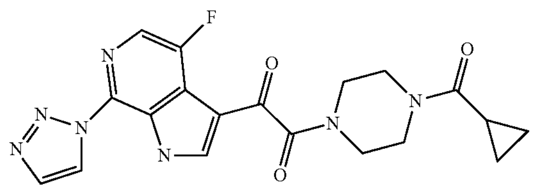 [SMILES: O=C(C(=O)N1CCN(C(=O)C2CC2)CC1)c1c[nH]c2c(-n3ccnn3)ncc(F)c12] | 412.2 | 412.0 | 1.05 | 3 |
| 2039 | 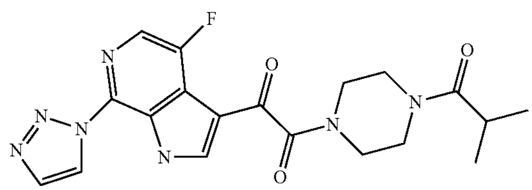 [SMILES: CC(C)C(=O)N1CCN(C(=O)C(=O)c2c[nH]c3c(-n4ccnn4)ncc(F)c23)CC1] | 414.2 | 414.1 | 1.17 | 3 |
| 2040 | 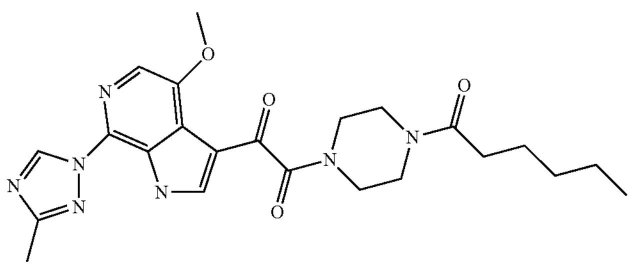 [SMILES: CCCCCC(=O)N1CCN(C(=O)C(=O)c2c[nH]c3c(-n4cnc(C)n4)ncc(OC)c23)CC1] | 468.2 | 468.2 | 1.61 | 1 |
| 2041 | 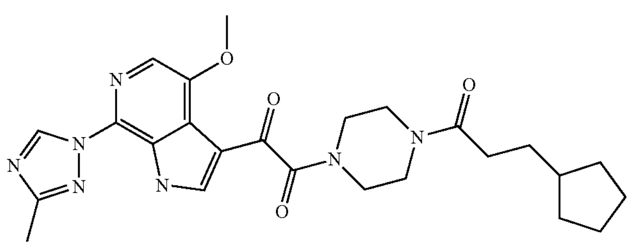 [SMILES: COc1cnc(-n2cnc(C)n2)c2[nH]cc(C(=O)C(=O)N3CCN(C(=O)CCC4CCCC4)CC3)c12] | 494.3 | 494.3 | 1.7 | 1 |
| 2042 | 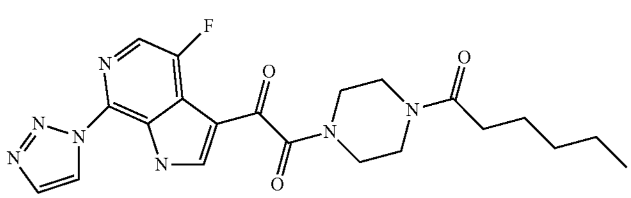 [SMILES: CCCCCC(=O)N1CCN(C(=O)C(=O)c2c[nH]c3c(-n4ccnn4)ncc(F)c23)CC1] | 442.2 | 442.2 | 1.58 | 1 |
| 2043 | 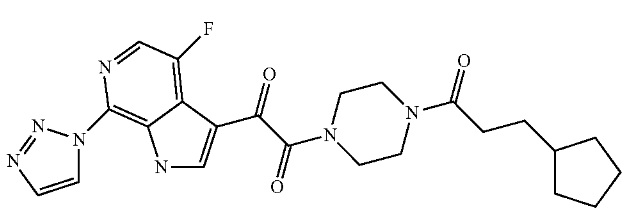 [SMILES: O=C(C(=O)N1CCN(C(=O)CCC2CCCC2)CC1)c1c[nH]c2c(-n3ccnn3)ncc(F)c12] | 468.2 | 468.2 | 1.66 | 1 |

| Cmpd # | Structure | MS (M + H)+ Calcd. | MS (M + H)+ Observ. | RT (min) | Method |
|---|---|---|---|---|---|
| 2044 | 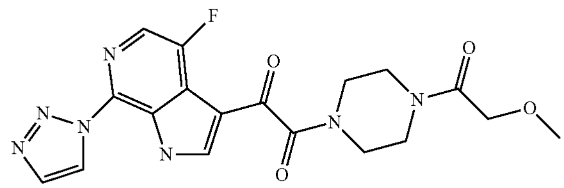 [SMILES: COCC(=O)N1CCN(C(=O)C(=O)c2c[nH]c3c(-n4ccnn4)ncc(F)c23)CC1] | 416.2 | 416.2 | 1.26 | 1 |
| 2045 | 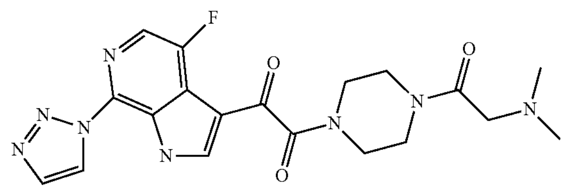 [SMILES: CN(C)CC(=O)N1CCN(C(=O)C(=O)c2c[nH]c3c(-n4ccnn4)ncc(F)c23)CC1] | 429.2 | 429.2 | 1.13 | 1 |
| 2046 | 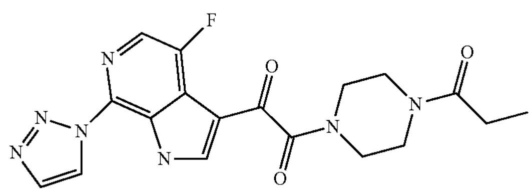 [SMILES: CCC(=O)N1CCN(C(=O)C(=O)c2c[nH]c3c(-n4ccnn4)ncc(F)c23)CC1] | 400.2 | 400.2 | 1.29 | 1 |
| 2047 | 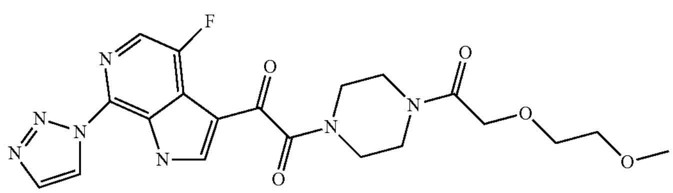 [SMILES: COCCOCC(=O)N1CCN(C(=O)C(=O)c2c[nH]c3c(-n4ccnn4)ncc(F)c23)CC1] | 460.2 | 460.2 | 1.27 | 1 |
| 2048 | 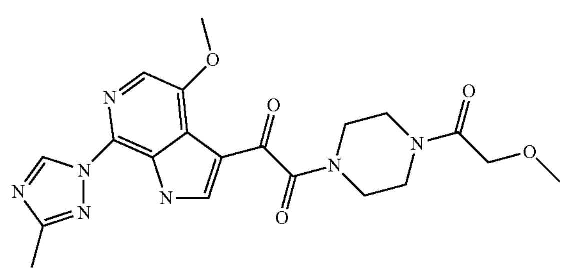 [SMILES: COCC(=O)N1CCN(C(=O)C(=O)c2c[nH]c3c(-n4cnc(C)n4)ncc(OC)c23)CC1] | 442.2 | 442.3 | 4.015 | 1 |
| 2049 | 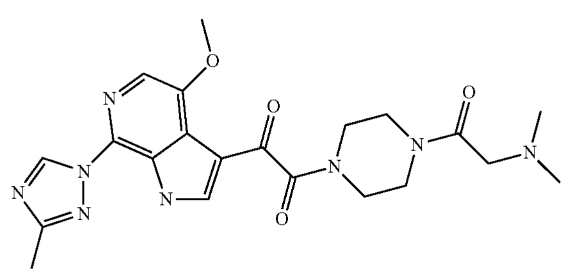 [SMILES: COc1cnc(-n2cnc(C)n2)c2[nH]cc(C(=O)C(=O)N3CCN(C(=O)CN(C)C)CC3)c12] | 455.2 | 455.3 | 3.868 | 1 |

| Cmpd # | Structure | MS (M + H)+ Calcd. | MS (M + H)+ Observ. | RT (min) | Method |
|---|---|---|---|---|---|
| 2050 | 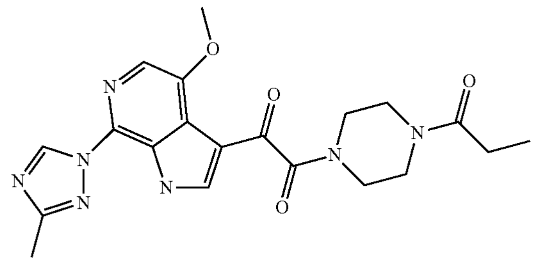 [SMILES: CCC(=O)N1CCN(C(=O)C(=O)c2c[nH]c3c(-n4cnc(C)n4)ncc(OC)c23)CC1] | 426.2 | 426.3 | 4.437 | 1 |
| 2051 | 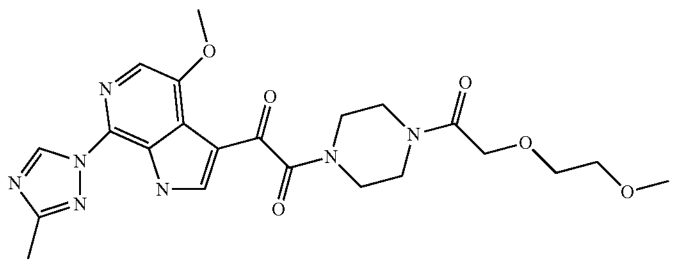 [SMILES: COCCOCC(=O)N1CCN(C(=O)C(=O)c2c[nH]c3c(-n4cnc(C)n4)ncc(OC)c23)CC1] | 486.2 | 486.3 | 4.213 | 1 |

Biology Data for the Examples

"µM" means micromolar;
"mL" means milliliter;
"µl" means microliter;
"mg" means milligram;

The materials and experimental procedures used to obtain the results reported in Table 2 are described below.

Cells:
Virus production—Human embryonic Kidney cell line, 293T (HEK 293T), was propagated in Dulbecco's Modified Eagle Medium (Invitrogen, Carlsbad, Calif.) containing 10% fetal Bovine serum (FBS, Sigma, St. Louis, Mo.). The human T-cell leukemia cell MT2 (AIDS Research and Reference Reagent Program, Cat. 237) was propagated in RPMI 1640 (Invitrogen, Carlsbad, Calif.) containing 10% fetal bovine serum (FBS, Hyclone, Logan, Utah)

Virus infection—Single-round infectious reporter virus was produced by co-transfecting HEK 293T cells with plasmide expressing the HIV-1 LAI envelope along with a plasmid containing an HIV-1 LAI proviral cDNA with the envelope gene replaced by a firefly luciferase reporter gene (Chen et al, Ref 41). Transfections were performed using lipofectAMINE PLUS reagent as described by the manufacturer (Invitrogen, Carlsbad, Calif.).

Experimental Procedure

1. MT2 cells were plated in black, 384 well plates at a cell density of $5 \times 10^3$ cells per well in 25 µl RPMI 1640 containing 10% FBS.
2. Compound (diluted in dimethylsulfoxide and growth medium) was added to cells at 12.5 µl/well, so that the final assay concentration would be ≤50 nM.
3. 12.5 µl of single-round infectious reporter virus in Dulbecco's Modified Eagle Medium was added to the plated cells and compound at an approximate multiplicity of infection (MOI) of 0.01, resulting in a final volume of 50 µl per well.
4. Virus-infected cells were incubated at 37 degrees Celsius, in a $CO_2$ incubator, and harvested 72 h after infection.
5. Viral infection was monitored by measuring luciferase expression in the infected cells using a luciferase reporter gene assay kit (Steady-Glo, Promega, Madison, Wis.) as described by the manufacturer. Luciferase activity was then quantified by measuring luminescence using an EnVision Multilabel Plate Readers (PerkinElmer, Waltham, Mass.).
6. The percent inhibition for each compound was calculated by quantifying the level of luciferase expression in cells infected in the presence of each compound as a percentage of that observed for cells infected in the absence of compound and subtracting such a determined value from 100.
7. An $EC_{50}$ provides a method for comparing the antiviral potency of the compounds of this disclosure. The effective concentration for fifty percent inhibition ($EC_{50}$) was calculated with the Microsoft Excel Xlfit curve fitting software. For each compound, curves were generated from percent inhibition calculated at 10 different concentrations by using a four paramenter logistic model (model 205). The $EC_{50}$ data for the compounds is shown in Table 2. Table 1 is the key for the data in Table 2.

TABLE 1

Biological Data Key for $EC_{50}$s

| Compounds with $EC_{50}$s >0.5 µM | Compounds with $EC_{50}$ <0.5 µM |
|---|---|
| Group B | Group A |

TABLE 2

| Compd. Number | Structure | EC$_{50}$ Group from Table 1 |
|---|---|---|
| 1001 | 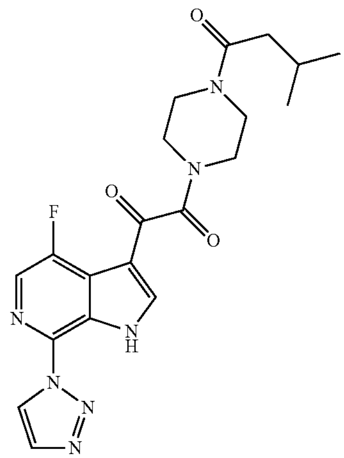 [SMILES: CC(C)CC(=O)N1CCN(C(=O)C(=O)c2c[nH]c3c(-n4ccnn4)ncc(F)c23)CC1] | A |
| 1002 | 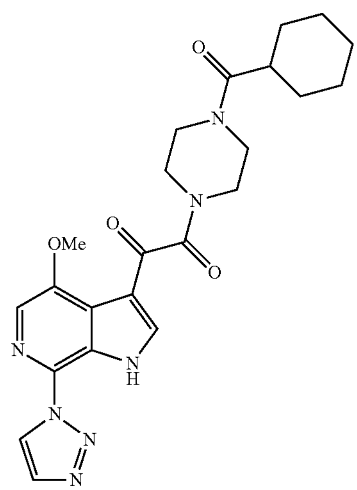 [SMILES: COc1cnc(-n2ccnn2)c2[nH]cc(C(=O)C(=O)N3CCN(C(=O)C4CCCCC4)CC3)c12] | A |
| 1003 | 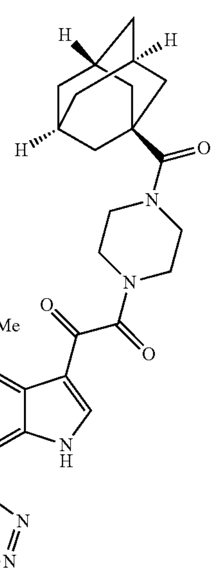 | A |

TABLE 2-continued

| Compd. Number | Structure | EC$_{50}$ Group from Table 1 |
|---|---|---|
| 1004 | 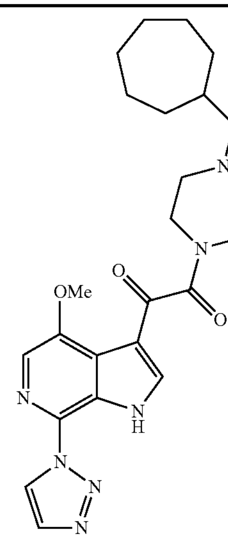 | A<br>0.14 nM |
| 2001 | 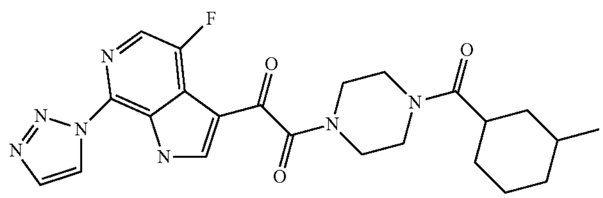 [SMILES: CC1CCCC(C(=O)N2CCN(C(=O)C(=O)c3c[nH]c4c(-n5ccnn5)ncc(F)c34)CC2)C1] | A |
| 2002 | 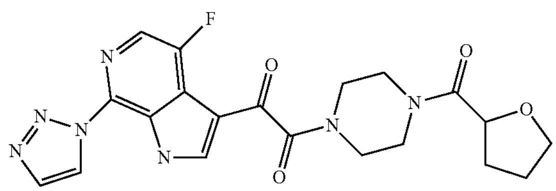 [SMILES: O=C(C(=O)N1CCN(C(=O)C2CCCO2)CC1)c1c[nH]c2c(-n3ccnn3)ncc(F)c12] | A |
| 2003 | 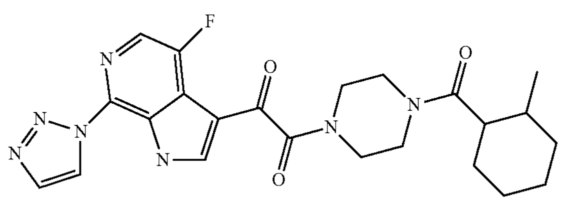 | A |
| 2004 | 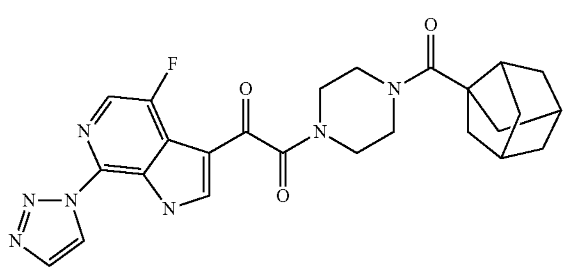 [SMILES: O=C(C(=O)N1CCN(C(=O)C23CC4CC(CC2C4)C3)CC1)c1c[nH]c2c(-n3ccnn3)ncc(F)c12] | A<br>1.15 nM |
| 2005 | 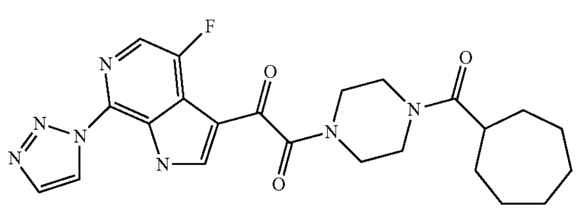 [SMILES: O=C(C(=O)N1CCN(C(=O)C2CCCCCC2)CC1)c1c[nH]c2c(-n3ccnn3)ncc(F)c12] | A<br>0.36 nM |

TABLE 2-continued

| Compd. Number | Structure | EC$_{50}$ Group from Table 1 |
|---|---|---|
| 2006 | 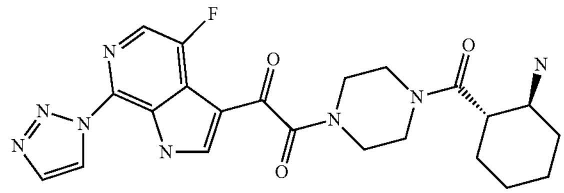 [SMILES: N[C@H]1CCCC[C@@H]1C(=O)N1CCN(C(=O)C(=O)c2c[nH]c3c(-n4ccnn4)ncc(F)c23)CC1] | B |
| 2007 | 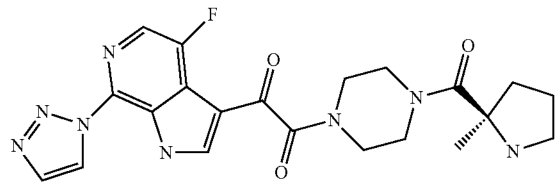 [SMILES: C[C@]1(C(=O)N2CCN(C(=O)C(=O)c3c[nH]c4c(-n5ccnn5)ncc(F)c34)CC2)CCCN1] | B |
| 2008 | 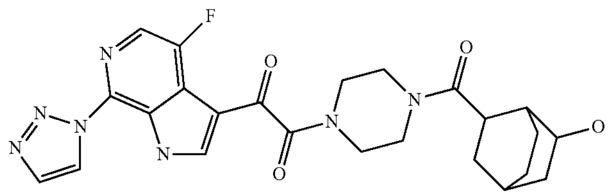 [SMILES: O=C(C(=O)N1CCN(C(=O)C2CC3CCC2C(O)C3)CC1)c1c[nH]c2c(-n3ccnn3)ncc(F)c12] | A<br>5.1 nM |
| 2009 | 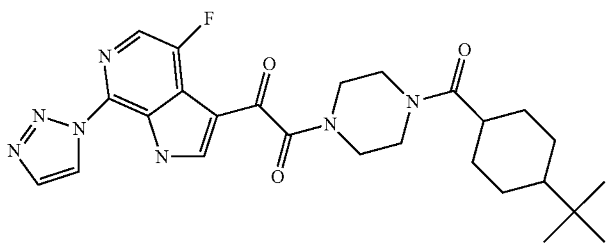 [SMILES: CC(C)(C)C1CCC(C(=O)N2CCN(C(=O)C(=O)c3c[nH]c4c(-n5ccnn5)ncc(F)c34)CC2)CC1] | B |
| 2010 | 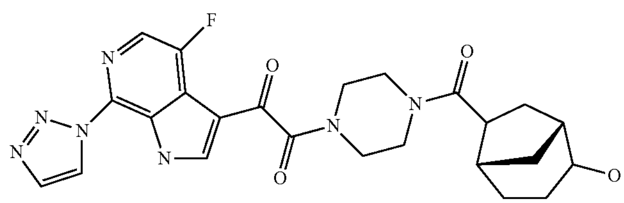 [SMILES: O=C(C(=O)N1CCN(C(=O)C2C[C@H]3C[C@@H]2CCC3O)CC1)c1c[nH]c2c(-n3ccnn3)ncc(F)c12] | A |
| 2011 | 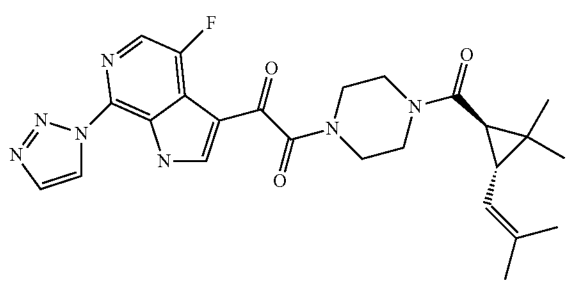 [SMILES: CC(C)=C[C@@H]1[C@@H](C(=O)N2CCN(C(=O)C(=O)c3c[nH]c4c(-n5ccnn5)ncc(F)c34)CC2)C1(C)C] | B |
| 2012 | 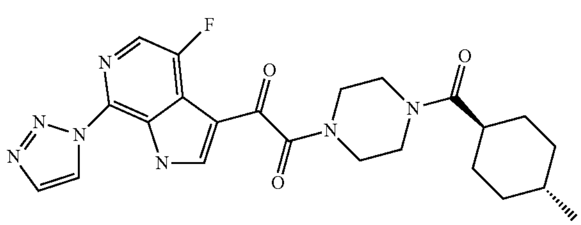 [SMILES: C[C@H]1CC[C@H](C(=O)N2CCN(C(=O)C(=O)c3c[nH]c4c(-n5ccnn5)ncc(F)c34)CC2)CC1] | A |

TABLE 2-continued

| Compd. Number | Structure | EC$_{50}$ Group from Table 1 |
|---|---|---|
| 2013 | 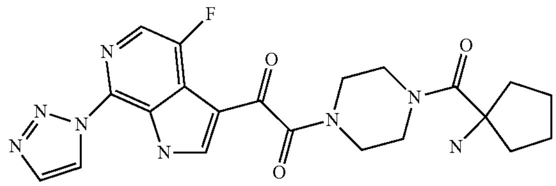 [SMILES: NC1(C(=O)N2CCN(C(=O)C(=O)c3c[nH]c4c(-n5ccnn5)ncc(F)c34)CC2)CCCC1] | A<br>450.6 nM |
| 2014 | 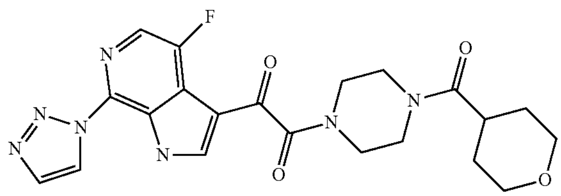 [SMILES: O=C(C(=O)N1CCN(C(=O)C2CCOCC2)CC1)c1c[nH]c2c(-n3ccnn3)ncc(F)c12] | A<br>12.5 nM |
| 2015 | 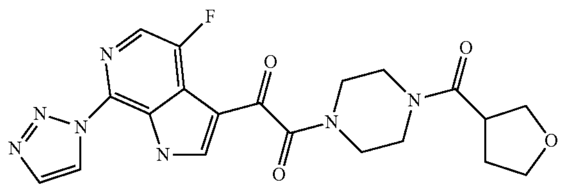 [SMILES: O=C(C(=O)N1CCN(C(=O)C2CCOC2)CC1)c1c[nH]c2c(-n3ccnn3)ncc(F)c12] | A |
| 2016 | 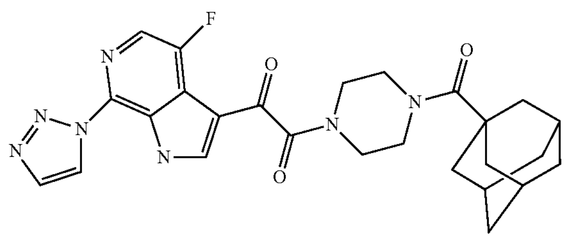 [SMILES: O=C(C(=O)N1CCN(C(=O)C23CC4CC(CC(C4)C2)C3)CC1)c1c[nH]c2c(-n3ccnn3)ncc(F)c12] | A |
| 2017 | 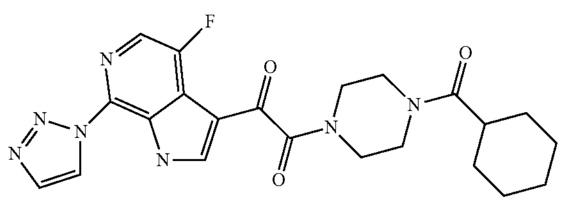 | A<br>0.11 nM |
| 2018 | 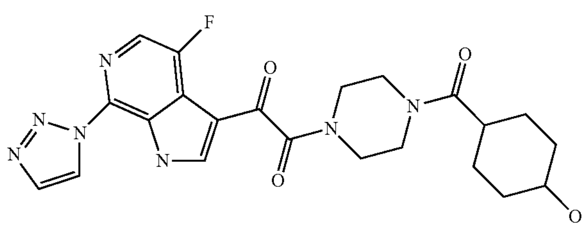 [SMILES: O=C(C(=O)N1CCN(C(=O)C2CCC(O)CC2)CC1)c1c[nH]c2c(-n3ccnn3)ncc(F)c12] | A |
| 2019 | 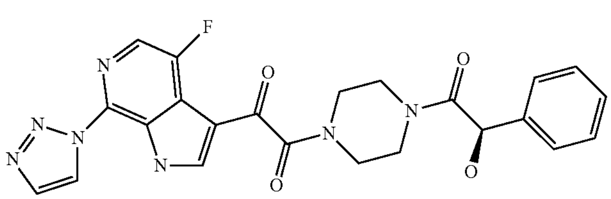 [SMILES: O=C(C(=O)N1CCN(C(=O)[C@H](O)c2ccccc2)CC1)c1c[nH]c2c(-n3ccnn3)ncc(F)c12] | A<br>344.4 nM |

TABLE 2-continued

| Compd. Number | Structure | EC$_{50}$ Group from Table 1 |
|---|---|---|
| 2020 | 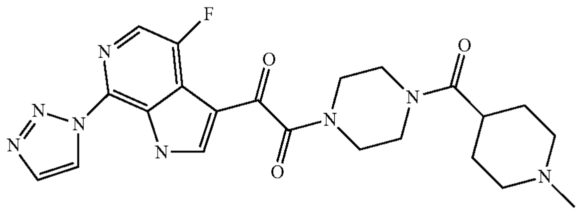 [SMILES: CN1CCC(C(=O)N2CCN(C(=O)C(=O)c3c[nH]c4c(-n5ccnn5)ncc(F)c34)CC2)CC1] | B |
| 2021 | 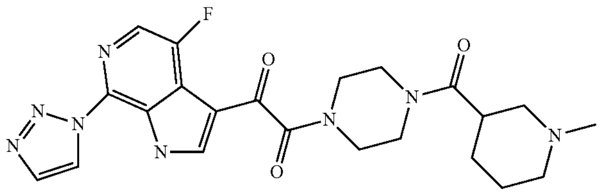 | A<br>76.9 nM |
| 2022 | 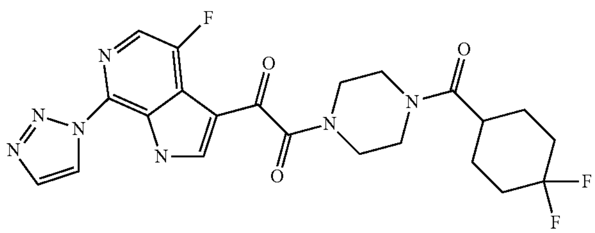 [SMILES: O=C(C(=O)N1CCN(C(=O)C2CCC(F)(F)CC2)CC1)c1c[nH]c2c(-n3ccnn3)ncc(F)c12] | A |
| 2023 | 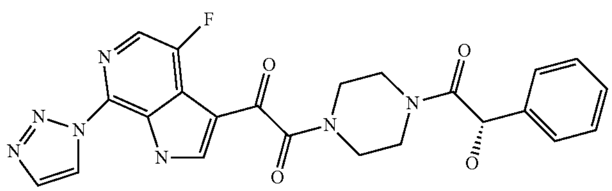 [SMILES: O=C(C(=O)N1CCN(C(=O)[C@@H](O)c2ccccc2)CC1)c1c[nH]c2c(-n3ccnn3)ncc(F)c12] | A |
| 2024 | 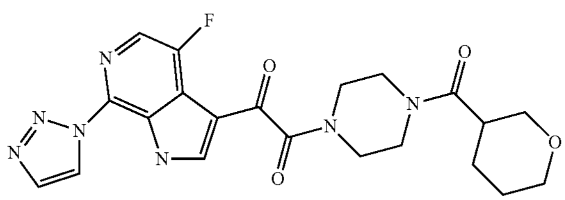 [SMILES: O=C(C(=O)N1CCN(C(=O)C2CCCOC2)CC1)c1c[nH]c2c(-n3ccnn3)ncc(F)c12] | A |
| 2025 | 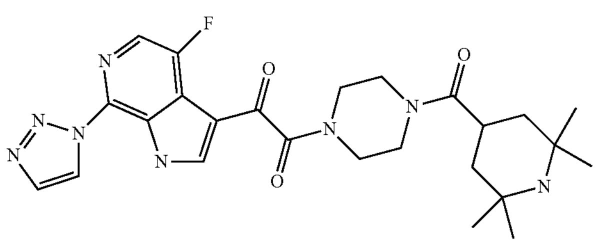 [SMILES: CC1(C)CC(C(=O)N2CCN(C(=O)C(=O)c3c[nH]c4c(-n5ccnn5)ncc(F)c34)CC2)CC(C)(C)N1] | B |
| 2026 | 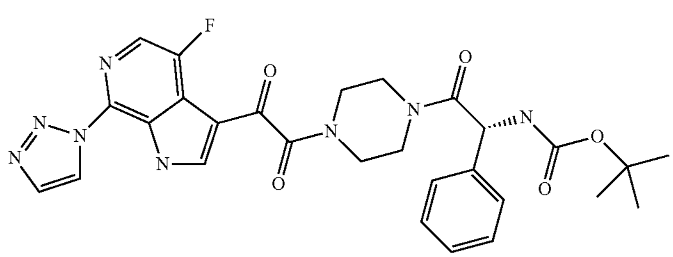 [SMILES: CC(C)(C)OC(=O)N[C@@H](C(=O)N1CCN(C(=O)C(=O)c2c[nH]c3c(-n4ccnn4)ncc(F)c23)CC1)c1ccccc1] | B |

TABLE 2-continued

| Compd. Number | Structure | EC$_{50}$ Group from Table 1 |
|---|---|---|
| 2027 | 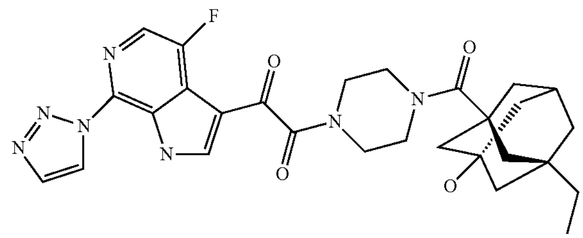 [SMILES: CC[C@@]12CC3C[C@@](O)(C1)C[C@](C(=O)N1CCN(C(=O)C(=O)c4c[nH]c5c(-n6ccnn6)ncc(F)c45)CC1)(C3)C2] | A |
| 2028 | 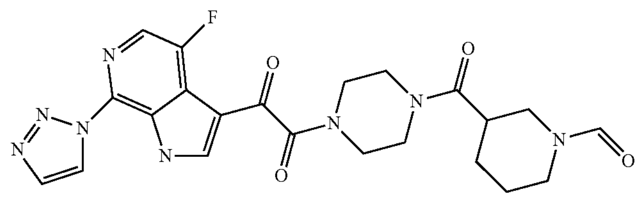 [SMILES: O=CN1CCCC(C(=O)N2CCN(C(=O)C(=O)c3c[nH]c4c(-n5ccnn5)ncc(F)c34)CC2)C1] | A<br>25.5 nM |
| 2029 | 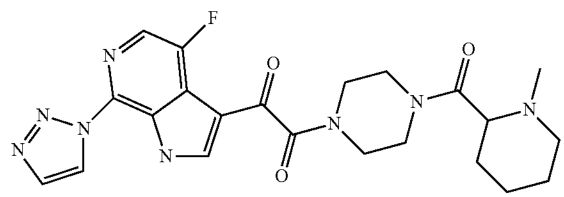 [SMILES: CN1CCCCC1C(=O)N1CCN(C(=O)C(=O)c2c[nH]c3c(-n4ccnn4)ncc(F)c23)CC1] | B |
| 2030 | 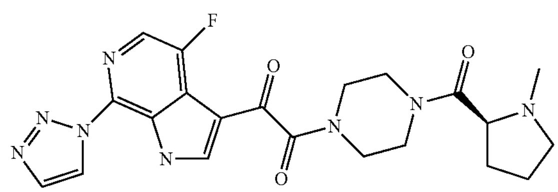 [SMILES: CN1CCC[C@H]1C(=O)N1CCN(C(=O)C(=O)c2c[nH]c3c(-n4ccnn4)ncc(F)c23)CC1] | B |
| 2031 | 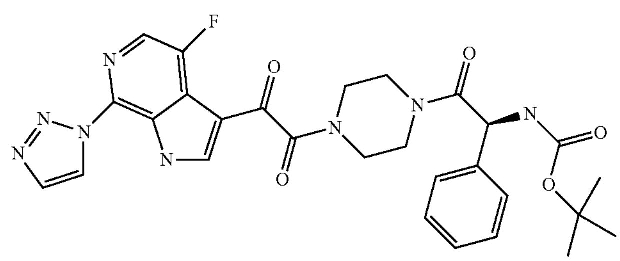 [SMILES: CC(C)(C)OC(=O)N[C@H](C(=O)N1CCN(C(=O)C(=O)c2c[nH]c3c(-n4ccnn4)ncc(F)c23)CC1)c1ccccc1] | B |
| 2032 | 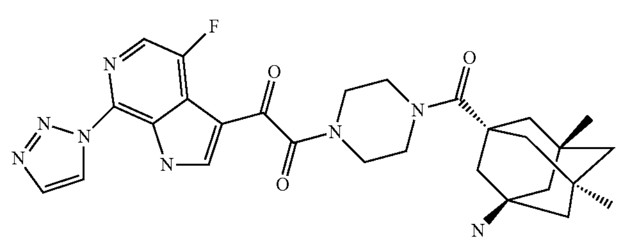 [SMILES: C[C@]12C[C@]3(C)C[C@](N)(C1)C[C@](C(=O)N1CCN(C(=O)C(=O)c4c[nH]c5c(-n6ccnn6)ncc(F)c45)CC1)(C2)C3] | B |

TABLE 2-continued

| Compd. Number | Structure | EC$_{50}$ Group from Table 1 |
|---|---|---|
| 2033 | 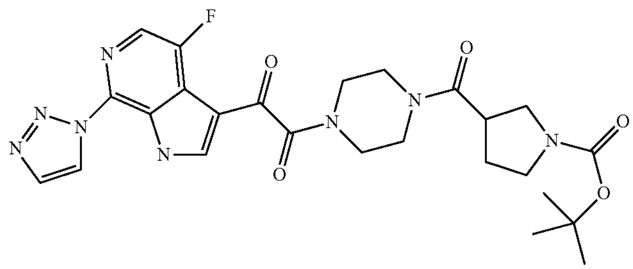 [SMILES: CC(C)(C)OC(=O)N1CCC(C(=O)N2CCN(C(=O)C(=O)c3c[nH]c4c(-n5ccnn5)ncc(F)c34)CC2)C1] | B |
| 2034 | 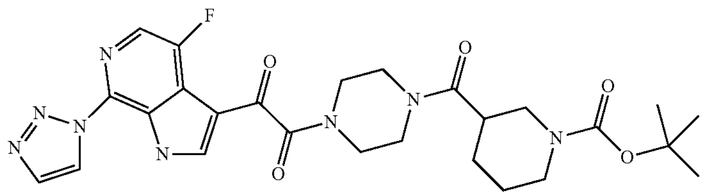 [SMILES: CC(C)(C)OC(=O)N1CCCC(C(=O)N2CCN(C(=O)C(=O)c3c[nH]c4c(-n5ccnn5)ncc(F)c34)CC2)C1] | B |
| 2035 | 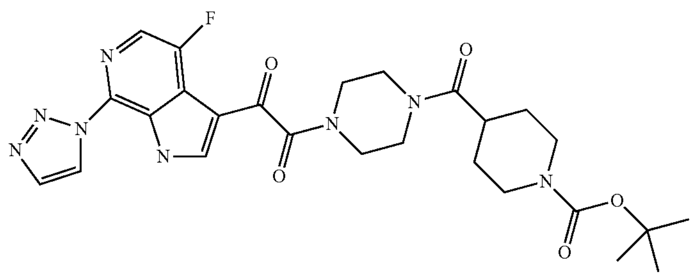 [SMILES: CC(C)(C)OC(=O)N1CCC(C(=O)N2CCN(C(=O)C(=O)c3c[nH]c4c(-n5ccnn5)ncc(F)c34)CC2)CC1] | B |
| 2036 | 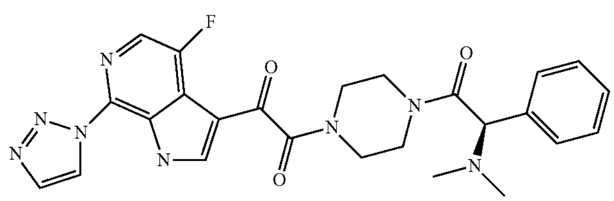 [SMILES: CN(C)[C@@H](C(=O)N1CCN(C(=O)C(=O)c2c[nH]c3c(-n4ccnn4)ncc(F)c23)CC1)c1ccccc1] | B |
| 2037 | 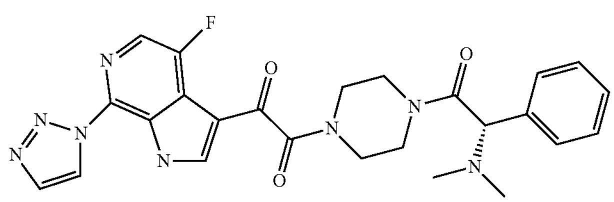 [SMILES: CN(C)[C@H](C(=O)N1CCN(C(=O)C(=O)c2c[nH]c3c(-n4ccnn4)ncc(F)c23)CC1)c1ccccc1] | B |
| 2038 | 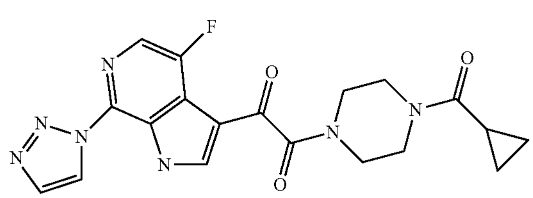 [SMILES: O=C(C(=O)N1CCN(C(=O)C2CC2)CC1)c1c[nH]c2c(-n3ccnn3)ncc(F)c12] | A |
| 2039 | 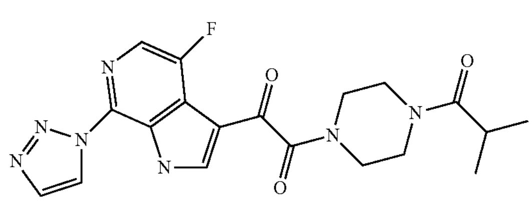 [SMILES: CC(C)C(=O)N1CCN(C(=O)C(=O)c2c[nH]c3c(-n4ccnn4)ncc(F)c23)CC1] | A |

TABLE 2-continued

| Compd. Number | Structure | EC$_{50}$ Group from Table 1 |
|---|---|---|
| 2040 | 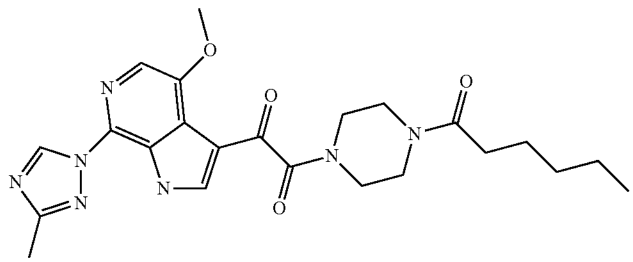 [SMILES: CCCCCC(=O)N1CCN(C(=O)C(=O)c2c[nH]c3c(-n4cnc(C)n4)ncc(OC)c23)CC1] | A |
| 2041 | 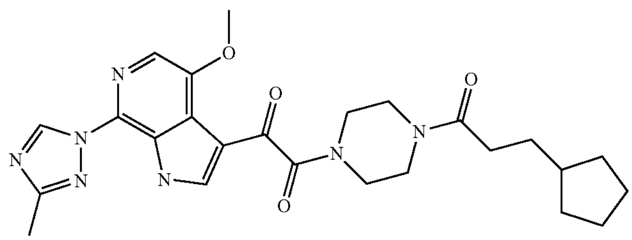 [SMILES: COc1cnc(-n2cnc(C)n2)c2[nH]cc(C(=O)C(=O)N3CCN(C(=O)CCC4CCCC4)CC3)c12] | A |
| 2042 | 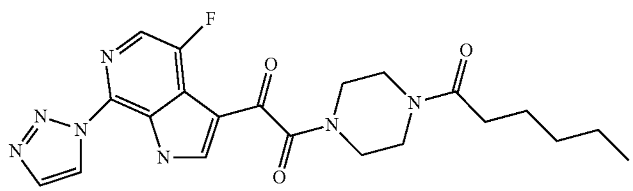 [SMILES: CCCCCC(=O)N1CCN(C(=O)C(=O)c2c[nH]c3c(-n4ccnn4)ncc(F)c23)CC1] | A |
| 2043 | 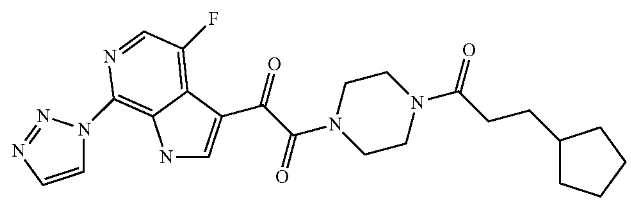 [SMILES: O=C(C(=O)N1CCN(C(=O)CCC2CCCC2)CC1)c1c[nH]c2c(-n3ccnn3)ncc(F)c12] | A |
| 2044 | 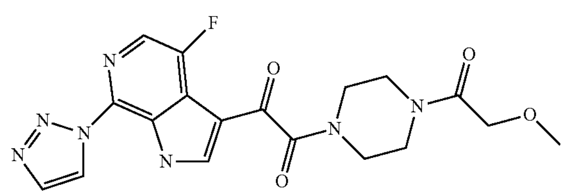 [SMILES: COCC(=O)N1CCN(C(=O)C(=O)c2c[nH]c3c(-n4ccnn4)ncc(F)c23)CC1] | A |
| 2045 | 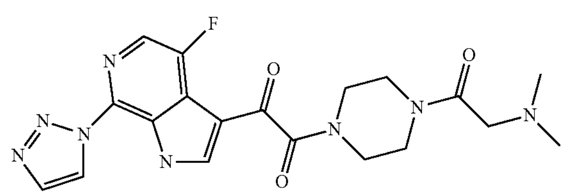 [SMILES: CN(C)CC(=O)N1CCN(C(=O)C(=O)c2c[nH]c3c(-n4ccnn4)ncc(F)c23)CC1] | B |
| 2046 | 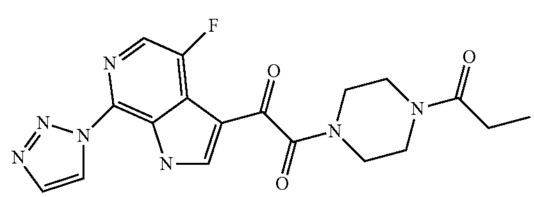 [SMILES: CCC(=O)N1CCN(C(=O)C(=O)c2c[nH]c3c(-n4ccnn4)ncc(F)c23)CC1] | A<br>6.88 nM |

TABLE 2-continued

| Compd. Number | Structure | EC$_{50}$ Group from Table 1 |
|---|---|---|
| 2047 | 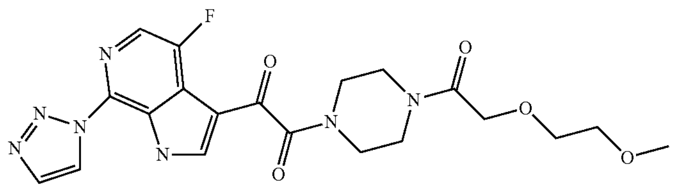 [SMILES: COCCOCC(=O)N1CCN(C(=O)C(=O)c2c[nH]c3c(-n4ccnn4)ncc(F)c23)CC1] | B |
| 2048 | 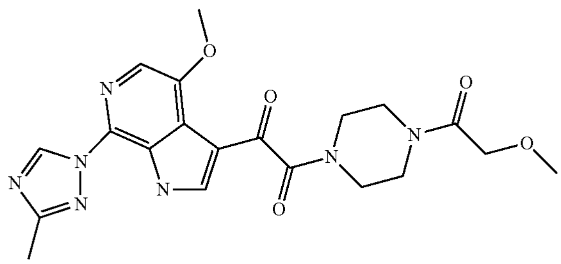 [SMILES: COCC(=O)N1CCN(C(=O)C(=O)c2c[nH]c3c(-n4cnc(C)n4)ncc(OC)c23)CC1] | A |
| 2049 | 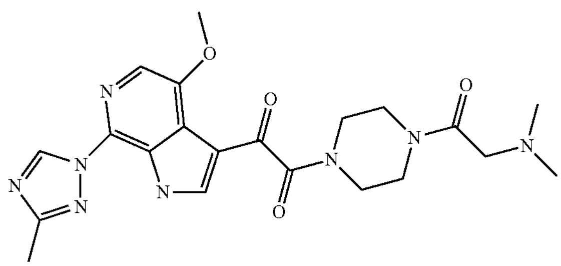 [SMILES: COc1cnc(-n2cnc(C)n2)c2[nH]cc(C(=O)C(=O)N3CCN(C(=O)CN(C)C)CC3)c12] | B |
| 2050 | 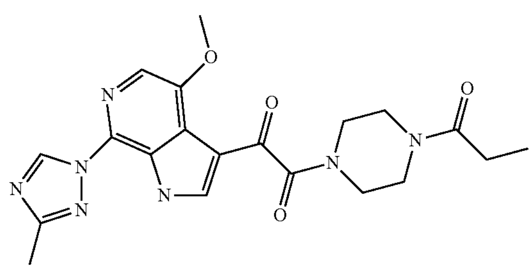 [SMILES: CCC(=O)N1CCN(C(=O)C(=O)c2c[nH]c3c(-n4cnc(C)n4)ncc(OC)c23)CC1] | A<br>10.4 nM |
| 2051 | 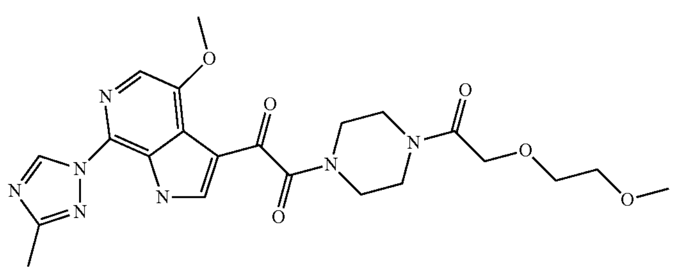 [SMILES: COCCOCC(=O)N1CCN(C(=O)C(=O)c2c[nH]c3c(-n4cnc(C)n4)ncc(OC)c23)CC1] | B |

The foregoing description is merely illustrative and should not be understood to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the appended claims.

What is claimed is:

1. A compound which is selected from the group of:

87
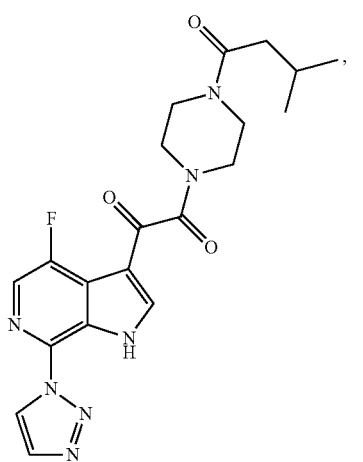
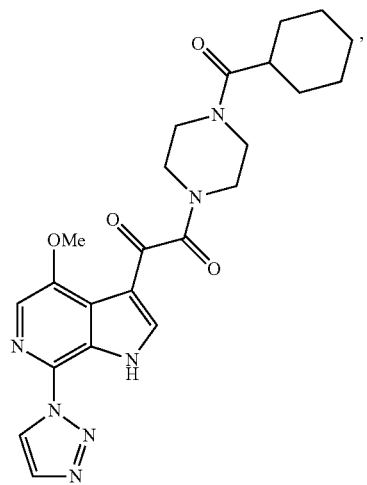
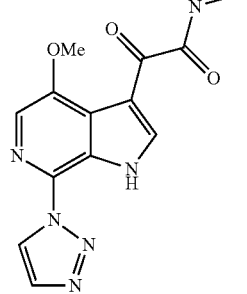
88
-continued
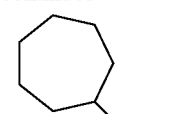
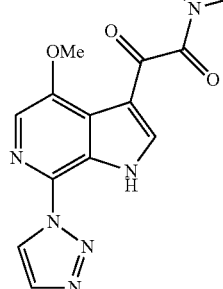
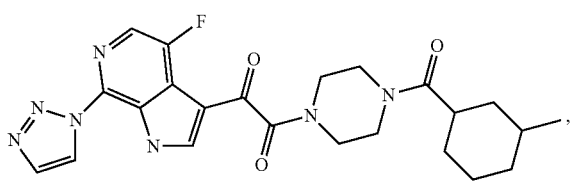
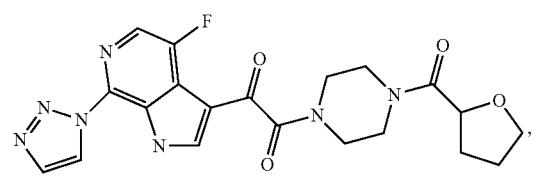
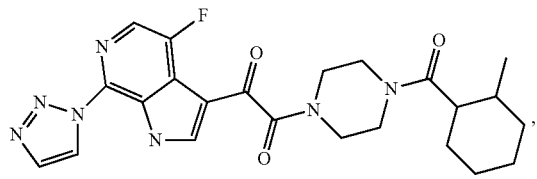
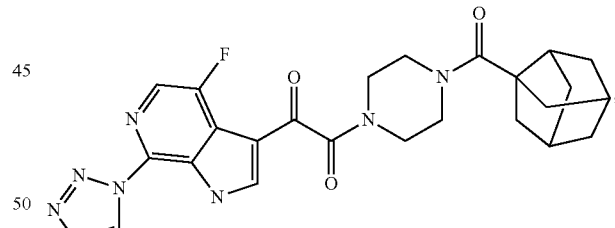
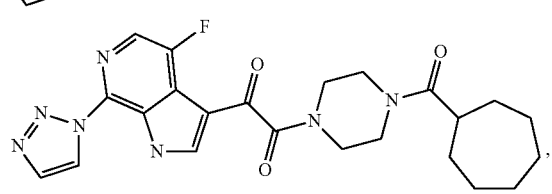
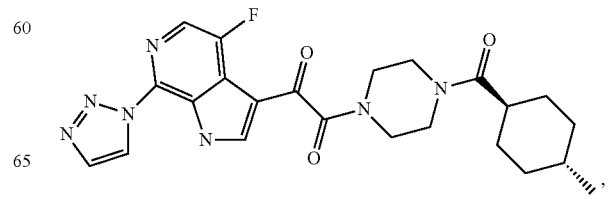

89
-continued
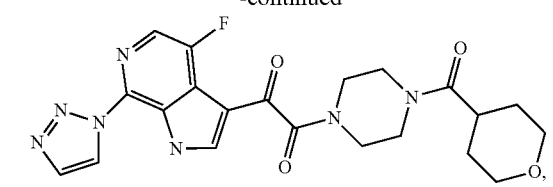
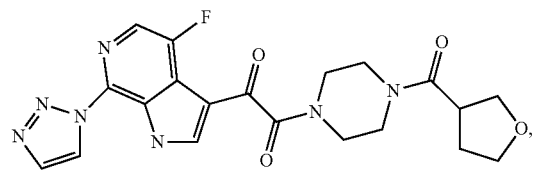
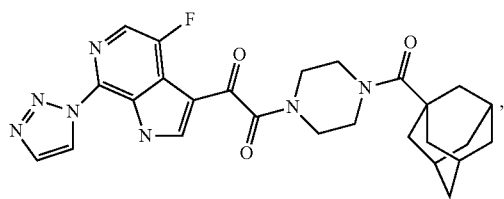
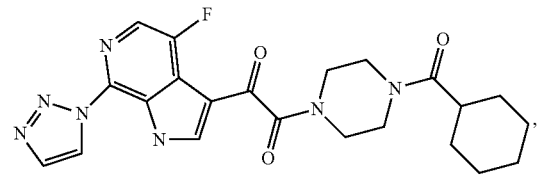
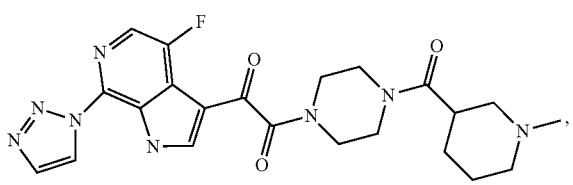
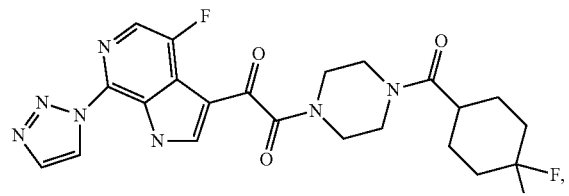
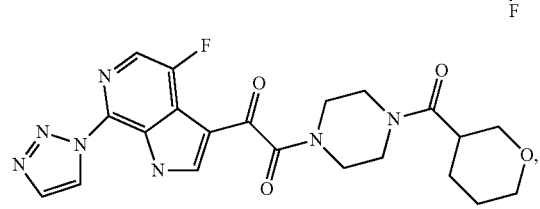
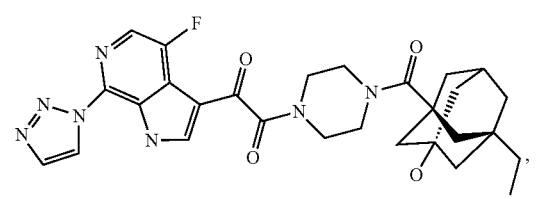
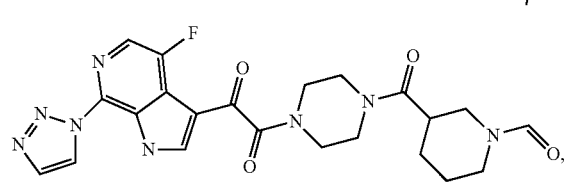
90
-continued
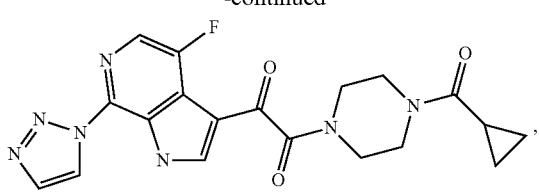
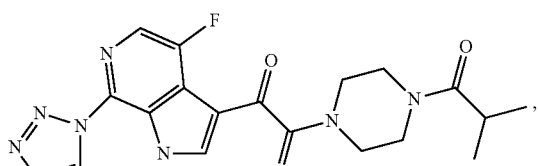
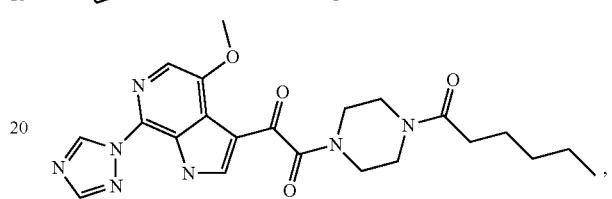
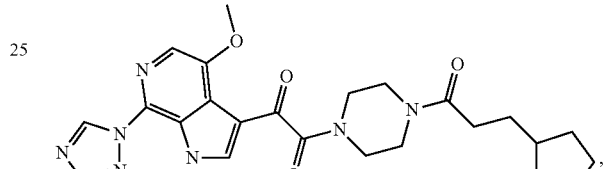
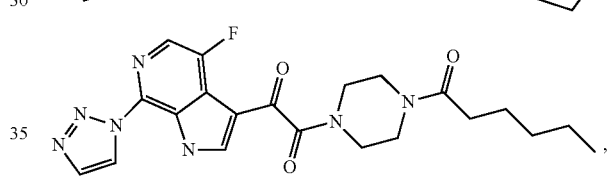
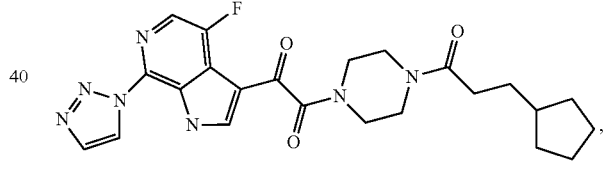
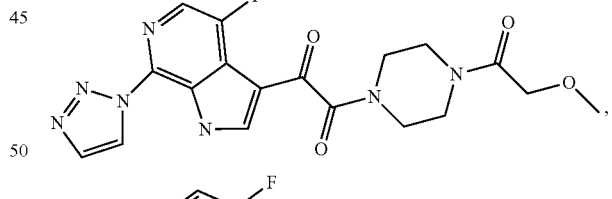
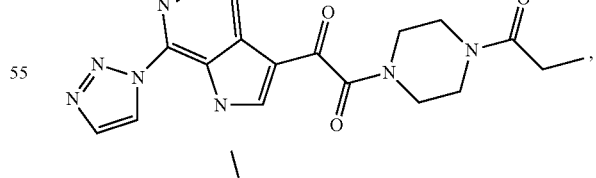
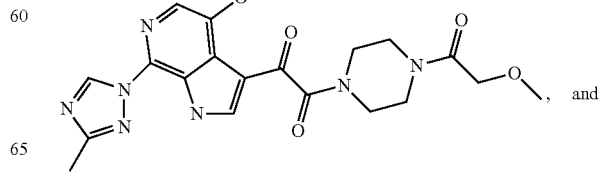, and -continued

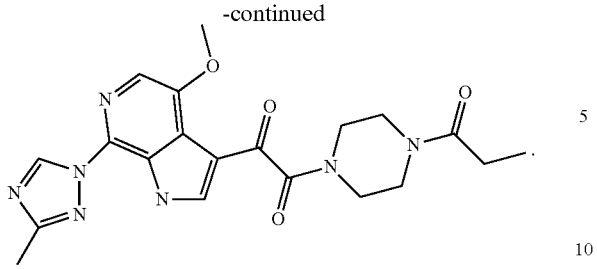

2. A pharmaceutical composition which comprises an antiviral effective amount of one or more of the compounds of Formula I as claimed in claim 1, together with one or more pharmaceutically acceptable carriers, excipients or diluents.

3. A method for treating a mammal infected with HIV comprising administering to said mammal an antiviral effective amount of a compound of Formula I as claimed in claim 1, and one or more pharmaceutically acceptable carriers, excipients or diluents.

* * * * *